(12) United States Patent
Akaike et al.

(10) Patent No.: US 7,211,589 B2
(45) Date of Patent: May 1, 2007

(54) ATISANE COMPOUNDS AND USE THEREOF

(75) Inventors: Akinori Akaike, Kyoto (JP); Hachiro Sugimoto, Ibaraki (JP); Yukio Nishizawa, Ibaraki (JP); Masahiro Yonaga, Ibaraki (JP); Naoki Asakawa, Ibaraki (JP); Naoki Asai, Ibaraki (JP); Nariyasu Mano, Miyagi (JP); Taro Terauchi, Ibaraki (JP); Takashi Doko, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 181 days.

(21) Appl. No.: 10/471,025

(22) PCT Filed: Apr. 25, 2002

(86) PCT No.: PCT/JP02/04155
§ 371 (c)(1),
(2), (4) Date: Oct. 9, 2003

(87) PCT Pub. No.: WO02/088061
PCT Pub. Date: Nov. 7, 2002

(65) Prior Publication Data
US 2004/0180930 A1 Sep. 16, 2004

(30) Foreign Application Priority Data
Apr. 27, 2001 (JP) .............................. 2001-133209

(51) Int. Cl.
C07D 211/06 (2006.01)
A61K 31/445 (2006.01)
A61K 31/40 (2006.01)
A61K 31/275 (2006.01)
A61K 31/13 (2006.01)

(52) U.S. Cl. ...................... 514/319; 514/408; 514/519; 514/661; 546/195; 548/528; 558/429; 564/453

(58) Field of Classification Search ................ 514/319, 514/408, 519, 661; 546/195; 548/528; 558/429; 564/453
See application file for complete search history.

(56) References Cited

OTHER PUBLICATIONS

Zalkow et al ("The Synthesis of 5a,8,8-Trimethyl-3, 10a-ethnaeoperhydrophenanthrene Terpenes", Journal of Organic Chemistry 28(8), pp. 2037-2039).*
Kume et al ("Isolation of diterpenoid substance with potent neuroprotective activity from fetal calf serum", PNAS, Feb. 26, 2002).*
Toshiaki Kume et al.; Proceedings of the National Academy of Sciences of the United States of America, vol. 99, No. 5, pp. 3288-3293, Mar. 5, 2002.
Russell A. Bell et al.; Tetrahedron Letters, No. 4, pp. 269-273, 1963.
K.M. Baker et al.; Journal of the Chemical Society, Perkin Transactions, 1972, pp. 190-194.
Robert M. Coates et al.; Journal of Organic Chemistry, vol. 36, No. 18, pp. 2625-2631, 1971.
Michael H. Beale et al.; Phytochemistry, vol. 22, No. 4, pp. 875-881, 1983.
Masataka Ihara et al.; Journal of the Chemical Society, Perkin Transactions 1: Organic and Bio-organic Chemistry (1986), (12), pp. 2151-2161.
Georgette Hugel et al.; Bulletin de la Societe Chimique de France, pp. 2894-2902, 1965.
L.H. Zalkow et al.; J. Chem. Soc., Suppl. No. 1, pp. 5497-5503, 1964.
S.W. Pelletier et al.; Chemical Communications, No. 15, pp. 830-831, 1968.
Jan St. Pyrek; Journal of Natural Products, vol. 47, No. 5, pp. 822-827, Sep.-Oct. 1984.
Alan J. McAlees et al.; J. Chem. Soc., Perkin Trans. 1, 1975, No. 9, pp. 861-869.
Helen Margaret Campbell et al.; Can. J. Chem., 1975, vol. 53, No. 1, pp. 20-25.
Russell A. Bell et al.; J. Org. Chem., 1966, vol. 31, No. 8, pp. 2536-2542.
Dennis W. Choi; Trends Neurosci., 11, pp. 465-469, 1988.
Brian Meldrum et al.; Trends Pharmacol. Sci., 11, pp. 379-387, 1990.
Toshiaki Kume et al.; Jpn. J. Pharmacol. vol. 73, pp. 371-374, 1997.
G. Topcu et al.; Phytochemistry, vol. 30, No. 7, pp. 2412-2413, 1991.
Mariano Pinar et al.; Journal of Natural Products, vol. 49, No. 2, pp. 334-335, Mar.-Apr. 1986.
M. Isabel Carrascal et al.; Anales De Quimica; 1977, vol. 73, No. 3, pp. 442-444.
Martin Benoit Ngassoum et al.; J. Essent. Oil Res., vol. 11, No. 3, pp. 283-288, 1999.
Braulio M. Fraga et al.; Biochemical Systematics and Ecology, vol. 23, No. 7/8, pp. 835-842, 1995.
Yi-Li Ding et al.; Phytochemistry, 1991, vol. 30, No. 7, pp. 2413-2415.

(Continued)

*Primary Examiner*—Samuel Barts
(74) *Attorney, Agent, or Firm*—Birch, Stewart, Kolasch & Birch, LLP

(57) ABSTRACT

The present invention provides a novel compound exhibiting an excellent suppressing effect to cell injury caused by radicals and neurotoxicity induced by excitatory nuerotransmitters such as glutamate. Specifically, it provides a compound represented by the following formula, a salt thereof or a hydrate of them.

(I)

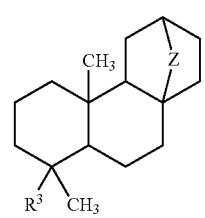

Wherein Z represents a bivalent organic group and the like of from 2 to 3 carbon atom(s) which may have a substituent; and $R^3$ represents a carboxyl group and the like.

22 Claims, 2 Drawing Sheets

OTHER PUBLICATIONS

Braulio M. Fraga et al.; Phytochemistry, vol. 30, No. 3, pp. 913-915, 1991.
C. Zdero et al.; Phytochemistry, vol. 29, No. 10, pp. 3201-3206, 1990.
Miguel P. L. Moraes et al.; Phytochemistry, vol. 27, No. 10, pp. 3205-3208, 1988.
A.M. Giesbrecht et al.; Brazilian J. Med. Biol. Res.; 1987, vol. 20, No. 6, pp. 807-810.
Ngassoum et al, Journal of Essential Oil Research, 1999, vol. 11, No. 3, pp. 283-288.
Fraga, et al, Biochem. Syst. Ecol., 1995, vol. 23, No. 7/8, pp. 835-842.
Ding et al, Phytochemistry, 1991, vol. 30, No. 7, pp. 2413-2415.
Fraga et al, Phytochemistry, 1991, vol. 30, No. 3, pp. 913-915.
Zdero et al, Phytochemistry, 1990, vol. 29, No. 10, pp. 3201-3206.
Moraes et al, Phytochemistry, 1988, vol. 27, No. 10, pp. 3205-3208.
Giesbrecht et al, Braz. J. Med. Biol. Res., 1987, vol. 20, No. 6, pp. 807-810.
St. Pyrek, J. Nat. Prod., 1984, vol. 47, No. 5, pp. 822-827, p. 826.
Mcalees et al, J. Chem. Soc., Perkin Trans. 1, 1975, No. 9, pp. 861-869.
Campbell et al, Can. J. Chem., 1975, vol. 53, No. 1, pp. 20-25.
Carrascal et al, An. Qium, 1977, vol. 73, No. 3, pp. 442-443.
Bell et al, J. Org. Chem, 1966, vol. 31, No. 8, pp. 2536-2542.

* cited by examiner

ATISANE COMPOUNDS AND USE THEREOF

This application is the national phase under 35 U.S.C. § 371 of PCT International Application No. PCT/JP02/04155 which has an International filing date of Apr. 25, 2002, which designated the United States of America.

FIELD OF THE INVENTION

The present invention relates to a novel atisane compound and a pharmaceutical thereof.

PRIOR ART

Excitatory neurotransmitters such as glutamate and aspartate interact with their specific receptors to play critical roles in developing neurological function such as recognition, anamnesis, movement, sensation and so on. On the other hand, it is widely known that they may cause some types of neurologic disease by inducing neurotoxicity. For example, according to a previously report, glutamate interacts with N-methyl-D-aspartate (NMDA) receptor, α-amino-3-hydroxy-5-metyl-4-isoxazolepropionic acid (AMPA) receptor and so on to cause nerve cell death by promoting release of $Ca^{2+}$ and production of nitric monoxide (NO), and thus is the most significant curse to develop a number of nerve diseases such as cranial nerve disorder due to hypoxia (Choi D W, Trends Neurosci 11, 465–469 (1988), Meldrum B and Garthwaite J, Trends Pharmacol Sci 11, 379–387 (1990)). A great many reports have identified nerve diseases that are considered to result from neurotoxicity induced by neurotransmitters such as glutamate. Examples of such nerve diseases include acute neurodegenerative diseases such as subarachnoid hemorrhage, cerebrovascular disorder acute stage, head injury, spinal cord injury, or neuropathy due to hypoxia or hypoglycemia, chronic neurodegenerative diseases such as Alzheimer's disease, Parkinson's disease, Huntington's chorea, amyotrophic lateral sclerosis (ALS), multiple sclerosis or spinocerebellar degeneration, chronic intractable disease, epilepsy, hepatic encephalopathy, peripheral neuropathy, Parkinson syndrome, spastic paralysis, pain, neuralgia, anxiety, drug dependence, nausea, vomiting, urination disorder, visual disorder due to glaucoma, retinopathy of prematurity, diabetic retinopathy, macular degeneration, hearing disorder by antibiotics, food poisoning and the like. It is suggested that depolarization of nerves, excess release of glutamate, changes in characteristic and developing pattern of glutamate receptor and the like are involved in increasing the sensitivity to neural glutamate.

For treatment and prevention of the aforementioned neurologic diseases, pharmaceuticals having neuroprotective functions and pharmaceuticals which are usuful for cell injury due to radicals would be especially effective. However, compound which effectively suppress the neurotoxicity of glutamate and the like or exhibit antioxidation function, while exerting utility as pharmaceuticals have not been found heretofore. Meanwhile, the present inventors previously found and reported that ether extract of fetal calf serum (hereinafter referred to as "EE-FCS") significantly inhibits neurotoxicity due to glutamate or S-nitrosocystaine which is a NO inducer (Jpn. J. Pharmacol. 73, 371–374 (1997)), but have not isolated bioactive substance involved in EE-FCS yet.

As an atisane compound, 16,19-atisane diol, (Phytochemistry, 1991, 30, 2413) represented by the formula:

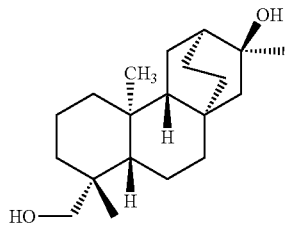

and 15-hydroxy-16-atisane-19-oic acid (J. Nat. Prod., 1986, 49, 334) represented by the formula:

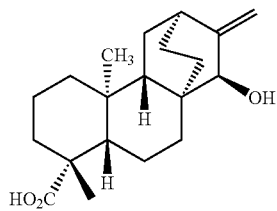

and the like are known, but other types of atisane compounds represented by the formula (I) of the present invention have not been known as for now.

DISCLOSURE OF THE INVENTION

In view of the above circumstances, the present inventors made intensive research for isolating and characterizing bioactive substances involved in EE-FCS, and finally succeeded in isolating and characterizing the novel atisane derivatives represented by the formula:

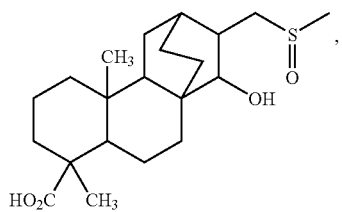

and found that the atisane derivatives exhibit a protective effect against cell injury due to radicals while exerting an excellent neural protective effect against neurotoxicity induced by glutamate or the like. Based on these findings, they succeeded in synthesizing novel atisane compounds, and found that such compounds, a salt thereof and a hydrate of them exhibit protective effects against cell injury due to radicals, while are very useful as inhibitors of neurotoxicity induced by excitatory neurotransmitters such as glutamate and the like, and accomplished the present invention.

Specifically, the present invention relates to:

<1> a compound represented by the following formula:

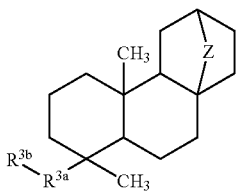
(1)

(wherein Z represents a bivalent organic group of from 2 to 3 carbon atoms, provided that Z may have one or two group(s) selected from the group consisting of those represented by the following formula:

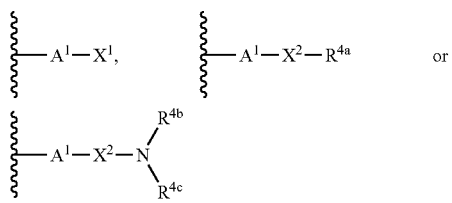

(wherein $A^1$ represents an optionally substituted $C_{1-6}$ alkylene group or a single bond; $X^1$ represents a halogen atom or a cyano group; $X^2$ represents the formula $-S(O)_m-$ (wherein m is an integer of 0, 1 or 2), an oxygen atom, a carbonyl group or a single bond; $R^{4a}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{1-6}$ alkoxy group or a hydroxyl group; and $R^{4b}$ and $R^{4c}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group), and the case where Z is a 1,2-ethylene group not having a substituent or a 1,2-vinylene group not having a substituent is excluded;

$R^{3a}$ represents a carbonyl group, a methylene group or a single bond; and $R^{3b}$ represents a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, a hydroxyl group, a cyano group or a group represented by the formula $-NR^{5a}R^{5b}$ (wherein, $R^{5a}$ and $R^{5b}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group), provided that the following cases (1) to (3) are excluded:

(1) Z represents a 1,2-dicarboxyethane-1,2-yl group or a 1,2-dimethoxycarbonylethane-1,2-yl group, and the formula $-R^{3a}-R^{3b}$ represents a hydroxymethyl group or an acetoxymethyl group;

(2) Z represents a 1-i-propylethane-1,2-yl group and the formula $-R^{3a}-R^{3b}$ represents a hydrogen atom; and (3) the formula $-R^{3a}-R^{3b}$ represents a methyl group, and Z represents the formula:

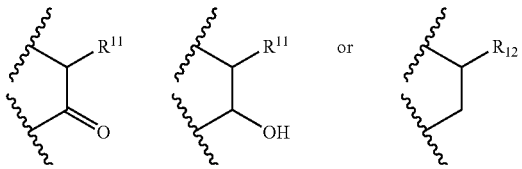

(wherein $R^{11}$ represents a hydrogen atom or a methyl group, and $R^{12}$ represents a hydroxyl group, a methyl group or a tetrahydropyran-2H-pyran-2-yl-oxy group)), a salt thereof or a hydrate of them;

<2> a compound represented by the following formula:

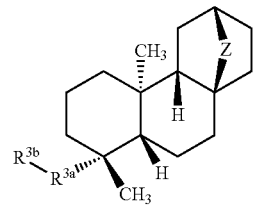
(Ia)

(wherein Z, $R^{3a}$ and $R^{3b}$ respectively represent those defined for the above Z, $R^{3a}$ and $R^{3b}$ in claim 1, provided that the following cases (1) to (3) are excluded:

(1) Z represents a 1,2-dicarboxyethane-1,2-yl group or a 1,2-dimethoxycarbonylethane-1,2-yl group, and the formula $-R^{3a}-R^{3b}$ represents a hydroxymethyl group or an acetoxymethyl group;

(2) Z represents a 1-i-propylethane-1,2-yl group and the formula $-R^{3a}-R^{3b}$ represents a hydrogen atom; and (3) the formula $-R^{3a}-R^{3b}$ represents a methyl group, and Z represents the formula:

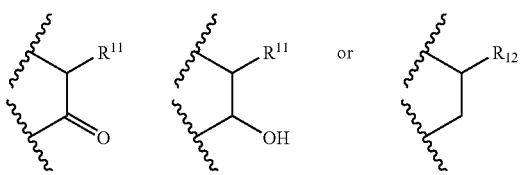

(wherein $R^{11}$ represents a hydrogen atom or a methyl group, and $R^{12}$ represents a hydroxyl group, a methyl group or a tetrahydropyran-2H-pyran-2-yl-oxy group)), a salt thereof or a hydrate of them;

the compound according to the above <1> or <2>, a salt thereof or a hydrates thereof, wherein Z is a group represented by the formula:

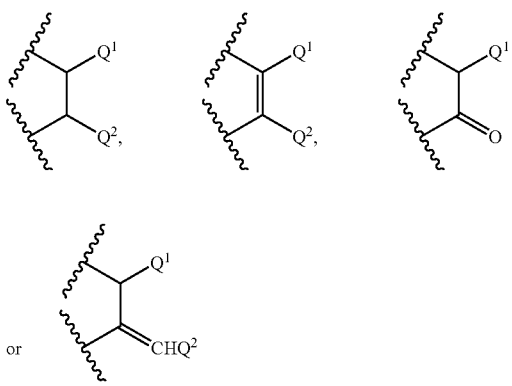

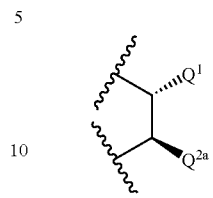

<5> the compound according to the above <1> or <2>, a salt thereof or a hydrate of them, wherein Z is a group represented by the formula:

(wherein $Q^1$ and $Q^2$ are independent of each other and each represents a group represented by the formula:

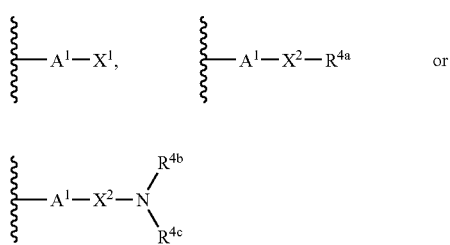

(wherein $Q^1$ is as defined for $Q^1$ in the above <3>; and $Q^{2a}$ is as defined for $Q^{2a}$ in the above <4>);

<6> the compound according to the above <1> or <2>, a salt thereof or a hydrate of them, wherein Z is a group represented by the formula:

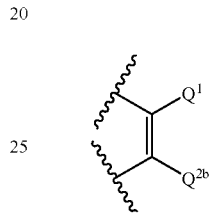

(wherein $A^1$, $X^1$, $X^2$, $R^{4a}$, $R^{4b}$ and $R^{4c}$ respectively represent those defined for $A^1$, $X^1$, $X^2$, $R^{4a}$, $R^{4b}$ and $R^{4c}$ in the above <1>));

<4> the compound according to the above <1> or <2>, a salt thereof or a hydrate of them, wherein Z is a group represented by the formula:

(wherein $Q^1$ is as defined for $Q^1$ in the above <3>; and $Q^{2b}$ represents a hydrogen atom or an optionally substituted $C_{1-6}$ alkyl group);

<7> the compound according to the above <1> or <2>, a salt thereof or a hydrate of them, wherein Z is a group represented by the formula:

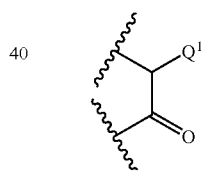

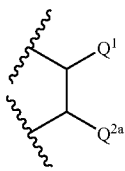

(wherein $Q^1$ is as defined for $Q^1$ in claim 3; and $Q^{2a}$ represents a hydrogen atom, a halogen atom, an optionally substituted $C_{1-6}$ alkyl group, an optionally substituted $C_{2-6}$ alkenyl group, an optionally substituted. $C_{2-6}$ alkynyl group, an optionally substituted $C_{1-6}$ alkoxy group, a hydroxyl group or a group represented by the formula —$NR^{6a}R^{6b}$ (wherein $R^{6a}$ and $R^{6b}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{2-7}$ acyl group or an optionally substituted $C_{1-6}$ alkylsulfonyl group));

(wherein $Q^1$ is as defined for $Q^1$ in the above <3>);

<8> the compound according to the above <1> or <2>, a salt thereof or a hydrate of them, wherein z is a group represented by the formula:

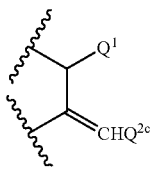

(wherein $Q^1$ is as defined for $Q^1$ in the above <3>; and $Q^{2c}$ represents a hydrogen atom, a cyano group, a formyl group, a carboxyl group, an optionally substituted $C_{1-6}$ alkyl group, an optionally substituted $C_{2-7}$ acyl group, an optionally substituted $C_{2-7}$ alkoxycarbonyl group or a group represented by the formula:

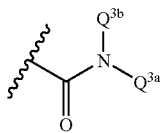

(wherein $Q^{3a}$ and $Q^{3b}$ are independent of each other and each represents a hydrogen atom, an optionally substituted $C_{1-6}$ alkyl group, an optionally substituted $C_{2-6}$ alkenyl group or an optionally substituted $C_{2-6}$ alkynyl group));

<9> the compound according to any one of the above <1> to <8>, a salt thereof or a hydrate of them, wherein $R^{3a}$ is a carbonyl group;

<10> the compound according to any one of the above <1> to <9>, a salt thereof or a hydrate of them, wherein $R^{3b}$ is a hydroxyl group;

<11> the compound according to any one of the above <4>, <5>, <9> and <10>, a salt thereof or a hydrate of them, wherein $Q^{2a}$ is a hydroxyl group;

<12> the compound according to any one of the above <3> to <11>, a slat thereof or a hydrate of them, wherein $Q^1$ is a group represented by the formula $-A^1-S(O)_m-R^{4a}$ (wherein $A^1$, m and $R^{4a}$ are respectively as defined for $A^1$, m and $R^{4a}$ in the above <1>);

<13> the compound according to any one of the above <1> to <12>, a salt thereof or a hydrate of them, wherein $R^{4a}$ is an optionally substituted methyl group, an optionally substituted ethyl group, an optionally substituted n-propyl group or an optionally substituted i-propyl group;

<14> the compound according to any one of the above <1> to <13>, a salt thereof or a hydrate of them, wherein $A^1$ is a methylene group;

<15> the compound according to any one of the above <1> to <14>, a salt thereof or a hydrate of them, wherein m is 1;

<16> the compound according to any one of the above <1> to <8>, a salt thereof or a hydrate of them, wherein $A^1$ represents a $C_{1-6}$ alkylene group or a single bond; $R^{4a}$ represents a hydrogen atom, a $C_{1-6}$ alkyl group, a $C_{2-6}$ alkenyl group, a $C_{2-6}$ alkynyl group, a $C_{6-14}$ aromatic hydrocarbon cyclic group, a 5- to 14-membered aromatic heterocyclic group, a $C_{1-6}$ alkoxy group or a hydroxyl group; $R^{4b}$ and $R^{4c}$ are independent of each other and each represents a hydrogen atom, a $C_{1-6}$ alkyl group, a $C_{2-6}$ alkenyl group, a $C_{2-6}$ alkynyl group, a $C_{6-14}$ aromatic hydrocarbon cyclic group, a 5- to 14-membered aromatic heterocyclic group, a $C_{2-7}$ acyl group or a $C_{1-6}$ alkylsulfonyl group; and $R^{3b}$ represents a hydrogen atom, a halogen atom, a $C_{1-6}$ alkyl group, a $C_{2-6}$ alkenyl group, a $C_{2-6}$ alkynyl group, a $C_{1-6}$ alkoxy group, a hydroxyl group, a cyano group or a group represented by the formula $-NR^{5a}R^{5b}$ (wherein $R^{5a}$ and $R^{5b}$ are independent of each other and each represents a hydrogen atom, a $C_{1-6}$ alkyl group, a $C_{2-6}$ alkenyl group, a $C_{2-6}$ alkynyl group, a $C_{6-14}$ aromatic hydrocarbon cyclic group, a 5- to 14-membered aromatic heterocyclic group, a $C_{2-7}$ acyl group or a $C_{1-6}$ alkylsulfonyl group);

<17> the compound according to the above <4> or <5>, a salt thereof or a hydrate of them, wherein $Q^{2a}$ represents a hydrogen atom, a halogen atom, a $C_{1-6}$ alkyl group, a $C_{2-6}$ alkenyl group, a $C_{2-6}$ alkynyl group, a $C_{1-6}$ alkoxy group, a hydroxyl group or a group represented by the formula $-NR^{6a}R^{6b}$ (wherein $R^{6a}$ and $R^{6b}$ are independent of each other and each represents a hydrogen atom, a $C_{1-6}$ alkyl group, a $C_{2-6}$ alkenyl group, a $C_{2-6}$ alkynyl group, a $C_{2-7}$ acyl group or a $C_{1-6}$ alkylsulfonyl group);

<18> a medicament comprising the compound according to the above <1> or <2>, a salt thereof or a hydrate of them;

<19> a pharmaceutical composition comprising the compound according to the above <1> or <2>, a salt thereof or a hydrate of them;

<20> a protective agent against cell injury due to radicals, comprising the compound according to the above <1> or <2>, a salt thereof or a hydrate of them;

<21> an inhibitor of glutamate-induced neurotoxicity, comprising the compound according to the above <1> or <2>, a salt thereof or a hydrate of them;

<22> an inhibitor of NO-induced neurotoxicity, comprising the compound according to the above <1> or <2>, a salt thereof or a hydrate of them;

<23> an agent for treating or preventing a disease to which glutamate-induced neurotoxicity relates, which comprises the compound according to the above <1> or <2>, a salt thereof or a hydrate of them;

<24> an agent for treating or preventing a disease to which NO-induced neurotoxicity relates, which comprises the compound according to the above <1> or <2>, a salt thereof or a hydrate of them;

<25> an agent for treating or preventing nervous disease, which comprises the compound according to the above <1> or <2>, a salt thereof or a hydrate of them;

<26> the agent for treating or preventing nervous disease according to the above <25>, wherein the nervous disease is disorder by cerebral ischemia, Parkinson disease, Alzheimer disease, amyotrophic lateral sclerosis (ALS) or multiple sclerosis;

<27> an agent for treating or preventing glaucoma, retinopathy of prematurity, diabetic retinopathy, macular degeneration or hearing disorder, which comprises the compound according to the above <1> or <2>, a salt thereof or a hydrate of them;

<28> an agent for treating or preventing skin disease, which comprises the compound according to the above <1> or <2>, a salt thereof or a hydrate of them; and <29> the agent for treating or preventing skin disease according to the above <28>, wherein the skin disease is atopic dermatitis, contact dermatitis or hyperesthesia.

The present invention provides a method for treating or preventing a disease to which a protection against cell injury due to radicals is efficacious, a disease to which glutamate-induced neurotoxicity relates, a disease to which NO-induced neurotoxicity relates, a nervous disease, glaucoma, retinopathy of prematurity, diabetic retinopathy, macular degeneration, hearing disorder or a skin disease, by administering a pharmacologically effective amount of the compound according to the above <1> or <2>, a salt thereof or a hydrate of them to a patient. The present invention also provides use of the compound according to the above <1> or <2>, a salt thereof or a hydrate of them, for producing an agent for treating or preventing a disease to which a protection against cell injury due to radicals is efficacious, a disease to which glutamate-induced neurotoxicity relates, a disease to which NO-induced neurotoxicity relates, a nervous disease, glaucoma, retinopathy of prematurity, diabetic retinopathy, macular degeneration, hearing disorder or a skin disease.

Hereinafter, definition for terms, symbols and the like used in the present description will be made, and detailed explanation on the present invention will be made.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present, but the present invention is not limited to them and includes any one. In addition, a crystal polymorphism may be present but is not limiting, but any crystal form may be single or a crystal form mixture, or an anhydride or hydrate.

In this description, "$C_{1-6}$ alkyl group" refers to linear or branched alkyl groups of from 1 to 6 carbon atom(s), and concrete examples thereof include methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 2-ethyl propyl group, 1-methyl-2-ethyl propyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, 3-methylpentyl group and so on.

"$C_{1-6}$ alkylene group" used in the present description refers to bivalent groups derived from "$C_{1-6}$ alkyl group" defined above by removing one hydrogen atom, and concrete examples thereof include methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group, hexamethylene group and the like, and preferably methylene group, 1,2-ethylene group, 1,3-propylene group and so on, more preferably methylene group.

In the present description, "$C_{2-6}$ alkenyl group" refers to linear or branched alkenyl groups of from 2 to 6 carbons, and concrete examples thereof include vinyl group, allyl group, 1-propenyl group, isopropenyl group, 1-buten-1-yl group, 1-buten-2-yl group, 1-buten-3-yl group, 2-buten-1-yl group, 2-buten-2-yl group and the like.

In the present description, "$C_{2-6}$ alkynyl group" refers to linear or branched alkynyl group of from 2 to 6 carbons, and concrete examples thereof include ethynyl group, 1-propynyl group, 2-propynyl group, butynyl group, pentynyl group, hexynyl group and the like.

In the present description, "$C_{6-14}$ aromatic hydrocarbon cyclic group" refers to aromatic cyclic groups of from 6 to 14 carbons, and concrete examples thereof include phenyl group, 1-naphthyl group, 2-naphthyl group, as-indacenyl group, s-indacenyl group, acenaphthylenyl group and so on, and preferably phenyl group, 1-naphthyl group and 2-naphthyl group.

In the present description, "from 5- to 14-membered aromatic heterocyclic group" refers to aromatic cyclic groups wherein the number of atoms constituting the cyclic group is from 5 to 14, and the kind of atoms constituting the cyclic group is a carbon atom or a hetero atom, and concrete examples include pyridine, thiophene, furan, pyrrole, oxazole, isoxazole, thiazole, isothiazole, imidazole, triazole, pyrazole, furazan, thiadiazole, oxadiazole, pyridazine, pyrimidine, pyrazine, indole, isoindole, indazole, chromene, quinoline, isoquinoline, cinnoline, quinazoline, quinoxaline, naphthylidene, phthalazine, purine, pteridine, thienofuran, imidazothiazole, benzofuran, benzothiophene, benzoxazole, benzthiazole, benzthiadiazole, benzimidazole, imidazopyridine, pyrrolopyridine, pyrrolopyrimidine, pyridopyrimidine and the like.

In the present description, "$C_{3-8}$ cycloalkyl group" refers to cyclic aliphatic hydrocarbon groups of from 3 to 8 carbons, and concrete examples include cyclopropyl group, cyclobutyl group, cyclopentyl group, cyclohexyl group, cycloheptyl group, cyclopropenyl group, cyclobutenyl group, cyclopentenyl group, cyclohexenyl group, cycloheptenyl group and the like.

In the present description, "halogen atom" refers to fluorine atom, chlorine atom, bromine atom or iodine atom.

In the present description, "$C_{1-6}$ alkoxy group" refers to oxy groups to which "$C_{1-6}$ alkyl group" as defined above is bound, and concrete examples include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group, 1-ethyl-2-methylpropoxy group and the like.

In the present description, "$C_{2-7}$ acyl group" refers to carbonyl groups to which "$C_{1-6}$ alkyl group" defined above is bound, and concrete examples include acetyl group, propionyl group, butyryl group, isobutyryl group and the like.

In the present description, "$C_{1-6}$ alkoxycarbonyl group" refers to carbonyl groups to which "$C_{1-6}$ alkoxy group" as defined above is bound, and concrete examples include methoxycarbonyl group, ethoxycarbonyl group, n-propoxycarbonyl group, i-propoxycarbonyl group, n-butoxycarbonyl group, i-butoxycarbonyl group, sec-butoxycarbonyl group, t-butoxycarbonyl group and the like.

In the present description, "$C_{1-6}$ alkylsulfonyl group" refers to sulfonyl groups to which "$C_{1-6}$ alkyl group" as defined above is bound, and concrete examples include methylsulfonyl group, propylsulfonyl group and the like.

The term "an optionally substituted" used in the present description is synonymous with "which may have one or more substituents in any combination at a site where such substitution is possible". Concrete examples of such substituents include:
(1) halogen atom,
(2) hydroxyl group,
(3) thiol group,
(4) nitro group,
(5) nitrile group,
(6) oxo group,
(7) azido group,
(8) guanidino group,
(9) hydrazino group,
(10) isocyano group,
(11) cyanate group,
(12) isocyanate group,
(13) thiocyanate group,
(14) isothiocyanate group,
(15) nitroso group,
(16) carbamide group
(17) formyl group,

(18) $C_{1-6}$ imidoyl group,
(19) $C_{1-6}$ alkyl group, $C_{2-6}$ alkenyl group, $C_{2-6}$ alkynyl group, $C_{3-8}$ cycloalkyl group, $C_{1-6}$ alkoxy group, $C_{2-6}$ alkenyloxy group, $C_{2-6}$ alkynyloxy group, $C_{3-6}$ cycloalkyloxy group, $C_{1-6}$ alkylthio group, $C_{2-6}$ alkenylthio group, $C_{2-6}$ alkynylthio group, $C_{3-6}$ cycloalkylthio group or $C_{1-6}$alkylene dioxy group, each of which may be substituted with from 1 to 3 halogen atom(s) or hydroxyl group(s),
(20) $C_{6-14}$ aryl group,
(21) from 5- to 14-membered heterocyclic group,
(22) carboxyl group,
(23) trifluoromethyl group,
(24) $C_{6-14}$ aryl $C_{1-6}$ alkyl group,
(25) from 5- to 14-membered heterocyclic $C_{1-6}$ alkyl group,
(26) $C_{1-6}$ alkylcarbamoyl group,
(27) $C_{1-6}$ alkoxycarbonyl group,
(28) $C_{1-6}$ alkylcarbonyl group,
(29) $C_{1-6}$ alkylcarbonyloxy group,
(30) $C_{1-6}$ alkylsulfonyl group,
(31) $C_{1-6}$ alkylsulfinyl group, and the like substituents, and among these substituents,
(1) halogen atom,
(2) hydroxyl group,
(5) nitrile group,
(16) carbamide group,
(19) $C_{1-6}$ alkyl group, $C_{2-6}$ alkenyl group, $C_{2-6}$ alkynyl group, $C_{3-8}$ cycloalkyl group, $C_{1-6}$ alkoxy group or $C_{3-6}$ cycloalkyloxy group, each of which maybe substituted with from 1 to 3 halogen atom(s) or hydroxyl group(s),
(20) $C_{6-14}$ aryl group,
(21) from 5- to 14-membered heterocyclic group,
(22) carboxyl group,
(23) trifluoromethyl group,
(24) $C_{6-14}$ aryl $C_{1-6}$ alkyl group,
(25) from 5- to 14-membered heterocyclic $C_{1-6}$ alkyl group,
(26) $C_{1-6}$ alkylcarbamoyl group,
(27) $C_{1-6}$ alkoxycarbonyl group,
(28) $C_{1-6}$ alkylcarbonyl group,
(29) $C_{1-6}$ alkylcarbonyloxy group,
(30) $C_{1-6}$ alkylsulfonyl group,
(31) $C_{1-6}$ alkylsulfinyl group and the like substituents are preferred, and
(1a) halogen atom,
(2a) hydroxyl group,
(3a) nitrile group,
(4a) $C_{1-6}$ alkyl group,
(5a) $C_{3-8}$ cycloalkyl group,
(6a) $C_{1-6}$ alkoxy group,
(7a) phenyl group,
(8a) carboxyl group,
(9a) $C_{1-6}$ alkylcarbamoyl group,
(10a) $C_{1-6}$ alkylsulfonyl group and the like substituents are more preferred.

Z represents a bivalent organic group of from 2 to 3 carbon atoms, provided that Z may have one or two group(s) selected from the group consisting of the following formulae:

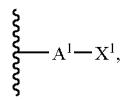 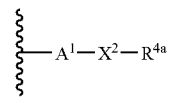 or

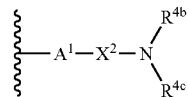

(wherein $A^1$, $X^1$, $X^2$, $R^{4a}$, $R^{4b}$ and $R^{4c}$ have the same meanings as defined in the above definitions) with the exception that Z is 1,2-ethylene group not having a substituent or 1,2-vinylene group not having a substituent.

The term "bivalent organic group of from 2 to 3 carbon atoms" refers to bivalent organic groups optionally containing one oxygen atom as a carbonyl group and comprising from 2 to 3 carbon atoms wherein the atom involving in constituting the ring in Z is methylene group, methine group, carbon atoms or carbonyl group, and concrete examples include the groups represented by the following formulae:

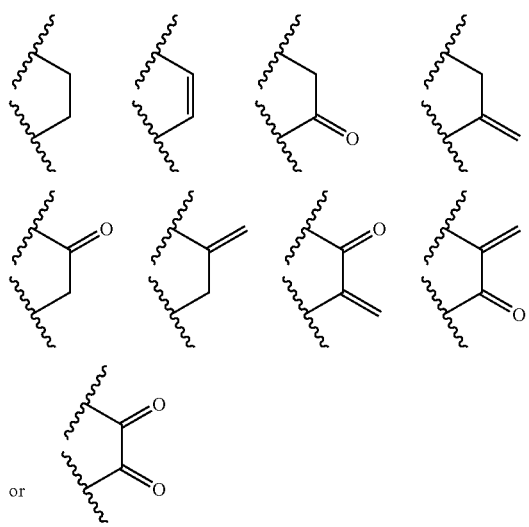

or

The "bivalent organic group of from 2 to 3 carbon atoms" is preferably 1,2-ethylene group, 1,2-vinylene group, ethanone-1,2-ylene group or 1-propene-2,3-ylene group and the like, more preferably the groups represented by the following formulae:

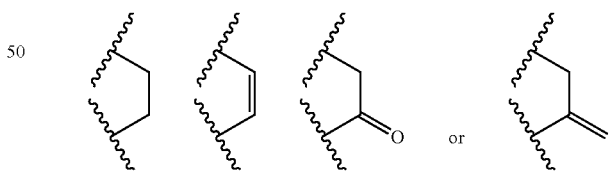

still preferably the groups represented by the following formulae:

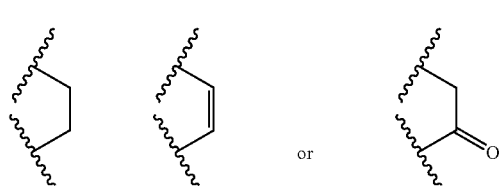

and most preferably the groups represented by the following formulae:

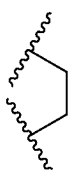 or 

The formula:

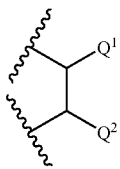

(wherein $Q^1$ and $Q^2$ have the same meanings as defined above) represents groups containing from 1 to 4 group(s) selected from the group consisting of:

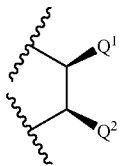
(Q-1a)

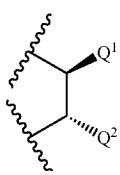
(Q-1b)

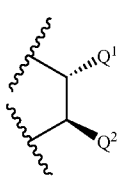
(Q-1c)

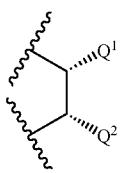
(Q-1d)

(wherein $Q^1$ and $Q^2$ have the same meanings as defined above) at any ratio, and preferably the group represented by the above (Q-1a), (Q-1b), (Q-1c) or (Q-1d).

The formula:

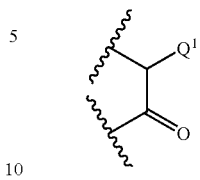

(wherein $Q^1$ has the same meaning as defined above) represents groups containing from 1 to 2 group(s) selected from the group consisting of:

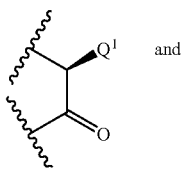
(Q-2a)

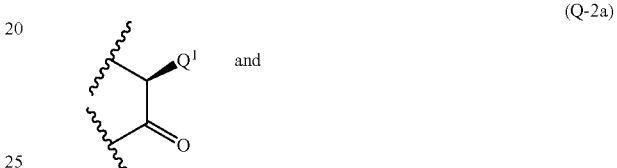
(Q-2b)

(wherein $Q^1$ has the same meaning as defined above) at any ratio, preferably the group represented by the above (Q-2a) or (Q-2b), more preferably the group represented by the above (Q-2a), and still preferably the group represented by the above (Q-2b).

The formula:

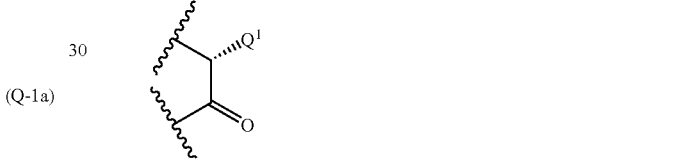

(wherein $Q^1$ and $Q^2$ have the same meanings as defined above) represents groups containing from 1 to 2 group(s) selected from the group consisting of:

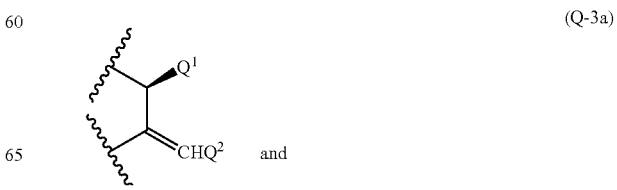
(Q-3a)

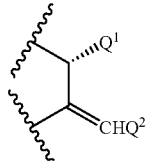
(Q-3b)

(wherein $Q^1$ and $Q^2$ have the same meanings as defined above) at any ratio, preferably the group represented by the above (Q-3a) or (Q-3b), more preferably the group represented by the above (Q-3a), and still preferably the group represented by the above (Q-3b).

In the above compound (I), "Z is a group represented by the formula:

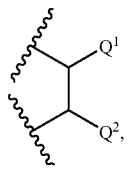 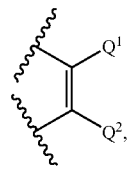 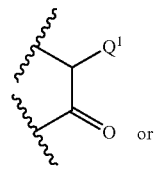 or

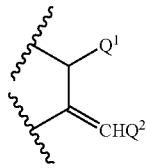

(wherein $Q^1$ and $Q^2$ have the same meanings as defined above)" represents that the above compound (I) is represented by the formula:

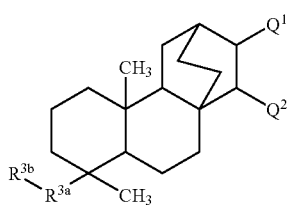

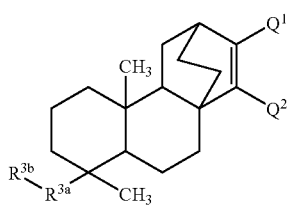

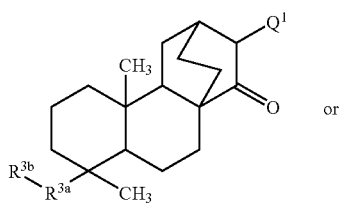 or

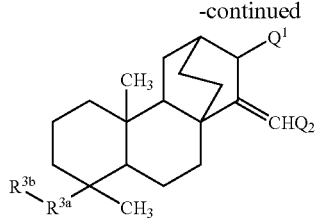

wherein $Q^1$, $Q^2$, $R^{3a}$ and $R^{3b}$ have the same meanings as defined above.

Z represents preferably the group represented by the formula:

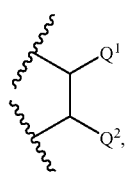 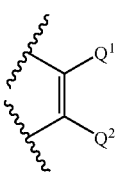 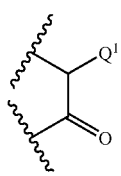
, or (wherein $Q^1$ and $Q^2$ have the same meanings as defined above), more preferably the group represented by the formula:

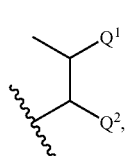 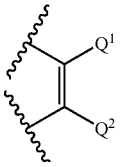 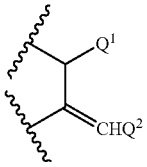
, or (wherein $Q^1$ and $Q^2$ have the same meanings as defined above), still preferably the group represented by the formula:

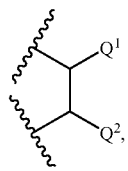 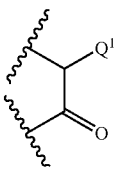 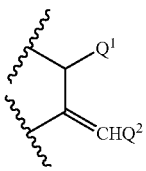
, or (wherein $Q^1$ and $Q^2$ have the same meanings as defined above), and most preferably the group represented by the formula:

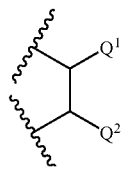 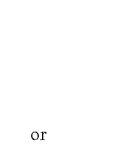
or wherein $Q^1$ and $Q^2$ have the same meanings as defined above.

The formula "—$R^{3a}$–$R^{3b}$" represents the group as defined above, preferably a carboxyl group, $C_{1-6}$ alkoxycarbonyl group, $C_{1-6}$ alkyl group, cyano group, groups represented by the formula —CO—$NR^{5a}R^{5b}$ (wherein $R^{5a}$ and $R^{5b}$ have the same meanings as defined above) or the formula —$CH_2$—$R^{30b}$ (wherein $R^{30b}$ represents $C_{1-6}$ alkoxy group or halogen atom), more preferably a carboxyl group, $C_{1-6}$ alkoxycarbonyl group, $C_{1-6}$ alkyl group, cyano group or groups represented by the formula —CO—$NR^{5a}R^{5b}$ (wherein $R^{5a}$ and $R^{5b}$ have the same meanings as defined above), still preferably a carboxyl group, methoxycarbonyl group, methyl group or cyano group, and most preferably a carboxyl group.

$Q^2$ represents the group as defined above, preferably a hydroxyl group, $C_{1-6}$ alkoxy group, halogen atom or groups represented by the formula —$NR^{4b}R^{4c}$ (wherein $R^{4b}$ and $R^{4c}$ have the same meanings as defined above), more preferably a hydroxyl group, halogen atom or —$NH_2$, and still preferably a hydroxyl group.

$Q^{2a}$ represents a hydrogen atom, halogen atom, optionally substituted $C_{1-6}$ alkyl group, optionally substituted $C_{2-6}$ alkenyl group, optionally substituted $C_{2-6}$ alkynyl group, optionally substituted $C_{1-6}$ alkoxy group, hydroxyl group, or groups represented by the formula —$NR^{6a}R^{6b}$ (wherein $R^{6a}$ and $R^{6b}$ are independent of each other and each represents hydrogen atom, optionally substituted $C_{1-6}$ alkyl group, optionally substituted $C_{2-6}$ alkenyl group, optionally substituted $C_{2-6}$ alkynyl group, optionally substituted $C_{2-7}$ acyl group or optionally substituted $C_{1-6}$ alkylsulfonyl group).

The above $Q^{2a}$ is preferably a halogen atom, optionally substituted $C_{1-6}$ alkyl group, optionally substituted $C_{1-6}$ alkoxy group, hydroxyl group or groups represented by the formula —$NR^{6a}R^{6b}$ (wherein $R^{6a}$ and $R^{6b}$ are independent of each other and each represents a hydrogen atom, optionally substituted $C_{1-6}$ alkyl group, optionally substituted $C_{2-7}$ acyl group or optionally substituted $C_{1-6}$ alkylsulfonyl group), more preferably a halogen atom, $C_{1-6}$ alkoxy group, hydroxyl group or —$NH_2$, and still preferably a hydroxyl group.

$Q^{2b}$ represents a hydrogen atom or optionally substituted $C_{1-6}$ alkyl group, preferably a hydrogen atom or methyl group, and more preferably a hydrogen atom.

$Q^1$ represents groups represented by the formula -$A^{10}$-$X^{10}$ (wherein $A^{10}$ represents an optionally substituted $C_{1-6}$ alkylene group or single bond, and $X^{10}$ represents —$X^1$, —$X^2$—$R^{4a}$ or —$X^2$—$NR^{4b}R^{4c}$ (wherein $X^1$, $X^2$, $R^{4a}$, $R^{4b}$ and $R^{4c}$ have the same meanings as described above).

$A^{10}$ is preferably a $C_{1-6}$ alkylene group or single bond, more preferably groups represented by the formula —$(CH_2)_s$— (wherein s represents an integer from 0 to 6), more preferably a single bond, methylene group or ethylene group, and most preferably a methylene group.

$X^{10}$ is preferably a halogen atom, cyano group or groups represented by the formula:

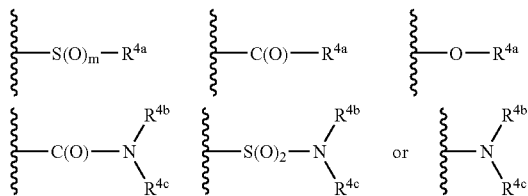

(wherein m, $R^{4a}$, $R^{4b}$ and $R^{4c}$ have the same meanings as defined above), more preferably groups represented by the formula:

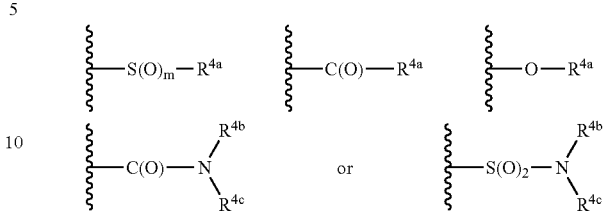

(wherein m, $R^{4a}$, $R^{4b}$ and $R^{4c}$ have the same meanings as defined above), and still preferably groups represented by the formula —S(O)—$R^{4a}$ (wherein $R^{4b}$ has the same meaning as defined above).

$R^{4a}$ represents the group as defined above, preferably a hydrogen atom, optionally substituted $C_{1-6}$ alkyl group, optionally substituted $C_{6-14}$ aromatic hydrocarbon cyclic group or optionally substituted from 5- to 14-membered aromatic heterocyclic group, more preferably a hydrogen atom, $C_{1-6}$ alkyl group or $C_{6-14}$ aromatic hydrocarbon cyclic group, still preferably a methyl group, ethyl group, n-propyl group or i-propyl group, and most preferably a methyl group.

$R^{4b}$ and $R^{4c}$ each represent the group as defined above, preferably a hydrogen atom, optionally substituted $C_{1-6}$ alkyl group, optionally substituted $C_{6-14}$ aromatic hydrocarbon cyclic group, optionally substituted from 5- to 14-membered aromatic heterocyclic group, optionally substituted $C_{2-7}$ acyl group or optionally substituted $C_{1-6}$ alkylsulfonyl group, more preferably a hydrogen atom, $C_{1-6}$ alkyl group, $C_{6-14}$ aromatic hydrocarbon cyclic group, $C_{2-7}$ acyl group or $C_{1-6}$ alkylsulfonyl group, still preferably a hydrogen atom, $C_{1-6}$ alkyl group or $C_{1-6}$ alkylsulfonyl group, and most preferably a hydrogen atom, methyl group or ethyl group.

It goes without saying that the present invention is not limited to these compounds, and preferred embodiments can be obtained by appropriately combining preferred examples of each reference symbol in the above formula (I).

"Salts" used in the present invention refer to any pharmaceutically acceptable salts insofar as they form addition salts with the compound of the present invention, and preferred examples include hydrohalides such as hydrofluorides, hydrochlorides, hydrobromides or hydriodides; inorganic acid salts such as sulfates, nitrates, perchlorates, phosphates, carbonates or bicarbonates; organic carboxylates such as acetates, oxalates, maleates, tartrates or fumarates; organic sulfonates such as methane sulfonates, trifluoromethane sulfonates, ethane sulfonates, benzene sulfonates, toluene sulfonates or camphor sulfonates; amino acid salts such as aspartates or glutamates; salts with amines such as trimethylamine salts, triethylamine salts, procaine salts, pyridine salts or phenethyl benzyl amine salts; alkaline metal salts such as sodium salts or potassium salts; and alkaline earth metal salts such as magnesium salts or calcium salts.

A salt or a hydrates of the compound of the present invention are preferably those pharmaceutically acceptable.

A typical production method of the compound represented by the above formula (I) according to the present invention will be described below. In the present specification, $R^3$ represents the formula —$R^{3a}$–$R^{3b}$ (wherein, $R^{3a}$ and $R^{3b}$ have the same meanings as defined above); and X and $X^a$ are as defined for the above $Q^1$.

Production method A

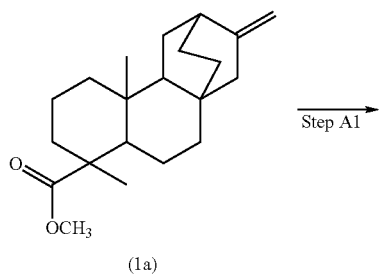
(1a)

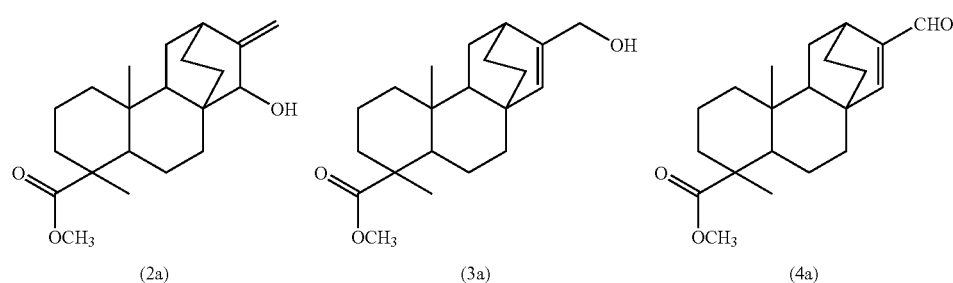
(2a)  (3a)  (4a)

(2a) or (3a) →[Step A2]
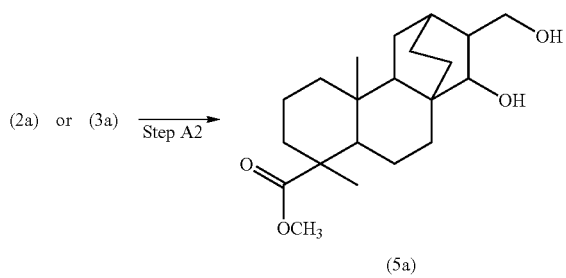
(5a)

(Step A1)

Oxidation step of Compound (1a) (J. Org. Chem., Vol. 36, No. 18, 1971, 2625–2631). By allowing a selenium reagent and Compound (1a) to react with each other, a mixture of Compounds (2a), (3a) and (4a) can be obtained.

As the selenium reagent, selenium dioxide or silica gel bearing selenium dioxide can be used, and selenium dioxide is used in an amount of several equivalents to 0.005 equivalent with respect to raw materials, and a peroxide may be added to the reaction system. Examples of the peroxide include hydrogen peroxide aqueous solution, t-buthylhydroperoxide aqueous solution and the like, and the peroxide is added in an amount of 1 to 5 equivalent(s). As a reaction solvent, methylene chloride, hexane, ethanol, water and the like can be used, and the reaction temperature may be from ice cooling temperature to room temperature.

(Step A2)

Production Step of Compound (5a) Which is an Alcohol from Compound (2a) or (3a) by Means of Hydroboration-Oxidation Method.

Conditions commonly used for conversion from olefin to alcohol by the hydroboration-oxidation method can be used.

Concrete examples of borane reagent for use in the hydroboration include borane-tetrahydrofuran complex, borane-dimethylsulfide complex, 9-borabicyclo[3.3.1]nonane (9-BBN) and the like, and as a reaction solvent for hydroboration, tetrahydrofuran and the like can be used, and the reaction temperature is from 0° C. to heating reflux temperature.

For the oxidation reaction, an oxidizing agent such as hydrogen peroxide aqueous solution is used. During the reaction, an aqueous sodium hydroxide is added. The oxidation reaction is conducted by using an appropriate combination of tetrahydrofuran, water, ethanol and the like as a reaction solvent, and the reaction temperature is from the ice-cooling temperature to room temperature.

Production method B

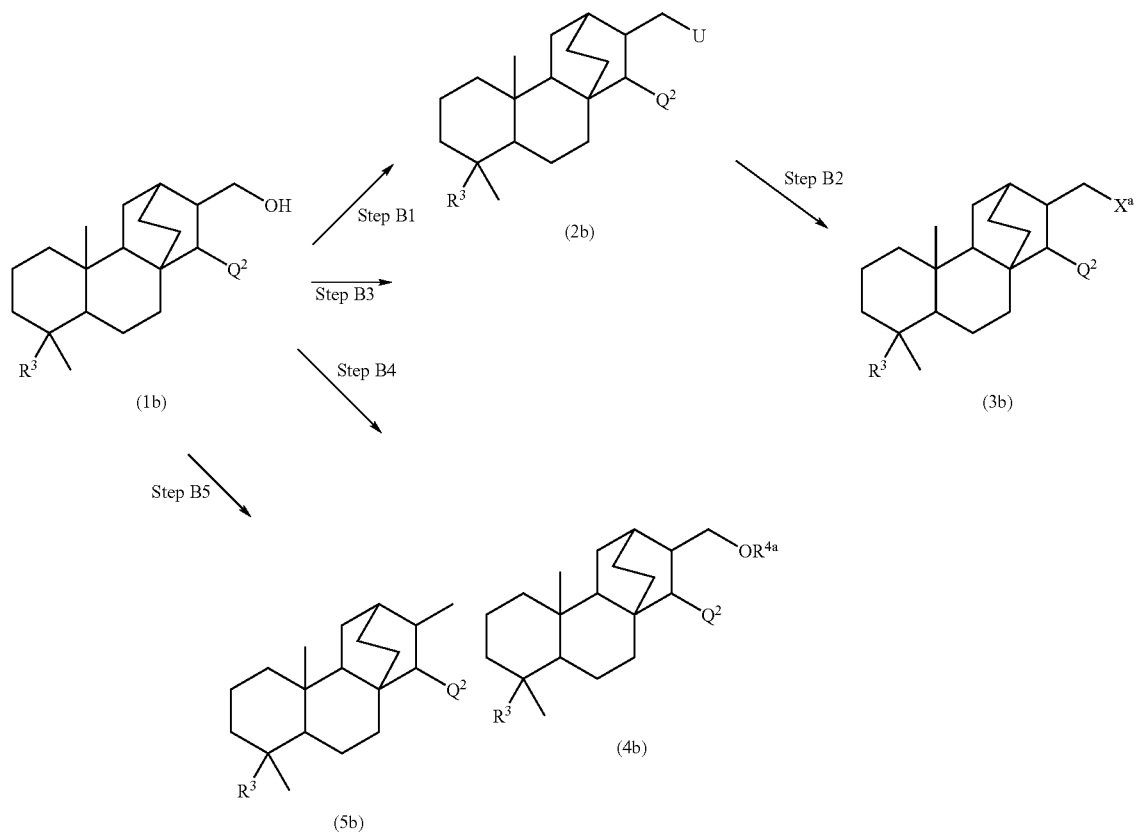

wherein $R^3$, $R^{4a}$, $Q^1$, $Q^2$ and $X^a$ are as defined above; and U represents a halogen atom or sulfonic acid ester group.

As Compound (1b) which is a starting material, compounds which can synthesize the aforementioned Compound (5a) or Compound (5a) by appropriately using the reactions described in Production methods E and F can be used.

(Step B1)

Step of Converting a Hydroxyl Group into a Halogen Atom or a Sulfonic Acid Ester Group such as Methane Sulfonyl Group or p-toluene Sulfonyl Group.

Sulfonic Acid Esterification Reaction

By allowing Compound (1b) and a sulfonic acid esterification reagent to react with each other, Compound (2b) in which U is a sulfonic acid ester group can be obtained.

Examples of the sulfonic acid esterification reagent that can be used include sulfonic halides such as mesyl chloride, tosyl chloride or tosyl fluoride, sulfonic anhydrides such as methanesulfonic anhydride, tosylic anhydride or trifluoromethanesulfonic anhydride and the like. And, it is desirably used in the presence of nitrogen-containing bases such as triethylamine or N-methylmorpholine or pyridine as a base. As the reaction solvent, esters such as acetone or ethyl acetate, ethers such as tetrahydrofuran or t-butyl ether, lower nitriles such as acetonitrile, aprotic solvents such as dimethylformamide, dimethyl sulfoxide or toluene can be usually used. The reaction temperature is from −20° C. to room temperature. Halogenation (chlorination, bromination, iodization) reaction By allowing Compound (1b) and a haloganation reagent to react with each other, Compound (2b) in which U is a halogen atom can be obtained.

In the presence of triphenylphosphine, by reacting a halogenation agent such as carbon tetrachloride, N-chlorosuccinimide, phosphorous oxychloride, thionyl chloride, carbon tetrabromide, N-bromosuccinimide, bromine, phosphorous tribromide, phosphoric bromide or iodine, a halogenated form compound can be obtained. Bases such as triethylamine, imidazole or dimethylaminopyridine may be added to the reaction mixture. The reaction is conducted in an organic solvent such as carbon tetrachloride, dichloromethane, benzene or toluene at a temperature from room temperature to heating reflux temperature.

The halogenated form compound can be obtained by reacting the aforementioned sulfonic acid ester compound such as tosylate or mesylate obtainable from a hydroxyl group by the aforementioned sulfonic acid esterification with lithium chloride, sodium bromide and the like. The reaction is conducted in an organic solvent such as dichloromethane, benzene, toluene or dimethylformamide at a temperature from room temperature to heating reflux temperature.

Fluorination Reaction

By allowing Compound (1b) and a fluorination reagent to react with each other, a fluorinated form compound can be synthesized.

Concrete examples of the fluorination reagent that can be used include diethylaminosulphur trifluoride (DAST), sulphur tetrafluoride, morpholino sulfur trifluoride and the like.

As a reaction solvent, methylene chloride, diglyme, isooctane, monofluorotrichloromethane and the like is used, and the reaction temperature is from −80° C. to room temperature.

(Step B2)

Step of Introducing Various Substituents by Reaction of Compound (2b) with a Nucleophilic Reagent.

As a reaction solvent, tetrahydrofuran, diethyl ether, dimethylformamide, dimethyl sulfoxide, toluene, ethanol and the like can be used, and the reaction temperature is from room temperature to the reflux temperature.

1) Reaction with a nucleophilic reagent selected from alkaline metal salts of alkoxide, alkaline metal salts of thioalkoxide, ammonia, primary amines, secondary amines, lithium cyanide, sodium cyanide, potassium cyanide, tris(dimethylamino)sulfonium difluorotrimethylsilicate (TASF), potassium fluoride, tetrabutylammonium fluoride (TBAF) and the like can afford Compound (3b) in which $X^a$ is a sulfide group, ether group, nitrile group, amino group, fluorine atom or the like.

2) Reaction with a nucleophilic reagent selected from sodium azide, sodium di-t-butylimino dicarboxylate (NaN(Boc)$_2$), sodium phthalimide or the like, followed by reduction, deprotecting and the like reactions, can afford Compound (3b) in which $X^a$ is an amino group.

3) Reaction with a nucleophilic reagent selected from potassium thioacetate (CH$_3$C(O)S—K) and thiourea, followed by an appropriate reaction, can afford Compound (3b) in which $X^a$ is a thiol group.

4) Reaction with a nucleophilic reagent selected from an organic magnesium bromide reagent (Grignard reagent), organic copper reagent and the like can afford Compound (3b) in which $X^a$ in Compound (2b) is an alkyl group, alkynyl group, alkenyl group, phenyl group or the like. Examples of the organic copper reagent include alkyl coppers (RCu), lithium dialkylcuprate (RR'CuLi) and hetero copper complex reagents (R$_2$Cu(CN)Li$_2$).

Copper bromide, copper iodide, copper cyanide and the like may be added to the reaction system.

(Step B3)

Starting from Compound (1b), Mitsunobu reaction and the subsequent deprotecting make it possible to convert Compound (1b) into Compound (3b) in which $X^a$ is an amino group. In the reaction, a phosphine compound and an azodicarboxylate compound are used in combination with an amination reagent.

Examples of the amination reagent include phthalimide. Examples of the phosphine compound include triphenylphosphine and tributylphosphine, and examples of the azodicarboxylate compound include diethyl azodicarboxylate and diisopropyl azodicarboxylate. The reaction is conducted in a solvent such as tetrahydrofuran at room temperature.

(Step B4)

Converting Reaction from a Hydroxyl Group to an Ether Group.

Compound (1b) is reacted with an alkylation reagent (alkyl halide, alkylsulfonic acid ester and the like) in the presence of a base, and thereby Compound (4b) can be obtained. Examples of the base that can be used include calcium carbonate, sodium hydroxide, potassium hydroxide, barium hydroxide, silver oxide and barium oxide. As the reaction solvent, dimethylformamide, ethanol, acetonitrile, benzene and the like can be used, and the reaction temperature is from room temperature to heating reflux temperature.

(Step B5)

Step of Barton Reaction Which is a Dehydroxylation Reaction.

After converting Compound (1b) into a thiocarbonyl derivative, the thiocarbonyl derivative is radical-cleaved, to obtain Compound (5b). Thiocarbonylation can be conducted using a combination of carbon disulfide and methyl iodide, phenyl chlorothioformate, thiocarbonyl imidazole and the like. As the reaction solvent, tetrahydrofuran, acetonitrile, dimethylformamide, 1,2-dichloroethane and the like can be used, and the reaction temperature is from room temperature to heating reflux temperature. The radical cleavage reaction is conducted by allowing hydrogenated trialkyl tin to react in the presence of a radical initiator such as azobisisobutyronitrile. As the reaction solvent, toluene, xylene and the like can be used, and the reaction temperature is from room temperature to heating reflux temperature.

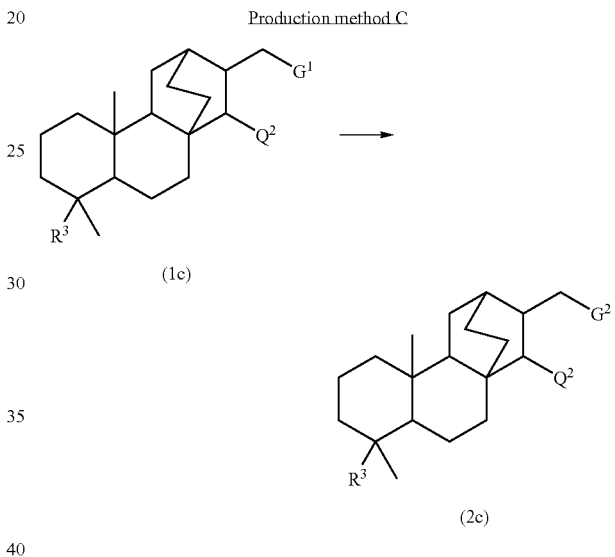

wherein $R^3$ and $Q^2$ are as defined above.

As Compound (1c) which is a starting material, the aforementioned Compound (3b) or a compound that can synthesize the aforementioned Compound (3b) by appropriately using reactions described in the production methods C, D, E and F as necessary can be used.

(C-1) Converting Reaction from Compound (1c) in which $G^1$=—NH$_2$ to Compound (2c) in which $G^2$=—NR$^{4b}$R$^{4c}$ (wherein R$^{4a}$, R$^{4b}$ and R$^{4c}$ are as Defined Above)

1) N-Alkylation Reaction by Nucleophilic Displacement Reaction

By reacting Compound (1c) in which $G^1$ is an amino group with a halogenated alkyl derivative or a sulfonic acid ester derivative, a monoalkylamino group or a dialkylamino group can be obtained.

As the reaction solvent, tetrahydrofuran, diethyl ether, dimethylformamide, dimethyl sulfoxide, toluene, ethanol and the like can be used, and the reaction temperature is from room temperature to heating reflux temperature. In this reaction, bases such as potassium carbonate and sodium carbonate may be added.

2) Reductive N-alkylation Reaction

Compound (1c) in which $G^1$ is an amino group is reacted with a ketone compound such as ketone derivatives and aldehyde derivatives to form an imine form compound, and the imine form compound is then reacted with a reducing agent to obtain an alkylated form compound.

In the imine forming reaction, methanol, ethanol, formic acid, toluene, benzene and the like can be used as the reaction solvents. Further, a dehydrating agent such as sodium sulfate and molecular sieve may added, and a dehydrating apparatus such as Dean-Stark dehydrating apparatus may be attached to conduct the reaction. The reaction temperature is from room temperature to heating reflux temperature.

Reduction reaction of imine form compound is conducted by adding a reducing agent to the reaction solution of the imine forming reaction or to a solution obtainable by distilling off the reaction solution and replacing the solvent with methanol or ethanol. As the reducing agent, sodium borohydride ($NaBH_4$), hydrogenated sodium acetoxyboron ($NaBH(OAc)_3$), hydrogenated sodium cyanoboron ($NaBH_3CN$) or formic acid is used. The reaction temperature is from room temperature to heating reflux temperature. By initially adding the reducing agent, it is possible to simultaneously conduct the imine forming reaction and the reduction of the imine.

(C-2) Synthesis of Amide Derivatives and Sulfonamide Derivatives

By reacting Compound (1c) in which $G^1$ is an amino group with an acid halide, acid anhydride, sulfonyl chloride or carboxylic acid, an amide form compound, sulfonylamide form compound, ester form compound or the like can be obtained.

In the reaction, a condensing agent and a base maybe added. Examples of the condensing agent include N,N'-dicyclohexylcarbodiimide (DCC), 1-ethyl-3-(3'-dimethylaminopropyl)carbodiimide (WSC) and diethyl phosphate cyanide (DEPC).

As the base, dimethylaminopyridine (DMAP), pyridine, diisopropylethylamine, triethylamine and the like, and as the reaction solvent, tetrahydrofuran, acetone, ethyl acetate, dimethylformamide, benzene, dichloromethane and the like can be used. The reaction temperature is from 0° C. to heating reflux temperature, and preferably from 0° C. to room temperature.

(C-3) Converting Reaction from Compound (1c) in which $G^1$=—$SR^{4a}$ to Compound (2c) in which $G^2$=—$S(O)_nR^{4a}$ (wherein $R^{4a}$ is as Defined Above)

Step of oxidizing a sulfide form compound to produce a sulfoxide form compound or a sulfonic form compound. As the oxidizing agent, reagents that are commonly used for oxidization of sulfur atom can be used. Examples of preferred oxidizing agents include sodium periodate, potassium peroxymonosulfate (CAS NO.37222-66-5), camphoursulfonyl oxaziridine (CAS NO.104322-63-6) etc., m-chloroperbenzoic acid and peracetic acid. As the reaction solvent, chloroform, dichloromethane, tetrahydrofuran and the like can be used. The reaction temperature is from 0° C. to room temperature.

(C-4) Converting Reaction from Compound (1c) in which $G^1$=—SH to Compound (2c) in which $G^2$=—$S(O)_2NR^{4b}R^{4c}$ (wherein $R^{4b}$ and $R^{4c}$ are as Defined Above)

Using chlorine and the like, a sulfonyl chloride can be synthesized from a thiol form compound. Preferred reaction solvent is acetic acid, and the reaction is conducted at a temperature from ice-cooling to room temperature.

The sulfonyl chloride thus obtained is reacted with an appropriate amine in pyridine or the like solvent at a temperature from ice-cooling to room temperature, thereby obtaining a sulfonic amide.

(C-5) Converting Reaction from Compound (1c) in which $G^1$=—CN to Compound (2c) in which $G^2$=—$C(O)R^{4a}$ (wherein $R^{4a}$ is as Defined Above)

By reacting Compound (1c) in which $G^1$ is a cyano group with an organic metal reagent such as organic magnesium bromide reagent (Grignard reagent), a ketone form compound can be produced.

As the reaction solvent, diethylether, tetrahydrofuran and the like can be used, and the reaction temperature is from room temperature to heating reflux temperature.

(C-6) Converting Reaction from Compound (1c) in which $G^1$=—CN to Compound (2c) in which $G^2$=—CHO By reducing Compound (1c) in which $G^1$ is a cyano group by diisobutyl aluminum hydride or the like, it is possible to convert the cyano group to a formyl group.

As the reaction solvent, hexane, dichlrormethane, toluene and the like can be used, and the reaction temperature is from −78° C. to room temperature, preferably from −78° C. to 0° C.

(C-7) Converting Reaction from Compound (1c) in which $G^1$=—CN to Compound (2c) in which $G^2$=—$CO_2H$ By hydrolysis of Compound (1c) in which $G^1$ is a cyano group, it can be converted into Compound (2c) in which $G^1$ is a carboxylic group. The reaction is conducted under acidic condition or alkaline condition.

1) Under acidic condition, the reaction is conducted in the presence of concentrated sulfuric acid, diluted sulfuric acid, concentrated hydrochloric acid, diluted hydrochloric acid, acetic acid or formic acid. The reaction temperature is from room temperature to heating reflux temperature.

2) Under alkaline condition, abase such as potassium hydroxide, sodium hydroxide, potassium carbonate, sodium carbonate and the like is used. As the solvent, water, ethanol, tetrahydrofuran, ethylene glycol and the like are used in appropriate combination. The reaction temperature is from room temperature to heating reflux temperature.

(C-8) Converting Reaction from Compound (1c) in which $G^1$=—$CO_2H$ to Compound (2c) in which $G^2$=—$C(O)U^a$ (wherein $U^a$ Represents a Chlorine Atom, Ethoxycarbonyloxy Group or —$N_3$)

1) Acid Halide

By reacting Compound (1c) with a halogenation reagent, it is possible to obtain Compound (2c) in which $G^2$ is a chlorocarbonyl group. As the halogenation reagent, thionyl chloride, oxalyl chloride, phosphorus pentachloride, phosphorus trichloride and the like can be used. The reaction is conducted in the absence of solvent, or in the presence of benzene, dichloromethane, chloroform, dimethylformamide and the like. The reaction is conducted at a temperature from room temperature to heating reflux temperature.

2) Mixed Acid Anhydride

By reacting Compound (1c) with acid chloride such as ethyl chloroformate, it is possible to obtain Compound (2c) in which $G^2$ is an ethoxycarbonyloxy group. As the base, dimethylaminopyridine (DMAP), pyridine, diisopropylethylamine, triethylamine and the like can be used. As the reaction solvent, tetrahydrofuran, acetone, ethyl acetate, dimethylformaide, benzene, dichloromethane and the like can be used. The reaction is conducted at a temperature from −10° C. to room temperature.

3) —$CON_3$

By reacting Compound (1c) with sodium azide, it is possible to obtain Compound (2c) in which $G^2$ is —$CON_3$. An acid halide or a mixed acid anhydride is reacted with sodium azide.

As the reaction solvent, acetone, dimethylformamide, dimethyl sulfoxides and the like can be used, and as the base, triethylamine and the like can be used. The reaction temperature is from −10° C. to room temperature.

(C-9) Converting Reaction from Compound (1c) in which $G^1$=—$CO_2H$ to Compound (2c) in which $G^2$=C(O)$OR^{4a}$, —C(O)$NR^{4b}R^{4c}$ (wherein $R^{4a}$, $R^{4b}$, $R^{4c}$ are as Defined Above)

By reacting Compound (1c) which is an acid halide, mixed acid anhydride or a carboxylic acid with an amine or an alcohol, an amide form compound or an ester form compound can be obtained.

In the reaction, a condensing agent or a base may be added. Examples of the condensing agent include N,N'-dicyclohexylcarbodiimide (DCC), 1-ethyl-3-(3'dimethylaminopropyl)carbodiimide (WSC) and diethyl phosphate cyanide (DEPC).

As the base, dimethylaminopyridine (DMAP), pyridine, diisopropylethylamine, triethylamine and the like can be used, and as the reaction solvent, tetrahydrofuran, acetone, ethyl acetate, dimethylformamide, benzene, dichloromethane and the like can be used. The reaction temperature is from 0° C. to heating reflux temperature, preferably from 0° C. to room temperature.

(C-10) Converting Reaction from Compound (1c) in which $G^1$ is —$CONH_2$ to Compound (2c) in which $G^2$ is —CN By reacting Compound (1c) in which $G^1$ is —$CONH_2$ with a dehydrating agent, it is possible to produce Compound (2c) in which $G^2$ is a cyano group.

As the dehydrating agent, diphosphorus pentaoxide ($P_2O_5$), phosphorus pentachloride, thionylchloride and the like can be used. The reaction may be conducted in the absence of solvent, or in the presence of benzene, chlorobenzene and the like solvent. The reaction temperature is from room temperature to heating reflux temperature.

(C-11) Converting Reaction from Compound (1c) in which $G^1$=—$CO_2H$ to Compound (2c) in which $G^2$=—$NH_2$ By Schmidt rearrangement reaction or Lossen rearrangement reaction of Compound (1c) in which $G^1$ is a carboxylic group or Hofmann rearrangement reaction of Compound (1c) in which $G^1$ is —$CONH_2$, it is possible to obtain Compound (2c) in which $G^2$ is an amino group.

By Curtius rearrangement reaction of Compound (1c) in which $G^1$ is —$CON_3$ or a carboxylic group, it is possible to obtain Compound (2c) in which $G^2$ is an amino group.

1) By hydrolysis or deprotecting reaction after heating Compound (1c) in which $G^1$ is —$CON_3$ at a reaction temperature in the range of 50 to 120° C., preferably in the range of 70 to 90° C., it is possible to obtain an amine form compound. As the solvent, benzene, toluene, t-butanol, benzylalcohol and the like can be used. The hydrolysis reaction is conducted at a temperature of 50 to 120° C. in the presence of an acid such as hydrochloric acid. The deprotecting reaction can be conducted in a commonly used method for elimination reaction of t-butoxycarbonyl group and benzyloxycarbonyl group.

2) In the case where $G^1$ is a carboxylic group, the reaction is conducted in benzene or t-butanol in the presence of diphenyl azidophosphate and a base. The reaction temperature is from 50° C. to heating reflux temperature, and preferably from 70 to 90° C. Thereafter as described in the above (C-9), hydrolysis or deprotecting reaction is conducted in appropriate to obtain an amine form compound.

(C-12) Converting Reaction from Compound (1c) in which $G^1$=—$CO_2R^{4a}$ to Compound (2c) in which $G^2$=—$CH_2OH$ (wherein $R^{4a}$ is as Defined Above)

By reduction reaction of Compound (1c) in which $G^1$ is a carboxylic group or an ester group, it is possible to convert the carboxylic group in Compound (1c) into a hydroxymethyl group. The reducing agent to be used is reagents commonly used for reduction of carboxylic acid and ester such as lithium aluminum hydride and borane. As the reaction solvent, tetrahydrofuran, diethylether or the like is used, and the reaction temperature is from room temperature to heating reflux temperature.

(C-13) Converting Reaction from Compound (1c) in which $G^1$=—$CH_2OH$ to Compound (2c) in which $G^2$=—$CH_2X$ (wherein X is as Defined Above)

To Compound (1c) in which $G^1$ is a hydroxymethyl group, various substituents can be introduced under the similar condition in each reaction described in the production method B or C.

(C-14) Converting Reaction from Compound (1c) in which $G^1$=—$CH_2CN$ to Compound (2c) in which $G^2$=—$CH_2COR^{4a}$ (wherein $R^{4a}$ is as Defined Above)

As for Compound (1c) in which $G^1$ is a cyanomethyl group, the cyano group in Compound (1c) can be converted into a ketone group, formyl group, carboxylic group, ester group or amide group in the similar conditions described in the above (C-5) to (C-9).

(C-15) Converting Reaction from Compound (1c) in which $G^1$=—$COU^b$ to Compound (2c) in which $G^2$=—$CH_2CO_2R^{4a}$ (wherein $U^b$ Represents a Leaving Group such as a Chlorine Atom or an Acyloxy Group, and $R^{4a}$ is as Defined Above)

The reaction condition is as same as that generally used in Wolff rearrangement reaction.

1) Converting Reaction from Compound (1c) in which $G^1$=—$COU^b$ to Compound (2c) in which $G^2$=—$COCH_2N_2$ By reacting Compound (1c) in which $G^1$ is an acid halide or an acid anhydride with diazomethane or trimethylsilyl diazomethane, it is possible to obtain Compound (2c) in which $G^2$ is —$COCH_2N_2$. In the reaction, tertiary amines such as triethylamine is added. As the reaction solvent, diethylether, tetrahydrofuran and the like can be used, and the reaction temperature is in the range of −30° C. to 0° C.

2) Rearrangement Reaction

By reacting Compound (1c) in which $G^1$ is —$COCH_2N_2$ with a rearrangement reaction catalyst, it is possible to obtain a carboxylic acid or an ester form compound in which $G^2$ is —$CH_2COOR^{4a}$. In the reaction, a base such as triethylamine and sodium carbonate may be added. As the rearrangement reaction catalyst, silver oxide, silver benzoate and sodium thiosulfate are used in appropriate combination. As the reaction solvent, water, ethanol, dioxane and the like can be used, and the reaction temperature is from 0° C. to heating reflux temperature.

(C-16) Converting Reaction from Compound (1c) in which $G^1$=—$CH_2OH$ to Compound (2c) in which $G^2$=—CHO Oxidation step from a hydroxyl group to a carbonyl group.

As the oxidizing agent to be used, manganese dioxide, oxidizing agent generally used in Swan oxidation, and reagents which are used in usual alcohol oxidation such as pyridinium chlorochromate, tetrapropyl ammonium perruthenate and sodium bromate-sodium hydrogensulfite are preferred.

As the reaction solvent, dichloromethane, toluene, benzene and the like can be used. The reaction temperature is from −78° C. to heating reflux temperature, and preferably in the range of −78° C. to 0° C.

(C-17) Converting Reaction from Compound (1c) in which $G^1$=—CHO to Compound (2c) in which $G^2$=—$CH_3$ By Wolff-Kishner reduction, Compound (2c) in which $G^2$=—$CH_3$ can be synthesized. As a reagent, a combination of hydrazine and sodium hydroxide can be used, and the reaction is conducted in a solvent such as diethylene glycol at heating reflux temperature.

(C-18) Converting Reaction to Alkenes or Alkynes of Aldehyde

Step of Horner-Emmons reaction or Wittig reaction. By reacting Compound (1c) in which $G^1$ is a formyl group with a Horner-Emmons reagent or a Wittig reagent, it is possible to obtain an alkene or an alkyne. In the reaction, a base such as sodium hydroxide, triethylamine, sodium ethoxide, n-butyl lithium, methyl lithium, lithium diisopropylamide (LDA), sodium hydride, potassium-t-butoxide, lithium bistrimethylsilyl amide, sodium bistrimethylsilyl amide, lithium 2,2,6,6-tetramethylpiperido (LTMP) or the like is added.

As the Horner-Emmons reagent or the Wittig reagent, triphenylphosphonium derivatives or phosphonic acid derivatives are used. More specifically, it means reagents represented by the following formula:

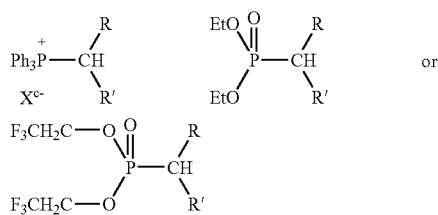

where in R and R' are independent of each other and each represents a hydrogen atom, a halogen atom or a substituent having the same meaning as $Q^2$; and $X^c$ represents a halogen atom. As the reaction solvent, tetrahydrofuran, ethanol, diethylether, dimethyl sulfoxides and the like can be used. The reaction temperature is from −78° C. to 50° C.

(C-19) Reduction Reaction of Compound (1c) in which $G^1$ is an Alkenyl Group or an Alkynyl Group Catalytic reduction step of alkenes and alkynes.

The reaction is conducted in a hydrogen atmosphere at one to several atmosphere(s). As the catalyst, platinum dioxide ($PtO_2$), palladium-carbon (Pd—C) and the like can be used. As the reaction solvent, ethanol, t-butanol, acetic acid ester, acetic acid or the like is used. The reaction temperature is from room temperature to 50° C.

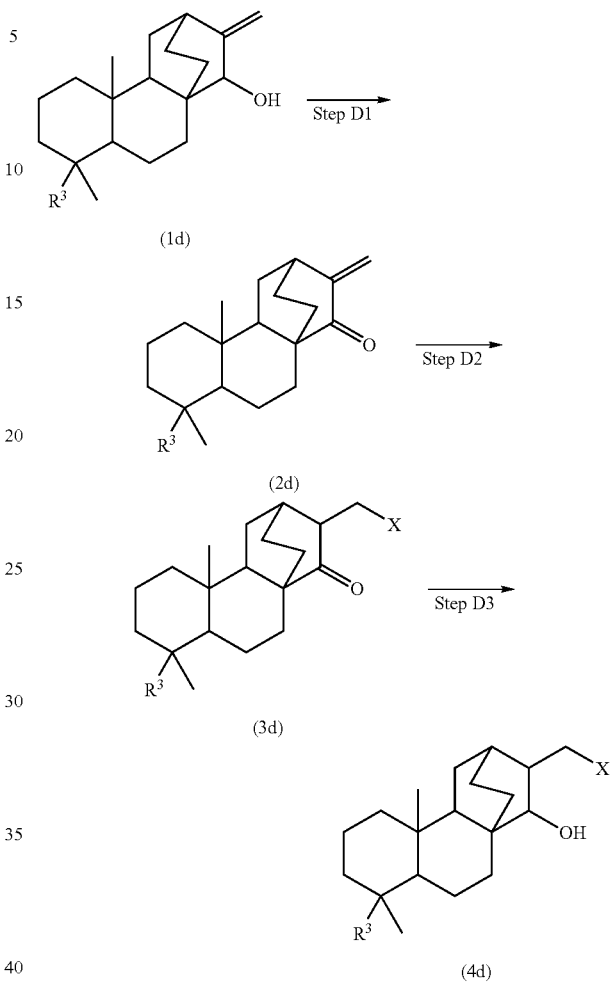

Production method D wherein X and $R^3$ are as defined above.

As Compound (1d) which is a starting material, the aforementioned Compound (2a) or a compound that can synthesize the aforementioned Compound (2a) by appropriately using reactions described in the production method F as necessary can be used.

(Step D1)

Oxidation step from a hydroxyl group to a carbonyl group. Compound (2d) can be obtained in the similar condition as in the above (C-16).

(Step D2)

Step of Michael addition reaction which is a nucleophilic reagent addition reaction to an α,β-unsaturated ketone. By making a nucleophilic reagent react on Compound (2d), it is possible to obtain Compound (3d). As the nucleophilic reagent, the nucleophilic reagents recited in the Production method B can be used, for example.

As the reaction solvent, benzene, tetrahydrofuran, acetonitrile, dimethylformamide, dimethyl sulfoxide, ethanol and the like can be used. The reaction temperature is from room temperature to heating reflux temperature.

(Step D3)

Reduction step from a carbonyl group to a hydroxyl group. By reacting Compound (3d) with a reducing agent, it is possible to obtain Compound (4d). The reducing agent to be used is a reducing agent commonly used in reduction of ketone, and sodium borohydride, lithium aluminum hydride and the like can be exemplified.

As the reaction solvent, diethylether, tetrahydrofuran, ethanol, methanol and the like can be used. The reaction temperature is from room temperature to heating reflux temperature.

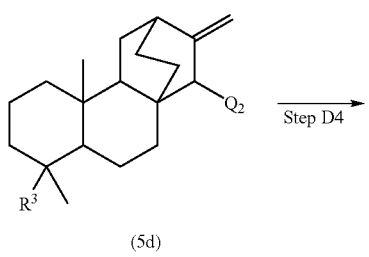

(5d)

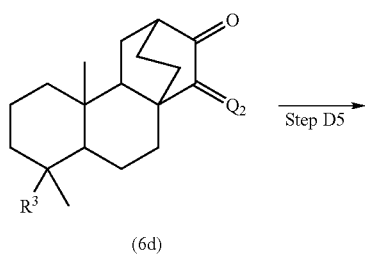

(6d)

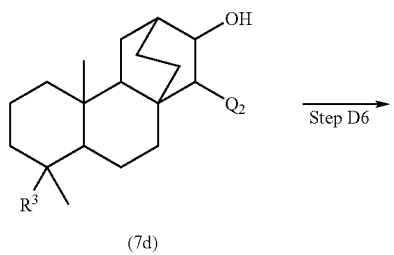

(7d)

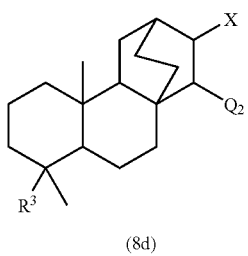

(8d)

wherein X, $R^3$ and $Q^2$ are as defined above.

As Compound (5d) which is a starting material, the aforementioned Compound (2a) or a compound that can synthesize the aforementioned Compound (2a) by appropriately using reactions described in the production methods E and F as necessary can be used.

(Step D4)

Step of obtaining Compound (6d) by oxidation cleavage reaction of Compound (5d). As the oxidation cleavage reaction, (1) ozone oxidation reaction or (2) osmium oxidation-decomposition reaction is recited.

1) Ozone Oxidation Reaction

After allowing Compound (5d) to react under oxygen gas flow containing several % of ozone, an oxidative process or a reductive process is conducted to obtain Compound (6d). As the reaction solvent, dichloromethane, ethyl acetate, methanol and the like can be used, and the reaction is conducted at a temperature from −78° C. to room temperature. Following the ozone oxidation reaction, nitrogen displacement, removal of solvent by distillation, addition of solvent and the like are conducted appropriately without isolating the generated ozonide. Then an oxidizing agent or a reducing agent is added to the reaction mixture to allow reaction, thereby obtaining Compound (6d).

In the case of the oxidative process, hydrogen peroxide, chromic acid-sulfuric acid or the like is used as the oxidizing agent. As the reaction solvent, sulfuric acid, acetic acid or the like is used. The reaction temperature is from room temperature to the reflux temperature.

In the case of the reductive process, dimethylsulfide, zinc-acetic acid, triethylphosphite or the like is used as the reducing agent. The reaction temperature is from −78° C. to room temperature.

2) Osmium Oxidation-Decomposition Reaction

By subjecting Compound (5d) to a decomposition reaction by an oxidizing agent after completion of an osmium oxidation, it is possible to obtain Compound (6d).

As the oxidizing agent for the osmium oxidation, 1 to 0.1 equivalent of osmium oxide ($OsO_4$) is used. During the osmium oxidation reaction, as a reoxidizing agent, N-methylmorpholine N-oxide or triethylamine oxide may be added to the reaction. As the reaction solvent, acetonitrile, water, acetone and t-butyl alcohol are used in appropriate combination. The reaction temperature is from 0° C. to room temperature.

As the oxidizing agent for decomposition, sodium periodate, potassium periodate or lead tetraacetate can be used. As the reaction solvent, benzene, diethylether, water, acetic acid and the like are used in appropriate combination. The reaction temperature is from 0° C. to room temperature. In the reaction, a base such as potassium carbonate may be added.

(Step D5)

Reduction step from a carbonyl group to a hydroxyl group. By reacting Compound (6d) which is similar to the above (D-3) with a reducing agent, it is possible to obtain Compound (7d). Examples of the reducing agent to be used is reducing agents used in usual ketone reduction, such as sodium borohydride, lithium aluminum hydride and the like.

(Step D6)

To Compound (1c) in which $G^1$ is a hydroxymethyl group, various substituents can be introduced in the condition similar to that of each reaction described in the above Production method B or C.

Production method E

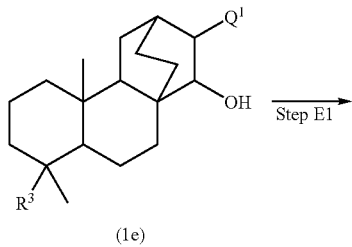
(1e)

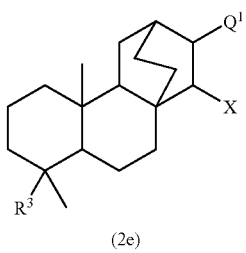
(2e)

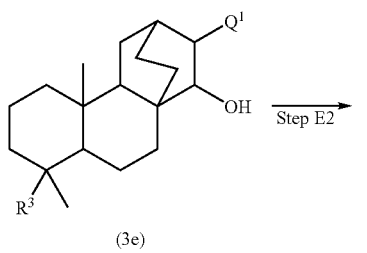
(3e)

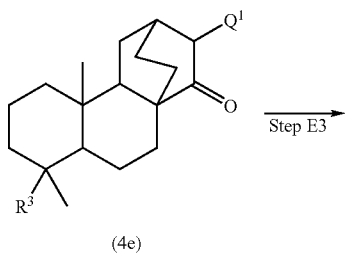
(4e)

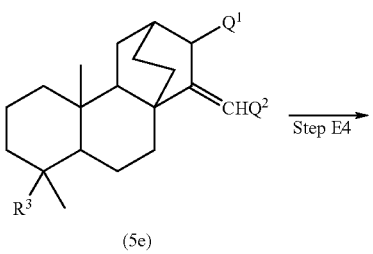
(5e)

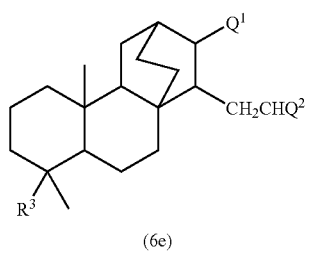
(6e)

wherein X, $R^3$, $Q^1$ and $Q^2$ are as defined above.

As Compound (1e) which is a starting material, the aforementioned Compound (5a) or a compound that can synthesize the aforementioned Compound (5a) by appropriately using reactions described in the production methods B, C, D and F as necessary can be used.

(Step E1)
Using a condition similar to that of each reaction described in the above Production method B or C, it is possible to obtain Compound (2e).

(Step E2)
Using a condition similar to that of the Production method D1, it is possible to obtain Compound (4e).

(Step E3)
Using a condition similar to that described in (C-18), it is possible to obtain Compound (5e) from Compound (4e).

(Step E4)
Using a condition similar to that described in (C-19), it is possible to obtain Compound (6e) from Compound (5e).

Production method E-2

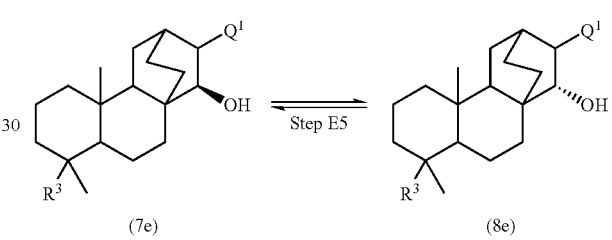

(7e)      (8e)

wherein $R^3$ and $Q^1$ are as defined above.

As Compound (7e) and Compound (8e), the aforementioned Compound (5a) or a compound that can synthesize the aforementioned Compound (5a) by appropriately using reactions described in the production methods B, C, D and F as necessary can be used.

(Step E5)
Inversion of configuration of a hydroxyl group. By reducing Compound (7e) following Mitsunobu reaction or alcohol oxidation, it is possible to obtain Compound (8e), and also it is possible to obtain Compound (7e) from Compound (8e) in the same manner.

1) In the Mitsunobu reaction, a combination of phosphine compound, azodicarboxylate compound and nucleophilic reagent is used. Examples of the phosphine compound include triphenylphosphine and tributylphosphine, and examples of the azodicarboxylate compound include diethylazodicarboxylate and diisopropylazodicarboxylate. Examples of the nucleophilic reagent include formic acid and benzoic acid. The reaction is conducted in a solvent such as tetrahydrofuran at room temperature.

2) Concrete examples of the reagents used in the oxidation reaction include, Swan oxidation, sodium hypochlorite, sodium bromate-sodium hydrogensulfite, tetrapropyl ammonium perruthenate and the like.

As the reagent to be used in the subsequent reduction reaction, for example, sodium triacetoxy borohydride, tetramethyl ammonium triacetoxy borohydride and sodium borohydride can be recited.

Production method F
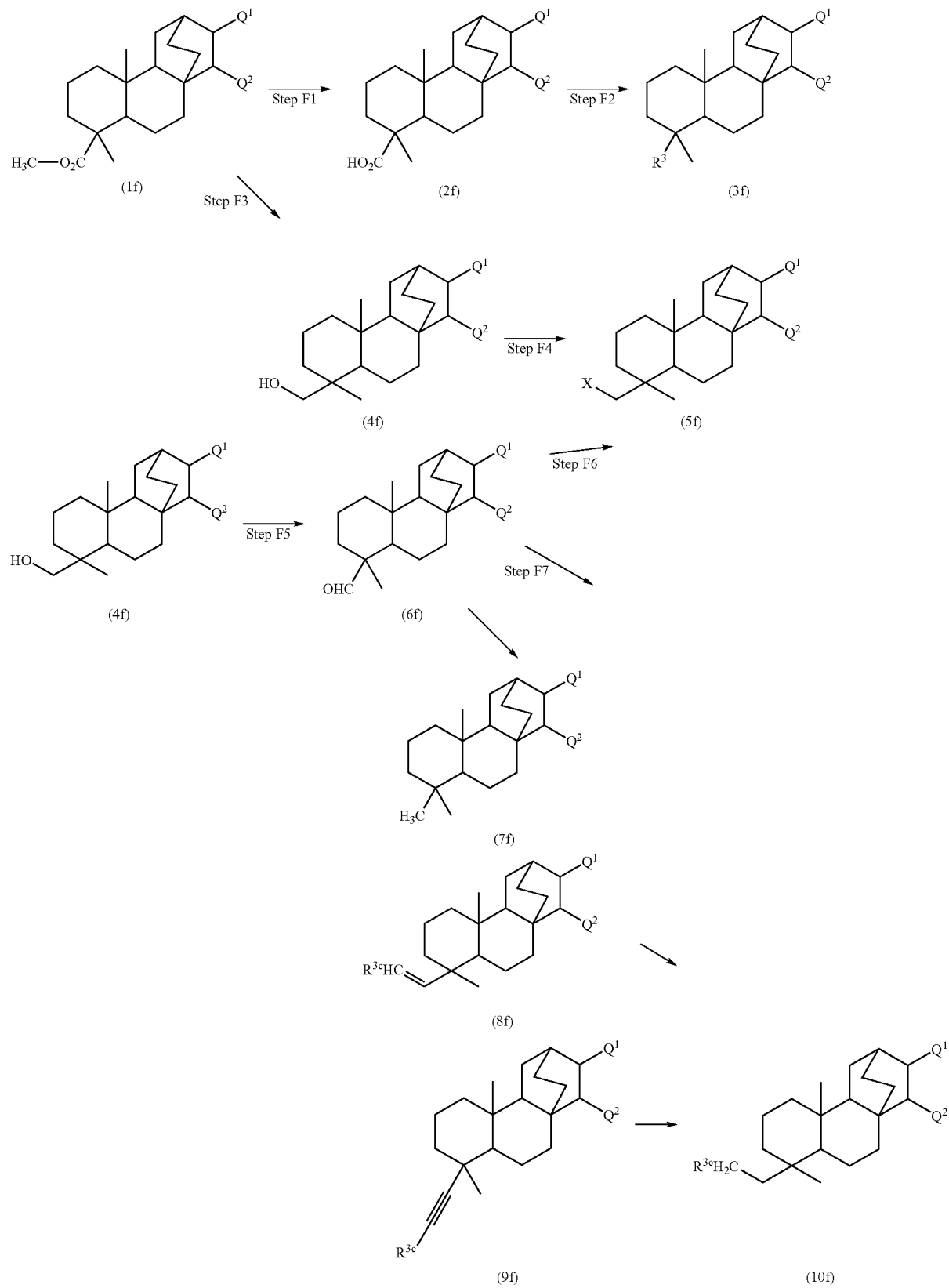

where in X, R³, Q¹, Q² and R are as defined above, and $X^b$ represents a cyano group, amide group, amino group, acylamino group, sulfonyl amino group or the like. $R^{3c}$ represents a substituent having the same meaning as Q².

As Compound (1f) which is a starting material, the aforementioned Compound (5a) or a compound that can synthesize the aforementioned Compound (5a) by appropriately using reactions described in the production methods B, C, D and E as necessary can be used.

(Step F1)

Hydrolysis reaction step from ester to carboxylic acid. Conditions that are used in usual ester hydrolysis can be employed.

Specifically, by reacting a nucleophilic reagent such as alkaline metal salts of alkylthiol, lithium iodide, lithium bromide, lithium cyanide, sodium cyanide or potassium cyanide on Compound (1f), it is possible to obtain Compound (2f). As the reaction solvent, 1-methyl-2-pyrrolizinone (NMP), dimethylformamide, pyridine, collidine, hexamethylphosphoramide (HMPA) and the like can be used.

As the alkaline metal slats of alkylthiol, sodium thiomethoxide, sodium thioethoxide, sodium thiopropoxide, lithium thiomethoxide, lithium thioethoxide, lithium thiopropoxide, and the like can be exemplified. The reaction temperature is from room temperature to the reflux temperature.

(Step F2)

Using the similar conditions to those in the methods described in the above (C-1), (C-2), (C-8) to (C-11), Compound (3f) can be obtained from Compound (2f).

(Step F3)

Using a condition similar to that of the above (C-12), Compound (4f) can be obtained from Compound (1f).

(Step F4)

Using a condition similar to that of the above (C-13), Compound (5f) can be obtained from Compound (4f).

(Step F5)

Using a condition similar to that of the above (C-16), Compound (6f) can be obtained from Compound (4f).

(Step F6)

Using a condition similar to that of the above (C-17), Compound (7f) can be obtained from Compound (6f).

(Step F7)

Using a condition similar to that of the above (C-18), Compound (8f) or Compound (9f) can be obtained from Compound (6f).

(Step F8)

Using a condition similar to that of the above (C-19), Compound (10f) can be obtained from Compound (8f) or Compound (9f).

Production method G

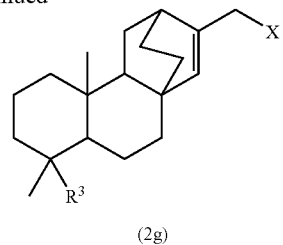

(Step G1)

Using a condition similar to that of each reaction described in the above Production method B or C, Compound (2g) can be obtained from Compound (1g).

wherein X and R³ are as defined above.

(Step G2)

Step of brominating reaction of Compound (3g) or Compound (4g) to obtain Compound (5g). As the brominating reagent, N-bromosuccinimide and the like can be used.

In the reaction, benzoyl peroxide, azobisisobutyronitrile (AIBN) and the like may be added at 0.1 to 3% amousnt. As the reaction solvent, carbon tetrachloride, cyclohexane, benzene and the like is used. The reaction temperature is in the range of 0 to 100° C. The reaction may be achieved by ultraviolet irradiation.

(Step G3)

Using the similar condition of each reaction described in the above Production method B or C, Compound (6g) can be obtained from Compound (5g).

(Step G4)

Using the similar condition of each reaction described in the above Production method F, Compound (7g) can be obtained from Compound (6g).

By appropriately using the reaction conditions described in the above Production methods A to G and using as a starting material Compounds represented by the formulae:

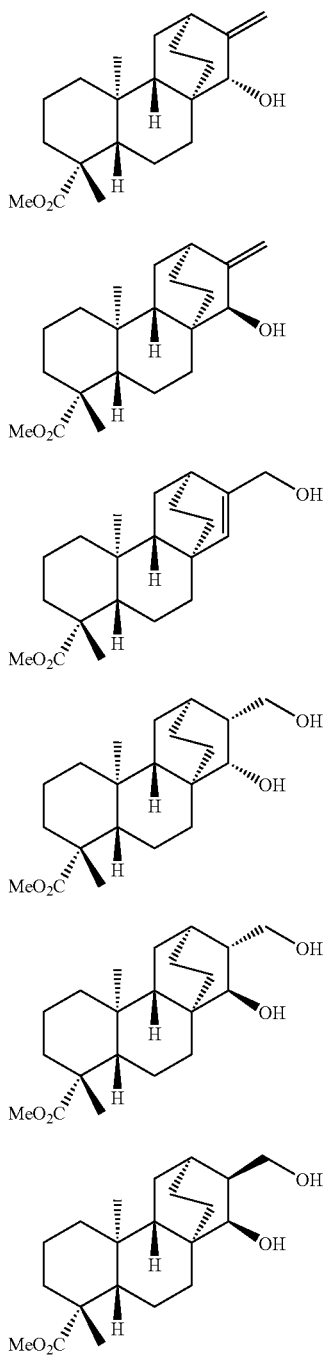

described in Example 1 ((S1-1), (S1-2), (S1-3)), Example 2, Example 3 or Example 70, Compound represented by the above formula (Ia) according to the present invention can be produced.

Various isomers that are obtainable for Compound represented by the above formula (I) can be purified and isolated by means of usual separation means (for example, recrystallization and chromatography).

The term "skin disease" used in the present description includes atopic dermatitis, contact dermatitis and hyperesthesia.

The term "neurological disorder" used in the present description include acute neurodegenerative diseases such as disorder by cerebral ischemia, subarachnoid hemorrhage, cerebrovascular disorder acute stage, head injury, spinal cord injury, or neuropathy due to hypoxia or hypoglycemia, chronic neurodegenerative diseases such as Alzheimer disease, Parkinson disease, Huntington chorea, amyotrophic lateral sclerosis (ALS), multiple sclerosis or spinocerebellar degeneration, chronic intractable disease, epilepsy, hepatic encephalopathy, peripheral neuropathy, Parkinson syndrome, spastic paralysis, pain, neuralgia, anxiety, drug dependence, nausea, vomiting, urination disorder, visual disorder due to glaucoma, retinopathy of prematurity, diabetic retinopathy, macular degeneration, hearing disorder by antibiotics, food poisoning and the like.

The compound according to the present invention, a salt thereof or a hydrate of them can be prepared in the forms of tablet, powder, fine granule, granule, coating tablet, capsule, syrup, troche, inhalant, suppository, injection, ointment, eye ointment, eye drop, nasal drop, ear drops, cataplasm, lotion agent and the like by means of commonly used methods. In preparation, generally used filler, binder, lubricant, colorant, flavoring agent, as well as stabilizer, emulsifying agent, absorption promoter, surfactant, pH adjusting agent, preservative, anti-oxidant and the like can be used as necessary, and preparation is achieved by means of conventional methods while blending components that are generally used as raw materials of pharmaceutical formulation. For example, in preparing oral formulations, after blending the compound according to the present invention or a pharmaceutically acceptable salt thereof and a filler, as well as a binder, disintegrating agent, lubricant, colorant, flavoring agent and the like as necessary, the mixture is formed into powder, fine granule, granule, tablet, coating tablet, capsule and the like in a conventional method. Examples of the above components include animal and vegetable oils such as soybean oil, beef tallow or synthesis glyceride; hydrocarbons such as liquid paraffin, squalane or solid paraffin; ester oils such as octyldodecyl myristate or isopropyl myristate; higher alcohols such as ceto-stearyl alcohol or behenyl alcohol; silicon resin; silicon oil; surfactants such as polyoxyethylene fatty acid esters, sorbitan fatty acid esters, glycerine fatty acid esters, polyoxyethylene sorbitan fatty acid esters, polyoxyethylene hardened castor oil or polyoxyethylene-polyoxypropylene block copolymer; water-soluble polymers such as hydroxyethyl cellulose, polyacrylic acid, carboxy vinyl polymer, polyethylene glycol, polyvinylpyrrolidone or methyl cellulose; lower alcohols such as ethanol or isopropanol; polyhydric alcohols such as glycerin, propylene glycol, dipropylene glycol or sorbitol; sugars such as glucose or sucrose; inorganic powders such as silicic anhydride, aluminum silicate magnesium or aluminum silicate; and purified water. Examples of the filler include lactose, corn starch, saccharose, glucose, mannitol, sorbit, crystalline cellulose or silicon dioxide; examples of the binder include polyvinyl alcohol, polyvinyl ether, methyl cellulose, ethyl cellulose, gumarabic, gum tragacanth, gelatine, shellac, hydroxypropylmethyl cellulose, hydroxypropyl cellulose, polyvinylpyrrolidone, polypropylene glycol-polyoxyethylene block polymer or meglumine; examples of the disintegrating agent include starch, agar, gelatin, crystalline cellulose, calcium carbonate, sodium hydrogen carbonate, calcium citrate, dextrin, pectin or carboxymethyl cellulose calcium; examples of the lubricant include magnesium stearate, talc, polyethylene glycol, silica or hydrogenated vegetable oil; examples of the colorant include those accepted to be added to pharmaceuticals; and examples of the flavoring agent include cocoa powder, menthol, aromatic powder, mentha oil, borneol and cinnamon powder. It goes without saying that these tablets and granules maybe appropriately coated with sugar, etc., if necessary. Liquid agents such as syrup or injection formulation may produced by blending the compound according to the present invention or a pharmaceutically acceptable salt thereof with pH regulating agents, a solubilizer, an isotonizing agent, etc., optionally together with solubilizing aids, stabilizers, etc. and processing the resultant blends into preparations by the conventional methods. External preparations may be produced by the conventional methods without restriction. As the bases, therefore, use can be made of various materials commonly used in drugs, quasi drugs, cosmetics, etc. Particular examples of the base materials include animal and vegetable oils, mineral oils, ester oils, waxes, higher alcohols, fatty acids, silicone oils, surfactants, phospholipids, alcohols, polyhydric alcohols, water-soluble polymers, clay minerals and purified water. If needed, it is possible to further add pH adjusting agents, antioxidants, chelating agents, antiseptics, fungicides, coloring agents, perfumes, etc., though the materials usable as the base in the external preparations of the present invention are not restricted thereto. If necessary, it is also possible to furthermore add other ingredients such as a component having a differentiation-inducing action, blood flow promoter, bactericide, anti-inflammatory agent, cell activator, vitamins, amino acid, moisturizer or keratin solubilizing agent. The above materials may be added in such amounts as to give the concentrations thereof commonly employed in the production of external preparations.

In administering the compound according to the present invention, a salt thereof or a hydrate of them, the dosage form is not particularly limited, and they may be administered orally or parenterally by conventionally used manners. They may be formulated and administered in the form of, for example, tablet, powder, granule, capsule, syrup, troche, inhalant, suppository, injection, ointment, eye ointment, eye drop, nasal drop, ear drop, cataplasm, lotion and the like. The dosage amount of the pharmaceutical according to the present invention can be appropriately selected in accordance with severity of symptom, age, sex, bodyweight, dosage form, type of the salt, particular type of the disease.

The dosage varies greatly depending on the kind of disease and the severity of symptom, age, sex and sensitivity to drug of the patient, and generally, these compounds are administered to an adult in a dose of about 0.03 to 1000 mg, preferably from 0.1 to 500 mg and still preferably from 0.1 to 100 mg, per day once or several times a day. In the case of injection, generally about 1 µg/kg to 3000 µg/kg, and preferably about 3 µg/kg to 1000 µg/kg is administered.

In the present description, "Me" denotes a methyl group, "Ph" denotes a phenyl group, "Ts" denotes a p-toluenesulfonyl group, "Ms" denotes a methanesulfonyl group, "Ac" denotes an acetyl group, "Boc" denotes a t-butoxycarbonyl group, and "MOM" denotes a methoxymethyl group.

The present invention can provide a novel compound which exhibits a protective effect against cell injury due to radical while exhibiting an excellent nerve protective effect by efficiently suppressing neurotoxicity induced by excitatory neurotransmitters. The compound of the present invention represented by the above formula (I) is particularly useful as an agent for treating or preventing a disease to which glutamate-induced neurotoxicity relates and a disease to which NO-induced neurotoxicity relates, and is useful as an agent for treating or preventing, for exmaple, acute neurodegenerative diseases such as subarachnoid hemorrhage, cerebrovascular disorder acute stage, head injury, disorder by cerebral ischemia, spinal cord injury, or neuropathy due to hypoxia or hypoglycemia, chronic neurodegenerative diseases such as Alzheimer disease, Parkinson disease, Huntington chorea, amyotrophic lateral sclerosis (ALS), multiple sclerosis or spinocerebellar degeneration, chronic intractable disease, epilepsy, hepatic encephalopathy, peripheral neuropathy, Parkinson syndrome, spastic paralysis, pain, neuralgia, anxiety, drug dependence, nausea, vomiting, urination disorder, visual disorder due to glaucoma, retinopathy of prematurity, diabetic retinopathy, macular degeneration, hearing disorder by antibiotics, food poisoning and various skin diseases.

EXAMPLES

Figure 1:
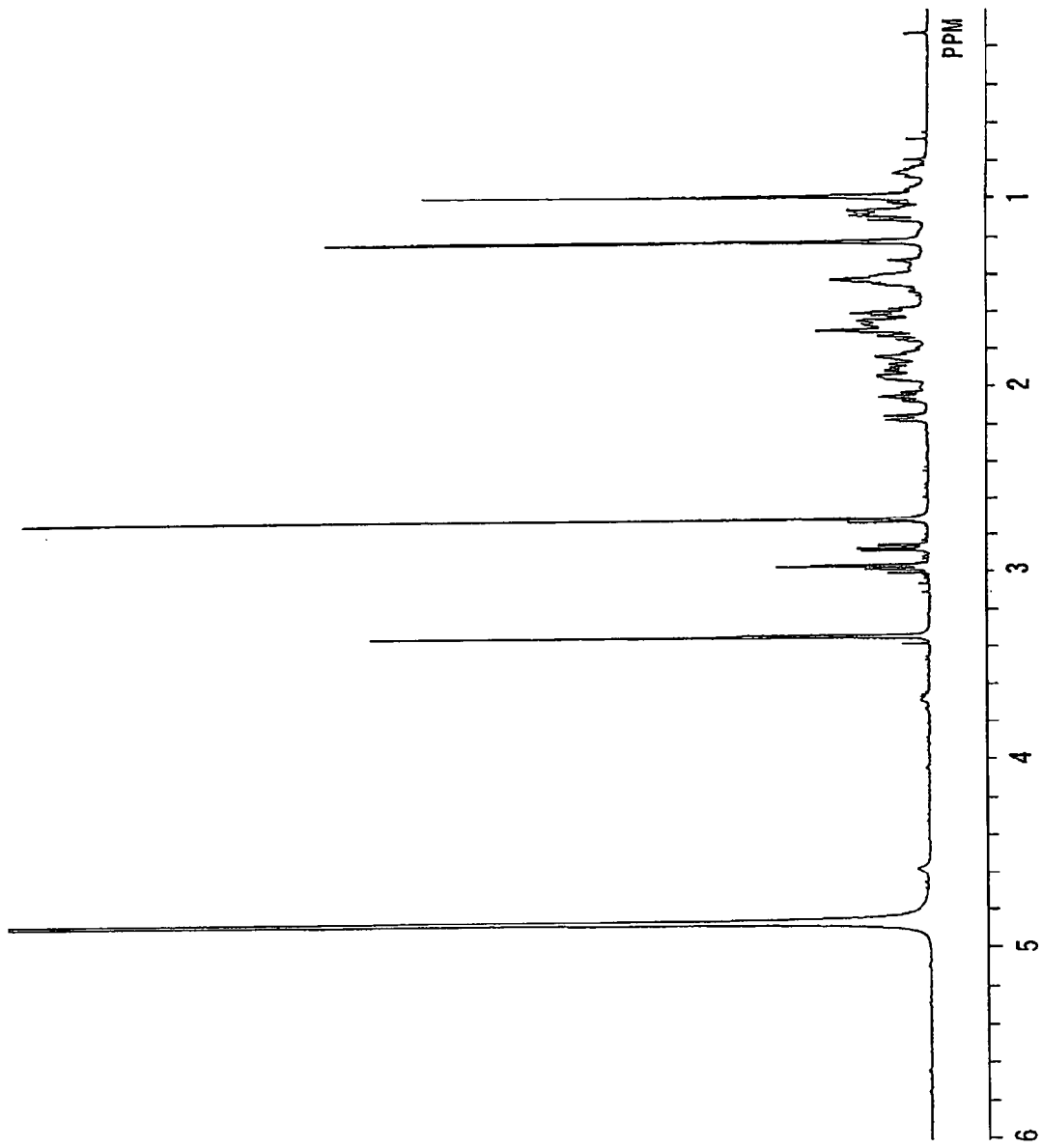
FIG. 1 is a view showing the proton NMR spectrum (500 MHz: δppm in $CD_3OD$) of the substance obtained in Example 6 (Serofendic acid A (isomer 1)).

Compounds according to the present invention can be produced by the methods described in the following Examples. However, these Examples are given exemplification, and the compounds according to the present invention are not anyway limited to these concrete examples.

Example 1

Methyl ent-15α-hydroxy-16-atisene-19-oate (S1-1)

Methyl ent-15β-hydroxy-16-atisene-19-oate (S1-2)

Methyl ent-17-hydroxy-15-atisene-19-oate (S1-3)

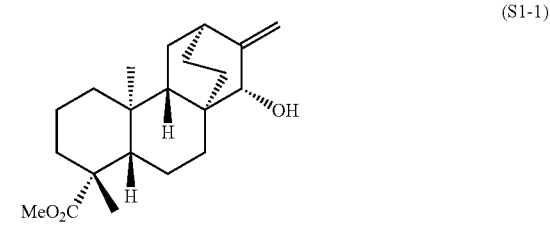

(S1-1)

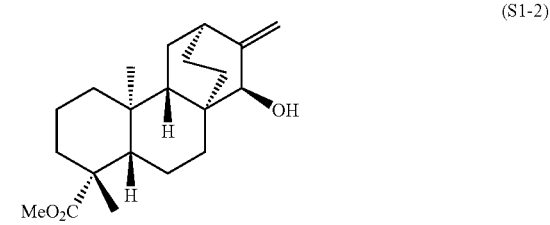

(S1-2)

-continued (S1-3)
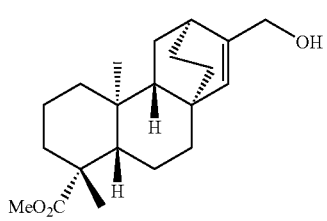

To a solution of silica gel bearing selenium dioxide (4.76%) (0.86 g, 0.369 mmol) in dichloromethane (21.2 mL) was added a 70% aqueous t-butyl hydroperoxide (0.44 mL, 3.18 mmol) was added at room temperature under stirring, followed by stirring at room temperature for 20 minutes. A 10 mL solution of an approx. 4:1 mixture (336 mg, 1.06 mmol) of methyl ent-16-atisene-19-oate and methyl ent-15-atisene-19-oate mixture in dichloromethane (10 mL) (J. Org. Chem., Vol. 36, No. 18, 1971, 2625–2631) was added thereto, followed by stirring at room temperature for 2.5 hours. Then saturated aqueous sodium thiosulfate was added, and the mixture was extracted twice with diethyl ether. The resulting organic layer was washed with saturated brine, dried over magnesium sulfate and evaporated. The resulting residue was purified by silica gel column chromatography, to give methyl ent-15α-hydroxy-16-atisene-19-oate (S1-1) (92 mg, white crystals), methyl ent-15β-hydroxy-16-atisene-19-oate (S1-2) (84 mg, white crystals) and methyl ent-17-hydroxy-15-atisene-19-oate (S1-3) (18 mg, white crystals).

(S1-1) FAB-MS:m/z=333 (M+H)$^{+1}$H NMR (CDCl$_3$); δ (ppm) 0.76–1.91 (17H, m), 0.83 (3H, s), 1.19 (3H, s), 2.17 (1H, d, J=12.8 Hz), 2.27–2.32 (1H, m), 3.60 (1H, d, J=2.0 Hz), 3.65 (3H, s), 4.99 (1H, t, J=1.6 Hz), 5.06 (1H, t, J=1.6 Hz).

(S1-2) FAB-MS: m/z=333 (M+H)$^{+1}$H NMR (CDCl$_3$); δ (ppm) 0.78–1.92 (16H, m), 0.82 (3H, s), 1.19 (3H, s), 1.98–2.08 (1H, ml), 2.17 (1H, d, J=13.2 Hz), 2.29–2.33 (1H, m), 3.58–3.62 (1H, m), 3.66 (3H, s), 5.02 (1H, t, J=1.6 Hz), 5.08 (1H, t, J=1.6 Hz)

(S1-3) FAB-MS: m/z=333 (M+H)$^{+1}$H NMR (CDCl$_3$); δ (ppm) 0.78–1.93 (16H, m), 0.80 (3H, s), 1.19 (3H, s), 2.00 (1H, ddd, J=12.8, 9.6, 3.2 Hz), 2.11–2.21 (1H, m), 2.43–2.48 (1H, m) 3.65 (3H, s), 4.13 (2H, s), 5.84 (1H, d, J=1.6 Hz)

Example 2

Methyl ent-15α,17-dihydroxy-16α-atisane-19-oate

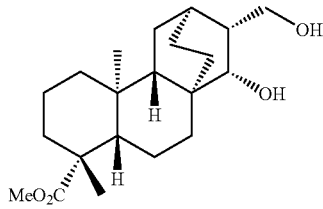

To a solution of methyl ent-15α-hydroxy-16-atisene-19-oate (2.68 g, 8.1 mmol) in tetrahydrofuran (162 mL) was added a solution of 1.0 M borane-tetrahydrofuran complex in tetrahydrofuran (24.3 mL, 24.3 mmol) under stirring on ice, followed by stirring at room temperature for 14 hours. Under stirring on ice, water (11.3 mL), a 3N aqueous sodium hydroxide (22.7 mL) and a 30% aqueous hydrogen peroxide (22.7 mL) were added thereto, followed by stirring at room temperature for 1 hour and 40 minutes. Water was added thereto, and the mixture was extracted twice with ethyl acetate. The resulting organic layer was washed with saturated brine, dried on magnesium sulfate and then evaporated. The resulting residue was purified by silica gel column chromatography, to give methyl ent-15α,17-dihydroxy-16α-atisane-19-oate (2.47 g, white crystals).

FAB-MS:m/z=351 (M+H)$^{+1}$H NMR (CDCl$_3$); δ (ppm) 0.78–1.91 (18H, m), 0.82 (3H, s), 1.18 (3H, s), 2.04–2.13 (1H, m), 2.17 (1H, d=13.6 Hz), 3.52 (1H, d, J=9.6 Hz), 3.56 (1H, dd, J=10.6, 4.6 Hz), 3.65 (3H, s), 4.03 (1H, t, J=10.6 Hz).

Example 3

Methyl ent-15β,17-dihydroxy-16α-atisane-19-oate (3-1) Synthesis of Methyl ent-17-hydroxy-15-oxo-16α-atisane-19-oate

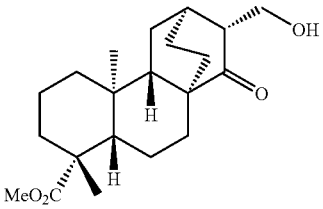

Methyl ent-15α,17-dihydroxy-16α-atisane-19-oate (1.95 g, 5.6 mmol) and sodium bromate (2.03 g, 13.5 mmol) were dissolved in acetonitrile (22.4 mL) and water (6.7 mL) and a solution of sodium hydrogensulfite (1.64 g, 13.5 mmol) in water (13.4 mL) was added thereto under stirring on ice. After stirring at room temperature for 2 hours, diethyl ether was added, and the mixture was washed with water, saturated aqueous sodium thiosulfate and saturated brine, dried over magnesium sulfate and then evaporated, to give the title compound (1.79 g).

$^1$H NMR (CDCl$_3$); δ (ppm) 0.81–2.39 (20H, m), 0.89 (3H, s), 1.19 (3H, s), 2.85 (1H, broad, J=9.6 Hz), 3.61–3.70 (1H, m), 3.66 (3H, s), 3.89 (1H, t, J=9.6 Hz).

(3-2) Synthesis of Methyl ent-15β,17-dihydroxy-16α-atisane-19-oate

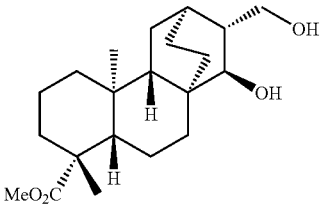

To a solution of sodium triacetoxy borohydride (5.62 g, 26.5 mmol) in acetonitrile (53 mL) was added acetic acid (3.03 mL, 53 mmol) under stirring on ice. Under stirring on ice, a solution of methyl ent-17-hydroxy-15-oxo-16α-atisane-19-oate (1.84 g) in acetonitrile (25 mL) was added thereto, followed by stirring for 5 hours by keeping ice-cooling. Under stirring on ice, water was added thereto and the mixture was extracted twice with ethyl acetate. The resulting organic layer was washed with saturated brine, dried over magnesium sulfate and evaporated. The resulting residue was purified by silica gel column chromatography, to give methyl ent-15β,17-dihydroxy-16α-atisane-19-oate (1.64 g, white foam).

ESI-MS:m/z=373 (M+Na)⁺ ¹H NMR (CDCl₃); δ (ppm) 0.69–1.90 (18H, m), 0.80 (3H, s), 1.18 (3H, s) 1.98 (1H, ddd, J=14.4 and 11.4 and 3.2 Hz), 2.17 (1H, d, J=13.6 Hz) 2.96 (1H, d, J=4.0 Hz), 3.58–3.72 (2H, m), 3.65 (3H, s)

Example 4

Methyl ent-15β-hydroxy-17-tosyloxy-16α-atisane-19-oate

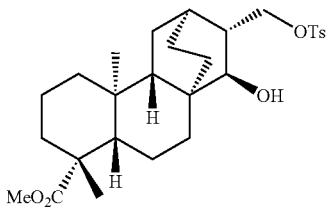

To a solution of methyl ent-15β,17-dihydroxy-16α-atisane-19-oate (72 mg, 0.205 mmol) in pyridine (4.1 mL) were added dimethylaminopyridine (75 mg, 0.614 mmol) and tosyl chloride (234 mg, 1.23 mmol) under stirring on ice. After stirring at room temperature for 17 hours, water was added under ice-cooling and the mixture was extracted twice with diethyl ether. The resulting organic layer was washed with saturated brine, dried over magnesium sulfate and then evaporated. The resulting residue was purified by silica gel column chromatography, to give methyl ent-15β-hydroxy-17-tosyloxy-16α-atisane-19-oate (99 mg pale yellow crystals).

¹H NMR (CDCl₃); δ (ppm) 0.68–1.99 (19H, m), 0.77 (3H, s), 1.17 (3H, s) 2.16 (1H, d, J=12.8 Hz), 2.46 (3H, s), 2.78–2.83 (1H, m), 3.64 (3H, s) 3.97 (1H, t, J=8.8 Hz), 4.06 (1H, dd, J=8.8 and 8.2 Hz), 7.35 (2H, d, J=8.4 Hz), 7.81 (2H, d, J=8.4 Hz)

Example 5 ent-15β-Hydroxy-17-methylthio-16α-atisane-19-oic acid

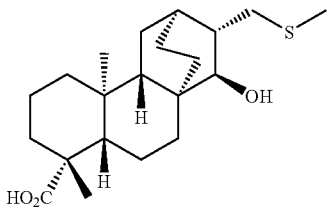

To a solution of methyl ent-15β-hydroxy-17-tosyloxy-16α-atisane-19-oate (1.66 g, 3.3 mmol) in hexamethylphosphoramide (16.5 mL) was added sodium thiomethoxide (1.16 g, 16.6 mmol) under stirring at room temperature, followed by stirring at 90° C. in nitrogen atmosphere for 43 hours. The reaction mixture was recovered to room temperature, saturated aqueous ammonium chloride was added thereto, and the mixture was extracted twice with ethyl acetate. The resulting organic layer was washed with saturated brine, dried over magnesium sulfate and evaporated. The resulting residue was purified by silica gel column chromatography, to give ent-15β-hydroxy-17-methylthio-16α-atisane-19-oic acid (923 mg, pale yellow crystals).

ESI-MS:m/z=365 (M−H)⁻ ¹H NMR (CDCl₃) δ (ppm) 0.75 (1H, dt, J=13.0 and 6.6 Hz), 0.92 (3H, s) 0.94–1.92 (18H, m), 1.25 (3H, s), 1.97 (1H, ddd, J=14.4 and 11.4 and 3.0 Hz), 2.15 (3H, s), 2.51–2.56 (2H, m), 2.96 (1H, d, J=4.4 Hz)

Example 6 ent-15β-Hydroxy-17-methylsulfinyl-16α-atisane-19-oic acid (Serofendic acid A (isomer (1)), Serofendic acid B (isomer (2)))

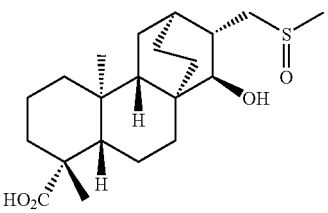

To a solution of ent 15β-hydroxy-17-methylthio-16α-atisane-19-oic acid (93 mg, 0.254 mmol) in chloroform (2.54 mL) was added 2-(phenylsulfonyl)-3-phenyloxaaziridine (86 mg, 0.329 mmol) (J. Am. Chem. Soc., 102, 2000 (1980)) under stirring on ice, followed by stirring for 2 hours. Dimethylsulfide (0.1 mL) was added and the mixture was evaporated. The resulting residue was purified by silica gel column chromatography. Further, 2 isomers are separated based on the configuration of sulfoxide by HPLC, to give isomer 1 (23.7 mg, white crystals) and isomer 2 (44.6 mg, white crystals).

Serofendic Acid A (Isomer (1))

ESI-MS:m/z=405 (M+Na)⁺ ¹H NMR (CD₃OD); δ (ppm) 0.76–0.87 (1H, m), 0.90 1.09 (4H, m), 0.94 (3H, s) 1.19 (3H, s), 1.32–1.44 (3H, m), 1.51–2.06 (1H, m), 2.12 (1H, d, J=14.0 Hz), 2.67 (3H, s), 2.82 (1H, dd, J=13.2 and 6.0 Hz), 2.90–2.98 (2H, m)

Serofendic Acid B (Isomer (2))

ESI-MS:m/z=405 (M+Na)⁺ ¹H NMR (CD₃OD); δ (ppm) 0.76–0.87 (1H, m), 0.91–1.11 (4H, m), 0.95 (3H, s), 1.19 (3H, s), 1.33–1.48 (3H, m), 1.52–2.08 (1H, m), 2.13 (1H, d, J=13.6 Hz), 2.69 (3H, s), 2.87 (1H, dd, J=13.0 and 9.0 Hz), 2.91 (1H, d, J=4.0 Hz), 2.99 (1H, dd, J=13.0 and 7.0 Hz)

Example 7

Methyl ent-15β-hydroxy-17-methylthio-16α-atisane-19-oate

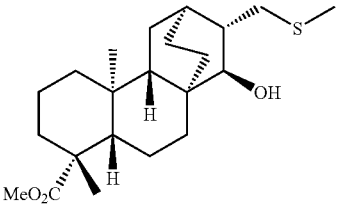

To a solution of methyl ent-15β-hydroxy-17-tosyloxy-16α-atisane-19-oate (44 mg, 0.0827 mmol) in dimethylformamide (1.75 mL) was added sodium thiomethoxide (12 mg, 0.171 mmol) under stirring at room temperature, followed by stirring for 80 minutes at room temperature. A saturated ammonium chloride solution was added, and the mixture was extracted twice with diethyl ether. The resulting organic layer was washed with saturated brine, dried over magnesium sulfate and then evaporated, to give methyl ent-15β-hydroxy-17-methylthio-16α-atisane-19-oate (34 mg, pale yellow crude crystals).

$^1$H NMR (CDCl$_3$); δ (ppm) 0.69–0.79 (1H, m), 0.80 (3H, s), 0.89–2.02 (19H, m), 1.18 (3H, s), 2.15 (3H, s), 2.51–2.56 (2H, m), 2.93–2.97 (1H, m), 3.65 (3H, s)

Example 8

Methyl ent-15β-hydroxy-17-methylsulfinyl-16α-atisane-19-oate

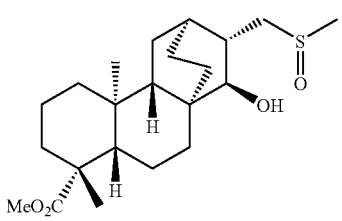

To a solution of methyl ent-15β-hydroxy-17-methylthio-16α-atisane-19-oate (34 mg, 0.0893 mmol) in chloroform (1.5 mL) was added 2-(phenylsulfonyl)-3-phenyloxaaziridine (34.2 mg, 0.131 mmol) under stirring on ice, followed by stirring for 40 minutes. Dimethylsulfide (0.1 mL) was added, and the mixture was evaporated. The resulting residue was purified by silica gel column chromatography, to give methyl ent-15β-hydroxy-17-methylsulfinyl-16α-atisane-19-oate (31.6 mg white crystals).

$^1$H NMR (CD$_3$OD); δ (ppm) 0.76–2.04 (19H, m), 0.83 (3H, s), 1.17 (3H, s), 2.14 (1H, d, J=13.9 Hz), 2.67 and 2.69 (3H, s×2), 2.78–3.03 (3H, m), 3.28 (3H, s)

Example 9 ent-15β-Hydroxy-17-methylsulfonyl-16α-atisane-19-oic acid

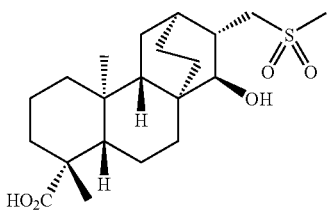

To a solution of ent-15β-hydroxy-17-methylthio-16α-atisane-19-oic acid (27 mg, 0.0737 mmol) in acetic acid (0.74 mL) was added a 30% aqueous hydrogen peroxide under stirring at room temperature. After stirring at 50° C. for 1 hour, the mixture was allowed to cool to room temperature, and saturated sodium thiosulfate was added and extracted twice with ethyl acetate. The resulting organic layer was washed with saturated brine, dried over magnesium sulfate and evaporated. The resulting residue was purified by silica gel column chromatography, to give ent-15β-hydroxy-17-methylsulfonyl-16α-atisane-19-oic acid (11 mg, white crystals).

FAB-MS:m/z=397 (M−H)$^{−1}$ $^1$H NMR (CD$_3$OD); δ (ppm) 0.75–0.86 (1H, m), 0.87–2.09 (18H, M), 0.94 (3H, s), 1.18 (3H, s), 2.13 (1H, d, J=12.8 Hz), 2.936 (1H, d, J=4.0 Hz), 3.025 (3H, s), 3.17 (1H, dd, J=14.0 and 7.2 Hz)

Example 10

Methyl ent-15α-hydroxy-17-tosyloxy-16β-atisane-19-oate

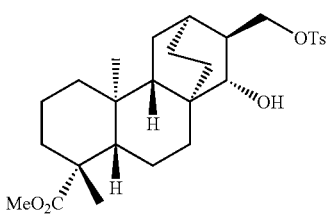

From ent-15β-hydroxy-16-atisene-19-oate obtained in Example 1, methyl ent-15α-hydroxy-17-tosyloxy-16β-atisane-19-oate was obtained in the same manners as described in Examples 2, 3 and 4.

$^1$H NMR (CDCl$_3$); δ (ppm) 0.70–1.88 (19H, m), 0.80 (3H, s), 1.17 (3H, s) 2.17 (1H, d, J=13.6 Hz), 2.46 (3H, s), 2.77 (1H, broad s), 3.64 (3H, s) 3.95 (1H, t, J=9.2 Hz), 4.04 (1H, dd, J=9.2 and 7.0 Hz), 7.35 (2H, d, J=8.4 Hz), 7.80 (2H, d, J=8.4 Hz)

Example 11 ent-15α-Hydroxy-17-methylthio-16β-atisane-19-oic acid

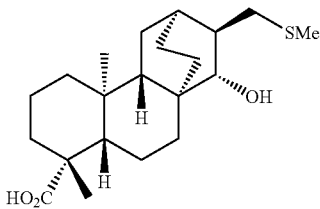

From methyl ent-15α-hydroxy-17-tosyloxy-16β-atisane-19-oate (157 mg, 0.311 mmol) obtained in Example 10, ent-15α-hydroxy-17-methylthio-16β-atisane-19-oic acid (39 mg, pale yellow syrup) was obtained in the same manner as described in Example 5.

ESI-MS:m/z=365 (M−H)$^{−1}$ $^1$H NMR (CDCl$_3$); δ (ppm) 0.93 (3H, s), 1.25 (3H, s), 2.14 (3H, s), 2.14–2.21 (1H, m) 2.50–2.56 (2H, m), 2.91–2.95 (1H, m)

Example 12 ent-15α-Hydroxy-17-methylsulfinyl-16β-atisane-19-oic acid

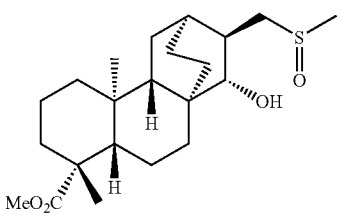

From ent-15α-hydroxy-17-methylthio-16β-atisane-19-oic acid (39 mg, 0.106 mmol) obtained in Example 11, ent-15α-hydroxy-17-methylsulfinyl-16β-atisane-19-oic acid (27 mg, white crystals) was obtained in the same manner as described in Example 6.

ESI-MS:m/z=381 (M−H)$^{-1}$H NMR (CD$_3$OD); δ (ppm) 0.80–1.98 (19H, m) 0.96 (3H, s), 1.18 (3H, s) 2.13 (1H, d, J=13.6 Hz), 2.67 and 2.69 (3H, s×2), 2.79–3.00 (3H, m)

Example 13

Methyl ent-17-hydroxy-16α,β-atisane-19-oate

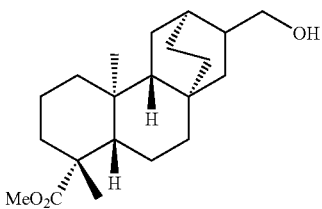

From methyl ent-16-atisene-19-oate (J. Org. Chem., Vol. 36, No. 18, 1971, 2625–2631) (115 mg, 0.363 mmol), methyl ent-17-hydroxy-16α,β-atisane-19-oate (76.2 mg, colorless amorphous) was obtained in the same manner as described in Example 2.

$^1$H NMR (CDCl$_3$); δ (ppm) 0.53–1.94 (21H, m), 0.768 and 0.774 (3H, s×2) 1.163 and 1.169 (3H, s×2) 2.161 (1H, d, J=12.8 Hz), 3.47–3.56 (2H, m) 3.640 and 3.642 (3H, s×2)

Example 14

Methyl ent-17-mesyloxy-16α,β-atisane-19-oate

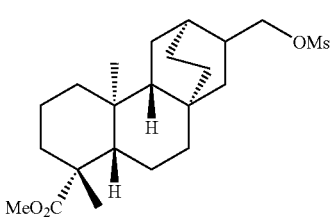

To a solution of methyl ent-17-hydroxy-16α,β-atisane-19-oate obtained in Example 13 (76.2 mg, 0.228 mmol) in dichloromethane (2.28 mL) were added triethylamine (0.159 mL, 1.14 mmol) and methanesulfonyl chloride (0.053 mL, 0.685 mmol) under stirring on ice. After stirring on ice for 2 hours, diethyl ether was added, and the mixture was washed with water and saturated brine, dried over magnesium sulfate and then evaporated, to give methyl ent-17-mesyloxy-16α,β-atisane-19-oate (94 mg).

$^1$H NMR (CDCl$_3$); δ (ppm) 0.766 and 0.772 (3H, s×2), 1.167 and 1.171 (3H, s×2) 3.006 and 3.007 (3H, s×2), 3.642 (3H, s), 4.06–4.15 (2H, m)

Example 15 ent-17-Methylthio-16α,β-atisane-19-oic acid

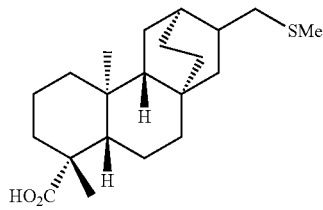

To a solution of methyl ent-17-mesyloxy-16α,β-atisane-19-oate (94 mg, 0.228 mmol) obtained in Example 14 in dimethylformamide (5 mL) was added sodium thiomethoxide (64 mg, 0.913 mmol) under stirring at room temperature. After stirring at 60° C. for 5 hours, the reaction mixture was allowed to cool to room temperature. Saturated aqueous ammonium chloride was added thereto, and the mixture was extracted twice with ethyl acetate. The resulting organic layer was washed with saturated brine, dried over magnesium sulfate and evaporated. The resulting residue was purified by silica gel column chromatography, to give ent-17-methylthio-16α,β-atisane-19-oic acid (44.3 mg, white crystals).

ESI-MS:m/z=349 (M−H)$^{-1}$H NMR (CDCl$_3$); δ (ppm) 0.68–1.93 (21H, m), 0.881 and 0.887 (3H, s×2), 1.231 and 1.235 (3H, s×2), 2.091 (3H, s), 2.12–2.19 (1H, m), 2.42–2.56 (2H, m)

Example 16 ent-17-Methylsulfinyl-16α,β-atisane-19-oic acid

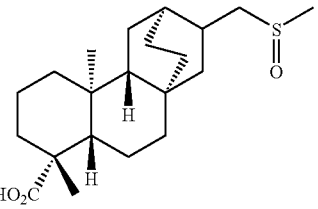

From ent-17-methylthio-16α,β-atisane-19-oic acid (21.8 mg, 0.0622 mmol) obtained in Example 15, ent-17-methylsulfinyl-16α,β-atisane-19-oic acid (19.2 mg, colorless amorphous) was obtained in the same manner as described in Example 6.

ESI-MS:m/z=365 (M−H)$^{-1}$H NMR (CD$_3$OD); δ (ppm) 0.80–2.00 (20H, m), 0.923 and 0.928 (3H, s×2) 1.176 and 1.179 (3H, s×2), 2.120 (1H, d, J=13.2 Hz), 2.15–2.27 (1H, m) 2.629–2.661 (3H, m), 2.74–2.93 (2H, m)

Example 17 ent-15β-Acetoxy-17-methylthio-16α-atisane-19-oic acid

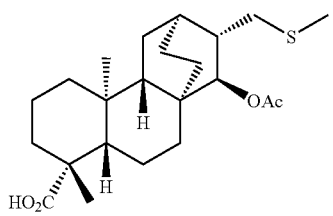

To a solution of ent-15β-hydroxy-17-methylthio-16α-atisane-19-oic acid (110 mg, 0.300 mmol) obtained in Example 5 in pyridine (1 mL) was added acetic anhydride (0.1 mL) under stirring on ice, followed by stirring at room temperature for 5 hours. The reaction mixture was ice-cooled, water was added, and the mixture was extracted twice with ethyl acetate. The resulting organic layer was washed with saturated brine, dried over magnesium sulfate and evaporated. The resulting residue was purified by silica gel column chromatography, to give ent-15β-acetoxy-17-methylthio-16α-atisane-19-oic acid (112 mg, pale yellow crystals).

$^1$H NMR (CDCl$_3$); δ (ppm) 0.80–2.10 (19H, m), 0.91 (3H, s), 1.25 (3H, s), 2.08 (3H, s) 2.11 (3H, s), 2.13–2.21 (1H, m), 2.50 (1H, dd, J=12.4 and 10.4 Hz) 2.84 (1H, dd, J=12.4 and 6.2 Hz), 4.18 (1H, d, J=4.0 Hz)

Example 18 ent-15β-Acetoxy-17-methylthio-16α-atisane-19-amide

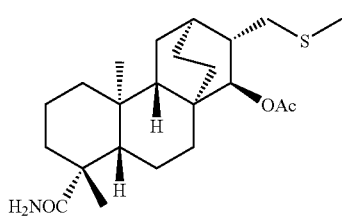

To a solution of ent-15β-acetoxy-17-methylthio-16α-atisane-19-oic acid (22 mg, 0.054 mmol) obtained by Example 17 in dichloromethane (2.1 mL) was added oxalyl chloride (14 μl, 0.160 mmol) under stirring on ice. After stirring at room temperature for 1 hour, ammonia gas was blown into the reaction mixture for 30 seconds. Water was added, and the mixture was extracted twice with ethyl acetate. The resulting organic layer was washed with saturated brine, dried over magnesium sulfate and evaporated, to give ent-15β-acetoxy-17-methylthio-16α-atisane-19-amide (28 mg, pale yellow crystals).

$^1$H NMR (CDCl$_3$); δ (ppm) 0.79–2.10 (20H, m), 0.96 (3H, s), 1.20 (3H, s), 2.08 (3H, s) 2.11 (3H, s), 2.50 (1H, dd, J=12.4 and 10.4 Hz), 2.831 (1H, dd, J=12.4 and 6.0 Hz) 4.18 (1H, d, J=4.0 Hz), 5.35 (1H, broad s), 5.575 (1H, broad s)

Example 19 ent-15β-Hydroxy-17-methylthio-16α-atisane-19-amide

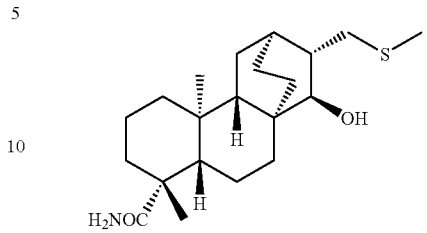

To a solution of ent-15β-acetoxy-17-methylthio-16α-atisane-19-amide (10.1 mg, 0.0248 mmol) obtained in Example 18 in ethanol (0.5 mL) was added sodium hydroxide (40 mg, 1.00 mmol) under stirring at room temperature, followed by stirring for 14 hours at room temperature. Water was added and the mixture was extracted twice with ethyl acetate. The resulting organic layer was washed with saturated brine, dried over magnesium sulfate and evaporated, to give ent-15β-hydroxy-17-methylthio-16α-atisane-19-amide (8.1 mg).

$^1$H NMR (CDCl$_3$); δ (ppm) 0.66–2.12 (20H, m), 0.96 (3H, s), 1.21 (3h, s), 2.15 (3H, s) 2.48–2.56 (2H, m) 2.96 (1H, d, J=4.0 Hz), 5.39 (1H, broad s), 5.59 (1H, broad s)

Example 20 ent-15β-Hydroxy-17-methylsulfinyl-16α-atisane-19-amide

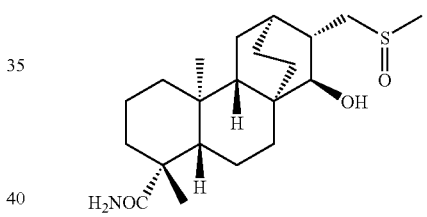

From ent-15β-hydroxy-17-methylthio-16α-atisane-19-amide obtained in Example 19 (8.1 mg, 0.0222 mmol), ent-15β-hydroxy-17-methylsulfinyl-16α-atisane-19-amide (7.0 mg) was obtained in the same manner as described in Example 6.

ESI-MS:m/z=404 (M+Na)$^+$ $^1$H NMR (CD$_3$OD); δ (ppm) 0.75–2.13 (20H, m), 0.97 (3H, s), 1.18 (3H, s) 2.67 and 2.69 (3H, s×2), 2.78–3.03 (3H, m)

Example 21 ent-15β,19-Dihydroxy-17-methylthio-16α-atisane

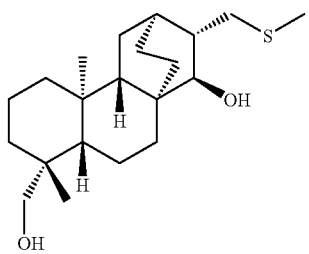

To a solution of ent-15β-hydroxy-17-methylsulfinyl-16α-atisane-19-oic acid (270 mg, 0.707 mmol) obtained in Example 6 in tetrahydrofuran (14.1 mL) was added lithium aluminum hydride (537 mg, 14.2 mmol) under stirring on ice. After heating under reflux for 4 hours, the reaction mixture was ice-cooled, and water and 1N hydrochloric acid was added. The reaction was extracted twice with ethyl acetate, and the resulting organic layer was washed with saturated brine, dried over magnesium sulfate and evaporated. The resulting residue was purified by silica gel column chromatography, to give ent-15β,19-dihydroxy-17-methylthio-16α-atisane (252 mg, white crystals).

$^1$H NMR (CDCl$_3$); δ (ppm) 0.66–0.77 (1H, m), 0.79–1.95 (20H, m), 0.95 (3H, s) 0.97 (3H, s), 2.14 (3H, s), 2.48–2.56 (2H, m), 2.92 (1H, d, J=4.0 Hz) 3.47 (1H, d, J=10.8 Hz), 3.75 (1H, d, J=10.8 Hz)

Example 22 ent-15β,19-Dihydroxy-17-methylsulfinyl-16α-atisane

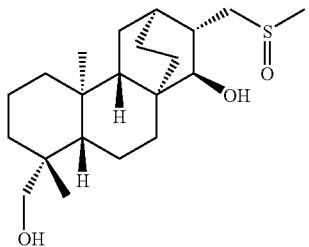

From ent-15β,19-dihydroxy-17-methylthio-16α-atisane (16 mg, 0.0454 mmol) obtained in Example 21, ent-15β,19-dihydroxy-17-methylsulfinyl-16α-atisane (10.5 mg) was obtained in the same manner as described in Example 6.

ESI-MS:m/z=391 (M+Na)$^{+1}$H NMR (CD$_3$OD); δ (ppm) 0.73–2.00 (20H, m), 0.93 (3H, s), 0.99 (3H, s) 2.67 and 2.68 (3H, s×2), 2.78–3.03 (3H, m), 3.32–3.38 (1H, m) 3.73 (1H, d, J=11.2 Hz)

Example 23 ent-15β-Acetoxy-17-methylthio-16α-atisane-19-nitrile

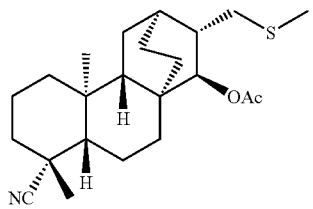

To a solution of ent-15β-acetoxy-17-methylthio-16α-atisane-19-amide (28 mg, 0.0687 mmol) obtained in Example 18 in toluene (1.37 mL) was added thionyl chloride (0.125 mL, 1.71 mL) under stirring at room temperature, followed by stirring for 4 hours at 65° C. Under ice-cooling, water was added and the mixture was extracted twice with diethyl ether. The resulting organic layer was washed with saturated brine, dried over magnesium sulfate and evaporated. The resulting residue was purified by silica gel column chromatography, to give ent-15β-acetoxy-17-methylthio-16α-atisane-19-nitrile (16.8 mg).

$^1$H NMR (CDCl$_3$); δ (ppm) 0.79–2.14 (20H, m), 1.21 (3H, s), 1.36 (3H, s), 2.08 (3H, s) 2.10 (3H, s), 2.51 (1H, dd, J=12.8 and 10.4 Hz), 2.85 (1H, dd, J=12.8 and 6.0 Hz) 4.18 (1H, d, J=3.6 Hz)

Example 24 ent-15β-Hydroxy-17-methylsulfinyl-16α-atisane-19-nitrile

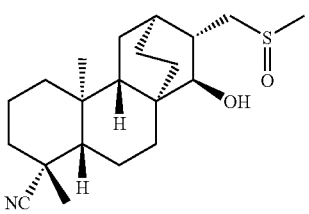

From ent-15β-acetoxy-17-methylthio-16α-atisane-19-nitrile (16.8 mg, 0.0431 mmol) obtained in Example 23, ent-15β-hydroxy-17-methylsulfinyl-16α-atisane-19-nitrile (3.68 mg, colorless amorphous) was obtained in the same manners as described in Example 19 and Example 6.

ESI-MS:m/z=386 (M+Na)$^{+1}$H NMR (CD$_3$OD); δ (ppm) 0.80–2.49 (20H, m), 1.22 (3H, s), 1.35 (3H, s) 2.67 and 2.69 (3H, s×2), 2.79–3.03 (3H, m)

Example 25 ent-15β-Acetoxy-17-methylthio-16α-atisane-19-dimethylamide

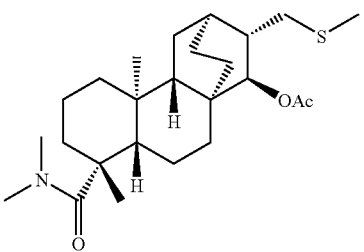

To a solution of ent-15β-acetoxy-17-methylthio-16α-atisane-19-oic acid (22.8 mg, 0.0559 mmol) obtained in Example 17 in dichloromethane (1 mL) was added oxalyl chloride (0.015 mL, 0.172 mmol) under stirring on ice, followed by stirring for 3 hours at room temperature. Under ice-cooling, a solution of 2.0 M dimethylamine in tetrahydrofuran (0.28 mL, 0.56 mmol) was added thereto, followed by stirring at room temperature for 5 minutes. Then, water was added thereto and the mixture was extracted twice with ethyl acetate. The resulting organic layer was washed with saturated brine, dried over magnesium sulfate and evaporated, to give ent-15β-acetoxy-17-methylthio-16α-atisane-19-dimethylamide (20 mg).

$^1$H NMR (CDCl$_3$); δ (ppm) 0.78–2.49 (19H, m), 0.93 (3H, s), 1.26 (3H, s), 2.07 (3H, s), 2.10 (3H, s), 2.50 (1H, dd, J=12.8 and 10.4 Hz), 2.84 (1H, dd, J=12.8 and 5.6 Hz) 3.00 (6H, s), 4.17 (1H, d, J=4.0 Hz)

Example 26 ent-15β-Hydroxy-17-methylthio-16α-atisane-19-dimethylamide

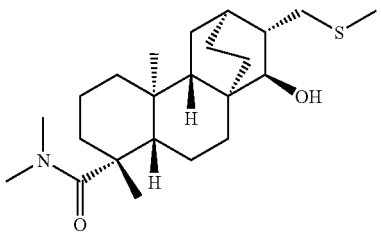

From ent-15β-acetoxy-17-methylthio-16α-atisane-19-dimethylamide obtained in Example 25 (20 mg, 0.0459 mmol), ent-15β-hydroxy-17-methylthio-16α-atisane-19-dimethylamide (15.2 mg, pale yellow crystals) was obtained in the same manner as described in Example 19.

$^1$H NMR (CDCl$_3$); δ (ppm) 0.66–0.79 (1H, m), 0.82–2.29 (18H, m), 0.94 (3H, s) 1.26 (3H, s), 2.14 (3H, s), 2.43 (1H, d, J=14.4 Hz), 2.50–2.57 (2H, m) 2.91–2.96 (1H, m), 3.01 (6H, s)

Example 27 ent-15β-Hydroxy-17-methylsulfinyl-16α-atisane-19-dimethylamide

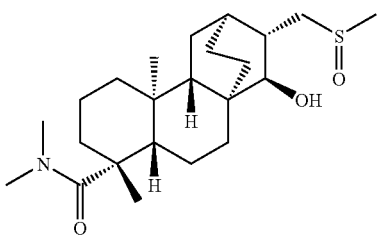

From ent-15β-hydroxy-17-methylthio-16α-atisane-19-dimethylamide obtained in Example 26 (3.2 mg, 0.0081 mmol), ent-15β-hydroxy-17-methylsulfinyl-16α-atisane-19-dimethylamide (2.75 mg) was obtained in the same manner as described in Example 6.

$^1$H NMR (CD$_3$OD); δ (ppm) 0.76–0.86 (1H, m), 0.86–2.24 (18H, m), 0.94 (3H, s) 1.26 (3H, s), 2.52 (1H, d, J=14.4 Hz), 2.67 and 2.69 (3H, s×2), 2.78–3.07 (3H, m) 3.02 (6H, s)

Example 28 ent-15β-Hydroxy-17-methylthio-19-tosyloxy-16α-atisane

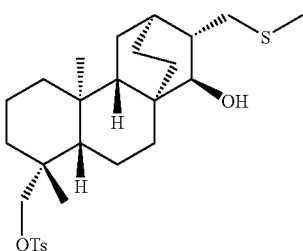

From ent-15β,19-dihydroxy-17-methylthio-16α-atisane (54 mg, 0.153 mmol) obtained in Example 21, ent-15β-hydroxy-17-methylthio-19-tosyloxy-16α-atisane (81 mg) was obtained in the same manner as described in Example 4.

$^1$H NMR (CDCl$_3$); δ (ppm) 0.65–0.76 (1H, m), 0.76–1.94 (19H, m), 0.82 (3H, s) 0.91 (3H, s), 2.13 (3H, s), 2.46 (3H, s), 2.48–2.54 (2H, m), 2.91 (1H, d, J=4.0 Hz) 3.83 (1H, d, J=9.2 Hz), 4.14 (1H, d, J=9.2 Hz), 7.35 (1H, d, J=8.4 Hz) 7.79 (1H, d, J=8.4 Hz)

Example 29 ent-19-Azido-15β-hydroxy-17-methylthio-16α-atisane

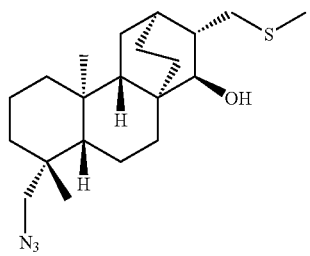

To a solution of ent-15β-hydroxy-17-methylthio-19-tosyloxy-16α-atisane obtained in Example 28 (28 mg, 0.0553 mmol) in hexamethylphosphoramide (1 mL) were added tetrabutylammonium iodide (2.04 mg, 0.00553 mmol) and sodium azide (10.8 mg, 0.0213 mmol) under stirring at room temperature, followed by stirring for 3 hours at 140° C. After recovering the reaction mixture to room temperature, saturated ammonium chloride was added thereto and the mixture was extracted twice with diethyl ether. The resulting organic layer was washed with saturated brine, dried over magnesium sulfate and evaporated. The resulting residue was purified by silica gel column chromatography, to give ent-19-azido-15β-hydroxy-17-methylthio-16α-atisane (8.9 mg).

$^1$H NMR (CDCl$_3$); δ (ppm) 0.67–0.79 (1H, m), 0.84–1.98 (19H, m), 0.963 (6H, s) 2.14 (3H, s), 2.512.56 (2H, m), 2.93 (1H, s), 3.16 (1H, d, J=12.0 Hz) 3.53 (1H, d, J=12.0 Hz)

Example 30 ent-19-{(t-Butoxycarbonyl)-amino}-15β-hydroxy-17-methylthio-16α-atisane (30-1) Synthesis of ent-19-amino-15β-hydroxy-17-methylthio-16α-atisane

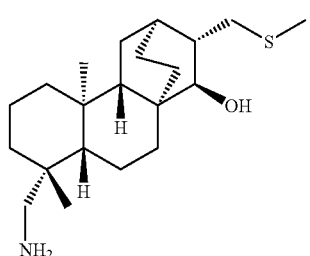

To a solution of ent-19-azido-15β-hydroxy-17-methylthio-16α-atisane obtained in Example 29 (6.6 mg, 0.0168 mmol) in tetrahydrofuran (1 mL) was added lithium aluminum halide (1.27 mg, 0.0335 mmol) under stirring at room temperature, followed by stirring for 90 minutes at room temperature. After adding a small amount of a27% aqueous ammonia, the mixture was filtered. The filtrate was evaporated, to give ent-19-amino-15β-hydroxy-17-methylthio-16α-atisane (21 mg, crude product).

ESI-MS:m/z=352 (M+Na)+

(30-2) Synthesis of ent-19-{(t-Butoxycarbonyl)-amino}-15β-hydroxy-17-methylthio-16α-atisane

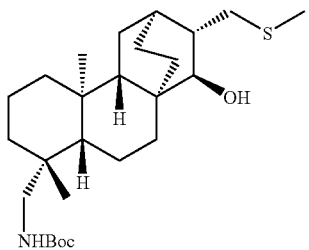

To a solution of ent-19-amino-15β-hydroxy-17-methylthio-16α-atisane (21 mg) in tetrahydrofuran (2 mL) were added di-t-butyl dicarbonate (39 mg, 0.179 mmol), triethylamine (0.042 mL, 0.299 mmol) and 4-dimethylamino pyridine (7.3 mg, 0.0598 mmol) under stirring at room temperature, followed by stirring for 2 hour at room temperature. After adding water, the reaction mixture was extracted twice with diethyl ether. The resulting organic layer was washed with saturated brine, dried over magnesium sulfate and evaporated. The resulting residue was purified by silica gel column chromatography, to give ent-N-(t-butoxycarbonyl)-19-amino-15β-hydroxy-17-methylthio-16α-atisane (4.4 mg).

1H NMR (CDCl3); δ (ppm) 0.65–0.78 (1H, m), 0.80–1.98 (19H, m), 1.44 (9H, s) 2.14 (3H, s), 2.49–2.56 (2H, m), 2.84–2.96 (2H, m), 3.48 (1H, dd, J=13.6 and 7.6 Hz)

Example 31 ent-19-{(t-Butoxycarbonyl)amino}-15β-hydroxy-17-methylsulfinyl-16α-atisane

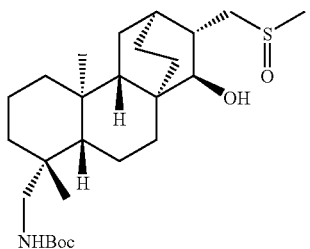

From ent-N-(t-butoxycarbonyl)-19-aminio-15β-hydroxy-17-methylthio-16α-atisane (4.4 mg) obtained in Example 30, ent-N-(t-butoxycarbonyl)-19-amino-15β-hydroxy-17-methylsulfinyl-16α-atisane (2.2 mg) was obtained in the same manner as described in Example 6.

ESI-MS:m/z=490 (M+Na)+ 1H NMR (CD3OD); δ (ppm) 0.74–2.04 (20H, m), 0.85 (3H, s), 1.06 (3H, s), 1.43 (9H, s) 2.67 and 2.69 (3H, s×2)

Example 32 ent-19-Amino-15β-hydroxy-17-methylsulfinyl-16α-atisane-trifluoroacetic acid

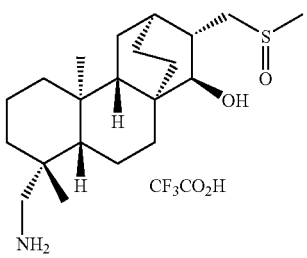

To a solution of ent-N-(t-butoxycarbonyl)-19-amino-15β-hydroxy-17-methylsulfinyl-16α-atisane obtained in Example 31 (1.8 mg, 0.00385 mmol) in dichloromethane (1 mL) was added trifluoroacetic acid (1 mL) under stirring on ice, followed by stirring for 5 hours at room temperature. Then, the mixture was evaporated, to give ent-19-amino-15β-hydroxy-17-methylsulfinyl-16α-atisane-trifluoroacetic acid (1.59 mg).

ESI-MS:m/z=368 (M+H)+ 1H NMR (CD3OD); δ (ppm) 0.66–1.96 (20H, m), 0.92 (3H, s), 0.93 (3H, s) 2.58 and 2.59 (3H, s×2)

Example 33

Methyl ent-15β,17-Bis{(methoxymethyl)oxy}-16α-atisane-19-oate

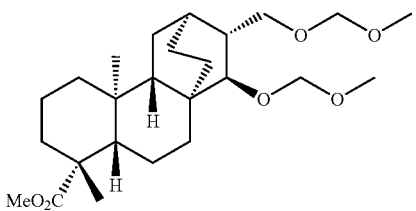

To a solution of methyl ent-15β,17-dihydroxy-16α-atisane-19-oate obtained in Example 3 (197 mg, 0.562 mmol) in dichloromethane (11.2 mL) were added methoxymethyl chloride (0.427 mL, 5.62 mmol) and diisopropyl ethylamine (1.47 mL, 8.44 mmol) under stirring on ice, followed by stirring for 16 hours at room temperature. Under ice-cooling, water was added thereto and the mixture was extracted twice with diethyl ether. The resulting organic layer was washed with saturated brine, dried over magnesium sulfate and evaporated, to give methyl ent-15β,17-bis{(methoxymethyl)oxy}-16α-atisane-19-oate (260 mg, pale yellow crude syrup).

1H NMR (CDCl3) δ (ppm) 0.64–1.89 (18H, m), 0.79 (3H, s), 1.18 (3H, s) 1.90–1.99 (1H, m), 2.16 (1H, d, J=13.2 Hz), 2.64 (1H, d, J=3.2 Hz), 3.36 (3H, s) 3.37–3.43 (1H, m), 3.40 (3H, s), 3.59–3.69 (1H, m), 3.65 (3H, s), 4.56 (1H, d, J=6.4 Hz) 4.62 (1H, d, J=6.4 Hz), 4.65 (1H, d, J=6.4 Hz), 4.81 (1H, d, J=6.4 Hz)

Example 34 ent-19-Hydroxy-15β,17-bis{(methoxymethyl)oxy}-16α-atisane

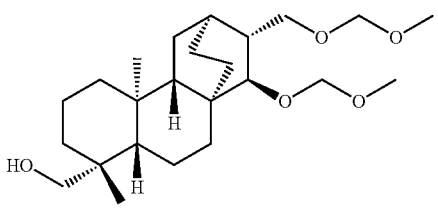

To a solution of ent-15β,17-bis{(methoxymethyl)oxy}-16α-atisane-19-oate obtained in Example 33 in tetrahydrofuran (11.9 mL) was added lithium aluminum hydride (67.5 mg, 1.78 mmol) under stirring on ice, followed by stirring for 4 hours at room temperature. Under ice-cooling, water and a 5N aqueous sodium hydroxide were added thereto, and the mixture was extracted twice with ethyl acetate. The resulting organic layer was washed with saturated brine, dried over magnesium sulfate and evaporated, to give ent-19-hydroxy-15β,17-bis{(methoxymethyl)oxy}-16α-atisane (228 mg, colorless crude syrup).

$^1$H NMR (CDCl$_3$); δ (ppm) 0.64–0.75 (1H, m), 0.82–1.92 (19H, m), 0.95 (3H, s) 0.97 (3H, s), 2.61 (1H, d, J=3.6 Hz), 3.36 (3H, s), 3.36–3.43 (1H, m), 3.39 (3H, s) 3.47 (1H, d, J=10.8 Hz), 3.64 (1H, dd, J=9.6 and 5.2 Hz), 3.76 (1H, d, J=10.8 Hz) 4.56 (1H, d, J=6.8 Hz), 4.62 (1H, d, J=6.4 Hz), 4.65 (1H, d, J=6.4 Hz) 4.81 (1H, d, J=6.8 Hz)

Example 35 ent-15β,17-Bis{(methoxy)oxy}-16α-atisane

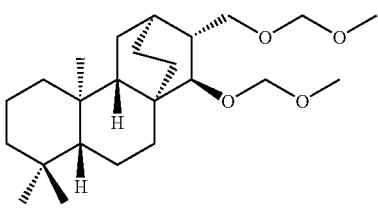

To a solution of ent-19-hydroxy-15β,17-bis{(methoxymethyl)oxy}-16α-atisane obtained in Example 34 (9.6 mg, 0.0234 mmol) in 1,2-dichloroethane (1 mL) was added 1,1'-thiocarbonyldiimidazole (12.5 mg, 0.0701 mmol) under stirring at room temperature, followed by stirring for 19 hours at room temperature. After adding 0.5N hydrochloric acid, the mixture was stirred for 20 hours at room temperature and then extracted with diethyl ether. The resulting organic layer was washed with saturated sodium hydrogen carbonate and saturated brine, dried over magnesium sulfate and evaporated. The resulting residue was dissolved in toluene (1 mL), and 2,2'-azobisisobutyronitrile (0.8 mg, 0.00487 mmol) and tributyltin hydride (8.0 μl, 0.0297 mmol) were added thereto under stirring at room temperature, followed by stirring for 1 hour at 70° C. The reaction mixture was recovered to room temperature and evaporated. The resulting residue was purified by silica gel column chromatography, to give ent-15β,17-bis{(methoxymethyl)oxy}-16α-atisane (4.8 mg).

$^1$H NMR (CDCl$_3$); δ (ppm) 0.64–0.76 (1H, m), 0.76–1.97 (19H, m), 0.82 (3H, s) 0.86 (3H, s), 0.97 (3H, s), 2.61 (1H, d, J=3.2 Hz), 3.36 (3H, s), 3.39 (3H, s) 3.37–3.44 (1H, m), 3.60–3.67 (1H, m), 4.56 (1H, d, J=6.6 Hz), 4.62 (1H, d, J=6.4 Hz) 4.65 (1H, d, J=6.4 Hz), 4.81 (1H, d, J=6.6 Hz)

Example 36 ent-15β,17-Dihydroxy-16α-atisane

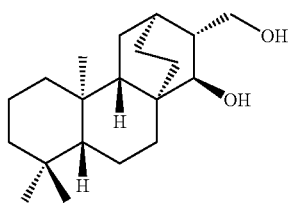

To a solution of ent-15β,17-bis{(methoxymethyl)oxy}-16α-atisane (4.8 mg, 0.0123 mmol) obtained in Example 35 in tetrahydrofuran (1 mL) was added 7.5N hydrochloric acid was added under stirring on ice. After stirring at room temperature for 3 hours, water was added and the mixture was extracted twice with ethyl acetate. The resulting organic layer was washed with saturated aqueous sodium hydrogen carbonate and saturated brine, dried over magnesium sulfate and evaporated. The resulting residue was purified on silica gel column chromatography, to give ent-15β,17-dihydroxy-16α-atisane (1.4 mg).

$^1$H NMR (CDCl$_3$); δ (ppm) 0.65–1.82 (19H, m), 0.82 (3H, s), 0.86 (3H, s), 0.97 (3H, s) 1.89–1.99 (1H, m), 2.94 (1H, d, J=4.4 Hz), 3.62 (1H, dd, J=10.0 and 7.6 Hz) 3.65–3.73 (1H, m)

Example 37 ent-15β-Hydroxy-17-methylthio-16α-atisane

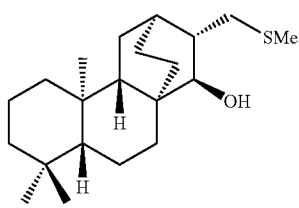

From ent-15β,17-dihydroxy-16α-atisane (5.3 mg, 0.0173 mmol) obtained in Example 36, ent-15β-hydroxy-17-methylthio-16α-atisane (3.5 mg) was obtained in the same manners as described in Example 4 and Example 7.

$^1$H NMR (CDCl$_3$); δ (ppm) 0.65–1.98 (20H, m), 0.821 (3H, s), 0.86 (3H, s), 0.97 (3H, s) 2.14 (3H, s), 2.49–2.57 (2H, m), 2.89–2.95 (1H, m)

Example 38 ent-15β-Hydroxy-17-methylsulfinyl-16α-atisane

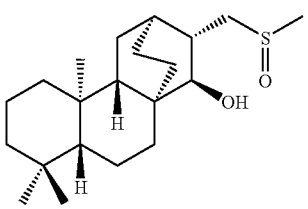

From ent-15β-hydroxy-17-methylthio-16α-atisane (2.8 mg, 0.0083 mmol) obtained in Example 37, ent-15β-hydroxy-17-methylsulfinyl-16α-atisane (1.46 mg) was obtained in the same manner as described in Example 6.

ESI-MS:m/z=375 (M+Na)[+1]H NMR (CD$_3$OD); δ (ppm) 0.74–2.05 (20H, m), 0.85 (3H, s), 0.87 (3H, s), 1.02 (3H, s) 2.67 and 2.69 (3H, s×2), 2.78–3.03 (3H, m)

Example 39 ent-19-Methoxy-15β,17-bis{(methoxymethyl)oxy}-16α-atisane

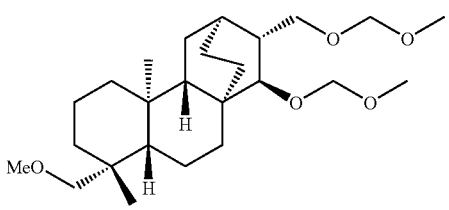

To a solution of ent-19-hydroxy-15β,17-bis{(methoxymethyl)oxy}-16α-atisane (14 mg, 0.0341 mmol) obtained in Example 34 in hexamethylphosphoramide (1 mL) were added sodium hydride (60% dispersion in mineral oil) (7 mg, 0.175 mmol) and methyl triflate (39 μl, 0.344 mmol) under stirring at room temperature. After stirring for 25 hours at room temperature, the reaction mixture was ice-cooled, and water was added, and the mixture was extracted twice with ethyl acetate. The resulting organic layer was washed with saturated brine, dried over magnesium sulfate and evaporated. The resulting residue was purified by silica gel column chromatography, to give ent-19-methoxy-15β, 17-bis{(methoxymethyl)oxy}-16α-atisane (6.1 mg).

$^1$H NMR (CDCl$_3$); δ (ppm) 0.61–0.76 (1H, m), 0.83–1.94 (19H, m), 0.95 (3H, s), 0.96 (3H, s), 2.56 (1H, d, J=3.6 Hz), 3.18 (1H, d, J=9.2 Hz), 3.30 (3H, s), 3.36 (3H, s), 3.36–3.43 (1H, m), 3.39 (3H, s), 3.43 (1H, d, J=9.2 Hz), 3.64 (1H, dd, J=9.8, 5.4 Hz), 4.56 (1H, d, J=6.8 Hz), 4.61 (1H, d, J=6.6 Hz), 4.64 (1H, d, J=6.6 Hz), 4.80 (1H, d, J=6.8 Hz)

Example 40 ent-15β,17-dihydroxy-19-methoxy-16α-atisane

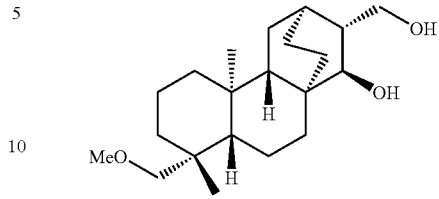

From ent-19-methoxy-15β,17-bis{(methoxymethyl)oxy}-16α-atisane (12.8 mg, 0.0302 mmol) obtained in Example 39, ent-15β,17-dihydroxy-19-methoxy-16α-atisane (14 mg) was obtained in the same manner as described in Example 36.

$^1$H NMR (CDCl$_3$); δ (ppm) 0.66–0.77 (1H, m), 0.78–1.81 (18H, m), 0.95 (3H, s) 0.97 (3H, s), 1.84–1.96 (1H, m), 2.94 (1H, d, J=4.4 Hz), 3.18 (1H, d, J=9.2 Hz) 3.30 (3H, s), 3.42 (1H, d, J=9.2 Hz), 3.62 (1H, dd, J=10.0 and 7.2 Hz) 3.68 (1H, dd, J=10.0 and 8.2 Hz)

Example 41 ent-15β-hydroxy-19-methoxy-17-methylthio-16α-atisane

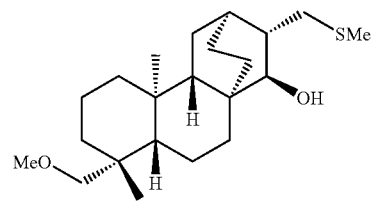

From ent-15β,17-dihydroxy-19-methoxy-16α-atisane (14 mg) obtained in Example 40, ent-15β-hydroxy-19-methoxy-17-methylthio-16α-atisane (6.4 mg) was obtained in the same manners as described in Example 4 and Example 7.

$^1$H NMR (CDCl$_3$); δ (ppm) 0.65–0.77 (1H, m), 0.84–1.98 (19H, m), 0.95 (3H, s) 0.96 (3H, s), 2.14 (3H, s), 2.50–2.57 (2H, m), 2.92 (1H, d, J=4.0 Hz) 3.18 (1H, d, J=8.8 Hz), 3.30 (3H, s), 3.42 (1H, d, J=8.8 Hz)

Example 42 ent-15β-Hydroxy-19-methoxy-17-methylsulfinyl-16α-atisane

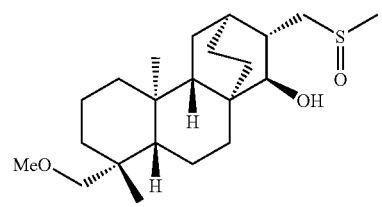

From ent-15β-hydroxy-19-methoxy-17-methylthio-16α-atisane (4.3 mg) obtained in Example 41, ent-15β-hydroxy-19-methoxy-17-methylsulfinyl-16α-atisane (3.2 mg) was obtained in the same manner as described in Example 6.

ESI-MS:m/z=405 (M+Na)+ 1H NMR (CD3OD); δ (ppm) 0.73–2.01 (20H, m), 0.94 (3H, s), 1.01 (3H, s) 2.67 and 2.69 (3H, s×2), 2.78–3.03 (3H, m), 3.21 (1H, d, J=9.2 Hz), 3.28 (3H, s) 3.46 (1H, d, J=9.2 Hz)

Example 43 ent-15β,17-Bis{(methoxymethyl)oxy}-19-oxo-16α-atisane

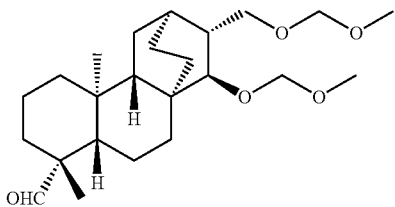

To a solution of ent-19-hydroxy-15β,17-bis{(methoxymethyl)oxy}-16α-atisane (9.2 mg, 0.0224 mmol) obtained in Example 34 in dichloromethane (0.5 mL) were added tetrapropyl ammonium perruthenate (0.4 mg, 0.0011 mmol), N-methylmorpholine-N-oxide (3.9 mg, 0.033 mmol) and 4A molecular sieve (powder) (11.2 mg) under stirring at room temperature. After stirring at room temperature for 1 hour, isopropyl alcohol (0.05 mL) was added thereto. The mixture was stirred at room temperature for 10 minutes and then evaporated. The resulting residue was purified by silica gel column chromatography, to give ent-15β,17-bis{(methoxymethyl)oxy}-19-oxo-16α-atisane (11.7 mg, colorless oil).

1H NMR (CDCl3); δ (ppm) 0.68–1.99 (19H, m), 0.84 (3H, s), 1.01 (3H, s) 2.08–2.17 (1H, m), 2.66 (1H, d, J=3.2 Hz), 3.36 (3H, s), 3.37–3.44 (1H, m), 3.40 (3H, s) 3.60–3.66 (1H, m), 4.57 (1H, d, J=6.8 Hz), 4.62 (1H, d, J=6.6 Hz), 4.65 (1H, d, J=6.6 Hz) 4.82 (1H, d, J=6.8 Hz), 9.78 (1H, s)

Example 44 ent-15β,17-Dihydroxy-19-oxo-16α-atisane

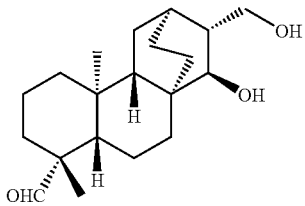

From ent-15β,17-bis{(methoxymethyl)oxy}-19-oxo-16α-atisane (11.7 mg, 0.0287 mmol) obtained in Example 43, ent-15β,17-dihydroxy-19-oxo-16α-atisane (13.1 mg, pale yellow crude oil) was obtained in the same manner as described in Example 36.

1H NMR (CDCl3); δ (ppm) 0.71–1.90 (18H, m), 0.85 (3H, s), 1.01 (3H, s) 1.91–2.01 (1H, m), 2.09–2.17 (1H, m), 2.99 (1H, d, J=4.4 Hz), 3.56–3.73 (2H, m) 9.77 (1H, s)

Example 45 ent-15β-Hydroxy-17-methylthio-19-oxo-16α-atisane

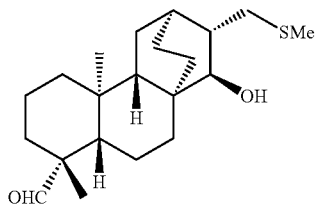

From ent-15β,17-dihydroxy-19-oxo-16α-atisane (13.1 mg, 0.0409 mmol) obtained in Example 44, ent-15β-hydroxy-17-methylthio-19-oxo-16α-atisane (6.4 mg, pale yellow amorphous) was obtained in the same manners as described in Example 4 and Example 7.

1H NMR (CDCl3); δ (ppm) 0.71–2.17 (20H, m) 0.843 (3H, s), 1.014 (3H, s) 2.147 (3H, s), 2.531 (2H, d, J=8.0 Hz), 2.965 (1H, d, J=4.0 Hz), 9.77 (1H, s)

Example 46 ent-15β-Hydroxy-17-methylsulfinyl-19-oxo-16α-atisane

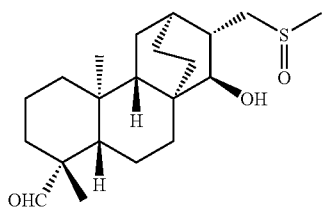

From ent-15β-hydroxy-17-methylthio-19-oxo-16α-atisane (2.0 mg, 0.0057 mmol) obtained in Example 45, ent-15β-hydroxy-17-methylsulfinyl-19-oxo-16α-atisane (2.19 mg) was obtained in the same manner as described in Example 6.

ESI-MS:m/z=389 (M+Na)+ 1H NMR (CD3OD); δ (ppm) 0.79–2.14 (20H, m), 0.87 (3H, s), 1.00 (3H, s) 2.67 and 2.69 (3H, s×2), 2.79–3.03 (3H, m), 9.77 (1H, s)

Example 47 ent-19-Dimethylamino-15β-hydroxy-17-methylthio-16α-atisane

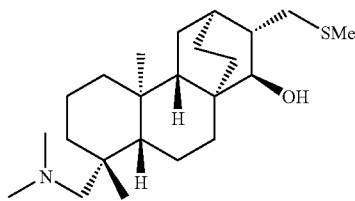

To a suspension of lithium aluminum hydride (14.7 mg, 0.387 mmol) in tetrahydrofuran (2.0 mL) was added aluminum chloride (51.6 mg, 0.387 mmol) under stirring at room temperature. After stirring at room temperature for 20 minutes, the reaction mixture was ice-cooled. A solution of ent-15β-hydroxy-17-methylthio-16α-atisane-19-dimethylamide obtained by Example 26 (15.2 mg, 0.0387 mmol) in tetrahydrofuran (1.5 mL) was added thereto, followed by stirring for 2 hours at room temperature. The reaction mixture was again ice-cooled and a27% aqueous ammonium was added thereto, followed by stirring for 5 minutes at room temperature. Then, the resulting solid was filtered off through Celite, and the filtrate was evaporated. The resulting residue was purified by silica gel column chromatography, to give ent-19-dimethylamino-15β-hydroxy-17-methylthio-16α-atisane (22 mg, colorless oil).

ESI-MS:m/z=380 (M+H)$^{+1}$H NMR (CD$_3$OD); δ (ppm) 0.68–0.80 (1H, m), 0.84–1.95 (19H, m), 1.02 (3H, s) 1.13 (3H, s), 2.08 (3H, s), 2.48 (1H, dd, J=13.0 amd 9.4 Hz) 2.64 (1H, dd, J=13.0 and 6.8 Hz), 2.68–2.90 (7H, m)

Example 48 ent-19-Dimethylamino-15β-hydroxy-17-methylsulfinyl-16α-atisane

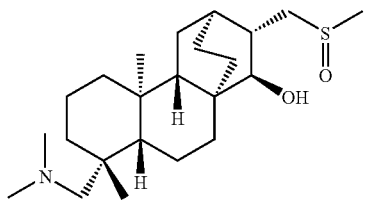

From hydrochloride of ent-19-dimethylamino-15β-hydroxy-17-methylthio-16α-atisane (7.9 mg, 0.019 mmol) obtained in Example 47, ent-19-dimethylamino-15β-hydroxy-17-methylsulfinyl-16α-atisane (3.1 mg) was obtained in the same manner as described in Example 6.

ESI-MS:m/z=396 (M+H)$^{+1}$H NMR (CD$_3$OD); δ (ppm) 0.74–2.20 (20H, m), 0.98 (3H, s), 1.02 (3H, s), 2.30 (6H, s) 2.67 and 2.68 (3H, s×2), 2.78–3.03 (3H, m)

Example 49

(1R,4S,5S,9S,10S,12R,13R,14R)-5-Isocyanate-5,9-dimethyl-13-{(methylsulfanyl)methyl}tetracyclo[10.2.2.0$^{1,10}$.0$^{4,9}$]hexadecy-14-yl acetate

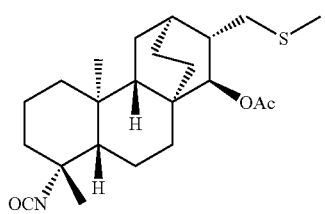

To a solution of ent-15β-acetoxy-17-methylthio-16α-atisane-19-oic acid (27.8 mg, 0.0682 mmol) obtained in Example 17 in toluene (1.36 mL) were added diphenylphosphoryl azide (22 μl, 0.102 mmol) and triethylamine (14.3 μl, 0.103 mmol) were added under stirring at room temperature, followed by stirring for 7 hours at 90° C. After recovered to room temperature, the reaction mixture was diluted with ethyl acetate, washed with saturated brine, dried over magnesium sulfate and evaporated. The resulting residue was purified by silica gel column chromatography, to give (1R, 4S,5S,9S,10S,12R,13R,14R)-5-isocyanate-5,9-dimethyl-13-{(methylsulfanyl)methyl}tetracyclo[10.2.2.0$^{1,10}$.0$^{4,9}$]hexadecy-14-yl acetate (17.8 mg).

$^1$H NMR (CDCl$_3$); δ (ppm) 0.80–2.12 (20H, m), 1.12 (3H, s), 136 (3H, s), 2.08 (3H, s) 2.10 (3H, s), 2.51 (1H, dd, J=12.8 and 10.4 Hz), 2.84 (1H, dd, J=12.8 and 5.8 Hz) 4.17 (1H, d, J=4.0 Hz)

Example 50

(1R,4S,5S,9S,10S,12R,13R,14R)-5-{(t-butoxycarbonyl)amino}-5,9-dimethyl-13-{(methylsulfanyl)methyl}tetracyclo[10.2.2.0$^{1,10}$.0$^{4,9}$]hexadecy-14-yl acetate

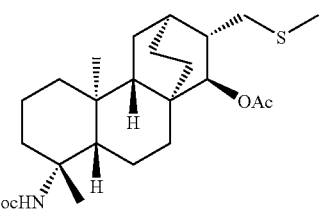

(1R,4S,5S,9S,10S,12R,13R,14R)-5-isocyanate-5,9-dimethyl-13-{(methylsulfanyl)methyl}tetracyclo[10.2.2.0$^{1,10}$.0$^{4,9}$]hex adecy-14-yl acetate (8.2 mg, 0.0202 mmol) obtained in Example 49 was dissolved in 0.025N hydrochloric acid-dichloromethane (1 mL). Under stirring at room temperature, t-butylalcohol (40 μl, 0.418 mmol) was added thereto, followed by stirring at room temperature for 6 hours. Then, water was added thereto and the mixture was extracted twice with diethyl ether. The resulting organic layer was washed with saturated brine, dried over magnesium sulfate and evaporated. The resulting residue was purified by silica gel column chromatography, to give (1R, 4S,5S,9S,10S,12R,13R,14R)-5-{(t-butoxycarbonyl)amino}-5,9-dimethyl-13-{(methylsulfanyl)methyl}tetracyclo[10.2.2.0$^{1,10}$.0$^{4,9}$]hexadecy-14-yl acetate (6.8 mg).

$^1$H NMR (CDCl$_3$); δ (Ppm) 0.78–2.04 (19H, m), 1.10 (3H, s), 1.25 (3H, s), 1.42 (9H, s) 2.07 (3H, s), 2.11 (3H, s), 2.45 (1H, dd, J=12.6 and 10.6 Hz), 2.55–2.65 (1H, m) 2.85 (1H, dd, J=12.6 and 5.8 Hz), 4.16 (1H, d, J=4.0 Hz), 4.41 (1H, broad s)

Example 51 t-Butyl N-(1R,4S,5S,9R,10S,12R,13R,14R)-14-hydroxy-5,9-dimethyl-13-{(methylsulfanyl)methyl}tetracyclo[10.2.2.0$^{1,10}$.0$^{4,9}$]hexadecy-14-yl carbamate

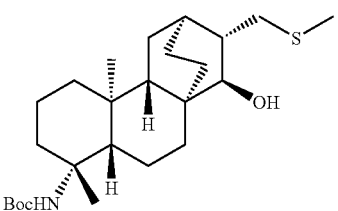

From (1R,4S,5S,9S,10S,12R,13R,14R)-5-{(t-butoxycarbonyl)amino}-5,9-dimethyl-13-{(methylsulfanyl)methyl}tetracyclo[10.2.2.0$^{1,10}$.0$^{4,9}$]hexadecy-14-yl acetate (6.8 mg, 0.0141 mmol) obtained in Example 50, t-butyl N-(1R,4S,5S,9R,10S,12R,13R,14R)-14-hydroxy-5,9-dimethyl-13-{(methylsulfanil)methyl}tetracyclo[10.2.2.0$^{1,10}$.0$^{4,9}$]hexadecy-14-yl carbamate (4.9 mg, colorless amorphous) was obtained in the same manner as described in Example 19.

$^{1}$H NMR (CDCl$_3$); δ (ppm) 0.66–2.04 (19H, m), 1.10 (3H, s), 1.25 (3H, s), 1.42 (9H, s) 2.14 (3H, s), 2.53 (2H, d, J=8.0 Hz), 2.55–2.65 (1H, m), 2.95 (1H, d, J=4.0 Hz), 4.43 (1H, broad s)

Example 52 t-Butyl N-(1R,4S,5S,9R,10S,12R,13R,14R)-14-hydroxy-5,9-dimethyl-13-{(methylsulfanil)methyl}tetracyclo[10.2.2.0$^{1,10}$.0$^{4,9}$]hexadecy-5-yl carbamate

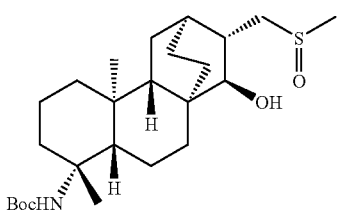

From t-butyl N-(1R,4S,5S,9R,10S,12R,13R,14R)-14-hydroxy-5,9-dimethyl-13-{(methylsulfanyl)methyl}tetracyclo[10.2.2.0$^{1,10}$.0$^{4,9}$]hexadecy-14-yl carbamate (4.9 mg, 0.0112 mmol) obtained in Example 51, t-butyl N-(1R,4S,5S,9R,10S,12R,13R,14R)-14-hydroxy-5,9-dimethyl-13-{(methylsulfanyl)methyl}tetracyclo[10.2.2.0$^{1,10}$.0$^{4,9}$]hexadecy-5-yl carbamate (3.9 mg) was produced in the same manner as described in Example 6.

ESI-MS:m/z=454 (M+H)$^{+1}$H NMR (CD$_3$OD); δ (ppm) 0.77–2.09 (19H, m), 1.13 (3H, s), 1.32 (3H, s), 1.42 (9H, s) 2.50–2.60 (1H, m), 2.67 and 2.69 (3H, s×2), 2.78–3.04 (3H, m)

Example 53

(1R,4S,5S,9R,10S,12R,13R,14R)-5-amino-5,9-dimethyl-13-{(methylsulfinyl)methyl}tetracyclo[10.2.2.0$^{1,10}$.0$^{4,9}$]hexadecane-14-ol

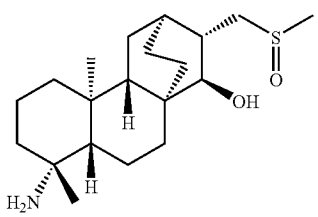

To a solution of t-butyl N-(1R,4S,5S,9R,10S,12R,13R,14R)-14-hydroxy-5,9-dimethyl-13-{(methylsulfanyl)methyl}tetracyclo[10.2.2.0$^{1,10}$.0$^{4,9}$]hexadecy-5-yl carbamate (3.9 mg, 0.00860 mmol) obtained in Example 52 in dichloromethane (1 mL) was added trifluoroacetic acid (1 mL) under stirring at room temperature. After stirring at room temperature for 5 hours, the mixture was evaporated. The resulting residue was purified by NH-silica gel column chromatography, to give (1R,4S,5S,9R,10S,12R,13R,14R)-5-amino-5,9-dimethyl-13-{(methylsulfinyl)methyl}tetracyclo[10.2.2.0$^{1,10}$.0$^{4,9}$]hexadecane-14-ol (1.11 mg).

ESI-MS:m/z=354 (M+H)$^{+1}$H NMR (CD$_3$OD); δ (ppm) 0.78–2.04 (20H, m), 1.11 (3H, s), 1.14 (3H, s) 2.67 and 2.69 (3H, s×2), 2.78–3.03 (3H, m)

Example 54

Methyl ent-15β-methoxy-17-methylsulfinyl-16α-atisane-19-oate

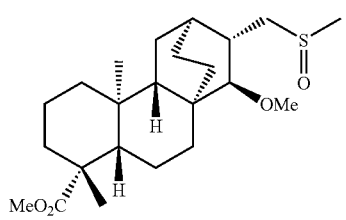

To a mixed solution of isomers 1 and 2 of ent-15β-hydroxy-17-methylsulfinyl-16α-atisane-19-oic acid (18.7 mg, 0.0490 mmol) obtained in Example 6 in dimethyl formamide (1 mL) were added sodium hydride (60% dispersion in mineral oil) (9.8 mg, 0.245 mmol) and iodomethane (15 μl, 0.24 mmol) under stirring on ice, followed by stirring for 3 hours at room temperature. After adding saturated aqueous ammonium chloride, the mixture was extracted twice with ethyl acetate. The resulting organic layer was washed with saturated brine, dried over magnesium sulfate and evaporated. The resulting residue was purified by silica gel column chromatography, to give methyl ent-15β-methoxy-17-methylsulfinyl-16α-atisane-19-oate (18.1 mg, pale yellow oil).

ESI-MS:m/z=433 (M+Na)$^{+1}$H NMR (CD$_3$OD); δ (ppm) 0.77–2.18 (20H, m), 0.81 (3H, s), 1.17 (3H, s) 2.50 (0.5H, d, J=4.0 Hz), 2.55 (0.5H, d, J=4.0 Hz), 2.67 and 2.69 (3H, s×2) 2.78–3.01 (2H, m), 3.40 and 3.45 (3H, s×2), 3.63 (3H, s)

Example 55 ent-15β-Methoxy-17-methylsulfinyl-16α-atisane-19-oic acid

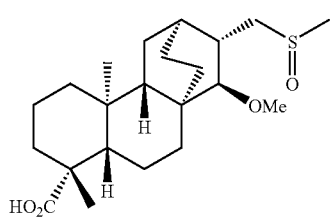

From methyl ent-15β-methoxy-17-methylsulfinyl-16α-atisane-19-oate (18.1 mg, 0.0441 mmol) obtained in Example 54, ent-15β-methoxy-17-methylsulfinyl-16α-atisane-19-oic acid (10.9 mg, pale yellow crystals) was obtained in the same manner as described in Example 7.

ESI-MS:m/z=419 (M+Na)$^{+1}$H NMR (CD$_3$OD); δ (ppm) 0.66–2.25 (20H, m), 0.84 (3H, s), 1.09 (3H, s) 2.40 (0.5H, d, J=3.2 Hz), 2.45 (1H, d, J=2.8 Hz), 2.58 and 2.59 (3H, s×2) 2.69–2.93 (2H, m), 3.31 and 3.36 (3H, s×2)

Example 56 ent-17-Methylsulfinyl-15-oxo-16α-atisane-19-oic acid

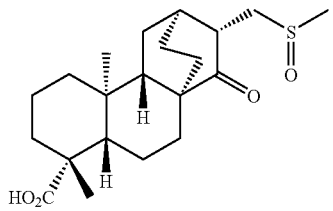

To a mixed solution of isomers 1 and 2 of ent-15β-hydroxy-17-methylsulfinyl-16α-atisane-19-oic acid (8.56 mg, 0.0224 mmol) obtained in Example 6 in dichloromethane (1 mL) was added Dess-Martin iodinane (19.2 mg, 0.0448 mmol) under stirring on ice, followed by stirring for 4 hours under ice-cooling. Then, saturated aqueous sodium thiosulfate was added thereto and the mixture was extracted twice with ethyl acetate. The resulting organic layer was washed with saturated brine, dried over magnesium sulfate and evaporated. The resulting residue was purified by silica gel column chromatography, to give ent-17-methylsulfinyl-15-oxo-16α-atisane-19-oic acid (4.35 mg).

ESI-MS:m/z=403 (M+Na)$^+$ $^1$H NMR (CD$_3$OD); δ (ppm) 0.95 and 0.96 (3H, s×2), 1.11 (3H, s) 2.58 and 2.59 (3H, s×2), 2.74 (0.5H, dd, J=13.4 and 7.0 Hz) 2.85 (0.5H, dd, J=13.4 and 10.8 Hz), 3.00–3.10 (1H, m)

Example 57

N1-(1R,4S,5S,9R,10S,12R,13R,14R)-14-Hydroxy-5,9-dimethyl-13-{(methylsulfanyl)methyl}tetracyclo[10.2.2.0$^{1,10}$.0$^{4,9}$]hexadecy-14-yl acetamide

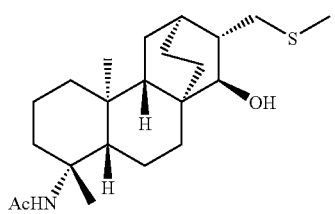

To a solution of (1R,4S,5S,9S,10S,12R,13R,14R)-5-isocyanate-5,9-dimethyl-13-{(methylsulfanyl)methyl}tetracyclo[10.2.2.0$^{1,10}$.0$^{4,9}$]hexadecy-14-yl acetate (17.8 mg, 0.0440 mmol) obtained in Example 49 in diethyl ether (1.5 mL) was added 1.03M methyl lithium diethyl ether solution (0.13 mL, 0.134 mmol) under stirring on ice, followed by stirring for 3 hours at room temperature. After adding saturated ammonium chloride aqueous solution, the mixture was extracted twice with ethyl acetate. The resulting organic layer was washed with saturated brine, dried over magnesium sulfate and evaporated. The resulting residue was purified by silica gel column chromatography, to give N1-(1R,4S,5S,9S,10S,12R,13R,14R)-14-hydroxy-5,9-dimethyl-13-{(methylsulfanyl)methyl}tetracyclo[10.2.2.0$^{1,10}$.0$^{4,9}$]hexadecy-5-yl acetamide (12.4 mg).

$^1$H NMR (CDCl$_3$); δ (ppm) 0.73–2.10 (19H, m), 1.11 (3H, s), 1.40 (3H, s), 1.93 (3H, s) 2.15 (3H, s), 2.53 (2H, d, J=8.0 Hz), 2.72–2.82 (1H, m), 2.95 (1H, d, J=4.0 Hz) 5.25 (1H, broad s)

Example 58

N1-(1R,4S,5S,9R,10S,12R,13R,14R)-14-Hydroxy-5,9-dimethyl-13-{(methylsulfinyl)methyl}tetracyclo[10.2.2.0$^{1,10}$.0$^{4,9}$]hexadecy-5-yl acetamide

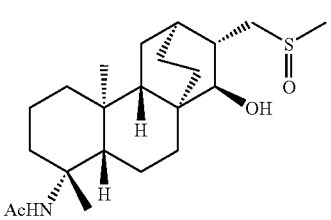

From N1-(1R,4S,5S,9R,10S,12R,13R,14R)-14-hydroxy-5,9-dimethyl-13-{(methylsulfanyl)methyl}tetracyclo[10.2.2.0$^{1,10}$.0$^{4,9}$]hexadecy-5-yl acetamide (8.99 mg, 0.0237 mmol) obtained in Example 57, N1-(1R,4S,5S,9R,10S,12R,13R,14R)-14-hydroxy-5,9-dimethyl-13-{(methylsulfinyl)methyl}tetracyclo[10.2.2.0$^{1,10}$.0$^{4,9}$]hexadecy-5-yl acetamide (8.2 mg, colorless amorphous) was obtained in the same manner as described in Example 7.

ESI-MS:m/z=418 (M+Na)$^+$ $^1$H NMR (CD$_3$OD); δ (ppm) 1.14 (3H, s) 1.37 (3H, s), 2.67 and 2.69 (3H, s×2) 2.78–3.30 (3H, m)

Example 59

N-Methoxy-N-methyl ent-15β-acetoxy-17-methylthio-16α-atisane-19-amide

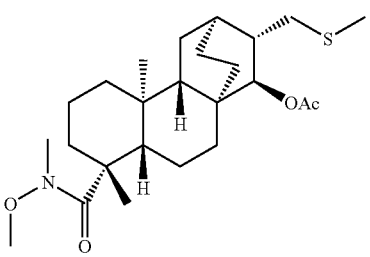

To a solution of ent-15β-acetoxy-17-methylthio-16α-atisane-19-oic acid (21.3 mg, 0.0523 mmol) obtained in Example 17 in dichloromethane (1 mL) was added oxalyl chloride (14 μl, 0.16 mmol) was added under stirring once. After stirring at room temperature for 2 hours, the reaction mixture was ice-cooled, and N,O-dimethylhydroxy-amine hydrochloride (25.5 mg, 0.261 mmol), pyridine (0.5 mL) and dimethylaminopyridine (19.1 mg, 0.157 mmol) were added, followed by stirring for 4 hours at room temperature. After adding ethyl acetate, the mixture was washed with 1N hydrochloric acid, saturated aqueous sodium hydrogen carbonate and saturated brine, dried over magnesium sulfate and evaporated, to give N-methoxy-N-methyl ent-15β-acetoxy-17-methylthio-16α-atisane-19-amide (34.0 mg, pale yellow crude oil).

$^1$H NMR (CDCl$_3$); δ (ppm) 0.80–2.17 (20H, m), 0.92 (3H, s), 1.25 (3H, s) 2.08 (3H, s) 2.11 (3H, s), 2.45–2.88 (2H, m), 3.12 (3H, s), 3.65 (3H, s), 4.16 (1H, 3.6 Hz)

Example 60

1-(1R,4S,5S,9R,10S,12R,13R,14R)-14-Hydroxy-5,9-dimethyl-13-{(methylsulfanil)methyl}tetracyclo[10.2.2.0$^{1,10}$.0$^{4,9}$]hexadecy-5-yl-1-ethanone

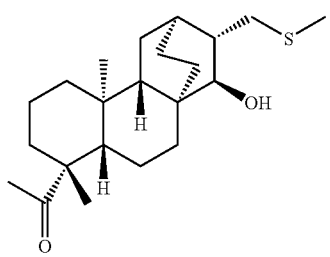

To a solution of N-methoxy-N-methyl ent-15β-acetoxy-17-methylthio-16α-atisane-19-amide (34.0 mg, 0.0753 mmol) obtained in Example 59 in tetrahydrofuran (2 mL) was added 1.03M methyl lithium diethyl ether solution (0.231 mL, 0.238 mmol) under stirring on ice. After stirring at 50° C. for 3 hours, the mixture was ice-cooled. 1N hydrochloric acid was added, and the mixture was extracted twice with ethyl acetate. The resulting organic layer was washed with saturated aqueous sodium hydrogen carbonate and saturated brine, dried over magnesium sulfate and evaporated. The resulting residue was purified by silica gel column chromatography, to give 1-(1R,4S,5S,9R,10S,12R,13R,14R)-14-hydroxy-5,9-dimethyl-13-{(methylsulfanil)methyl}tetracyclo[10.2.2.0$^{1,10}$.0$^{4,9}$]hexadecy-5-yl-1-ethanone (3.35 mg).

$^1$H NMR (CDCl$_3$); δ (ppm) 0.70–2.20 (20H, m), 0.77 (3H, s), 1.11 (3H, s), 2.15 (3H, s) 2.18 (3H, s), 2.51–2.56 (2H, m), 2.96 (1H, d, J=3.6 Hz)

Example 61

1-(1R,4S,5S,9R,10S,12R,13R,14R)-14-Hydroxy-5,9-dimethyl-13-{(methylsulfinyl)methyl}tetracyclo[10.2.2.0$^{1,10}$.0$^{4,9}$]hexadecy-5-yl-1-ethanone

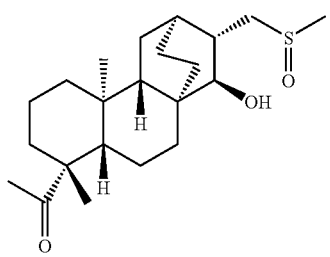

From 1-(1R,4S,5S,9R,10S,12R,13R,14R)-14-hydroxy-5,9-dimethyl-13-{(methylsulfanyl)methyl}tetracyclo[10.2.2.0$^{1,10}$.0$^{4,9}$]hexadecy-5-yl-1-ethanone (3.35 mg, 0.00919 mmol) obtained in Example 60, 1-(1R,4S,5S,9R,10S,12R,13R,14R)-14-hydroxy-5,9-dimethyl-13-{(methylsulfinyl)methyl}tetracyclo[10.2.2.0$^{1,10}$.0$^{4,9}$]hexadecy-5-yl-1-ethanone (1.63 mg) was obtained in the same manner as described in Example 6.

ESI-MS:m/z=403 (M+Na)$^+$ $^1$H NMR (CD$_3$OD); δ (ppm) 0.64–2.12 (20H, m), 0.72 (3H, s), 1.03 (3H, s), 2.10 (3H, s) 2.58 and 2.59 (3H, s×2), 2.69–2.94 (3H, m)

Example 62 ent-15β-Hydroxy-17-propylthio-16α-atisane-19-oic acid

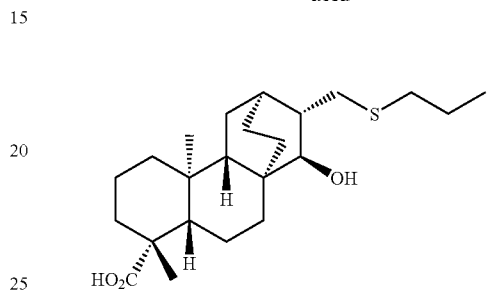

To a solution of propanethiol (72 μl, 0.80 mmol) in hexamethylphosphoramide (3 mL) was added sodium hydride (60% dispersion in mineral oil) (32 mg, 0.80 mmol) under stirring at room temperature, followed by stirring at room temperature for 10 minutes. Then, methyl ent-15β-hydroxy-17-tosyloxy-16α-atisane-19-oate (40.0 mg, 0.0793 mmol) obtained in Example 4 was added thereto, followed by stirring for 2 hours at 50° C. in nitrogen atmosphere. The reaction was recovered to room temperature, and saturated aqueous ammonium chloride was added, and the mixture was extracted twice with ethyl acetate. The resulting organic layer was washed with saturated brine, dried over magnesium sulfate and evaporated. The resulting residue was purified by silica gel column chromatography, to give ent-15β-hydroxy-17-propylthio-16α-atisane-19-oic acid (32.0 mg, pale yellow oil).

ESI-MS:m/z=393 (M–H)$^-$ $^1$H NMR (CDCl$_3$); δ (ppm) 0.68–0.80 (1H, m), 0.91 (3H, s), 1.00 (3H, t, J=7.6 Hz) 0.88–1.92 (19H, m), 1.93–2.04 (1H, m), 2.15 (1H, d, J=14.0 Hz), 2.48–2.59 (4H, m) 2.95 (1H, d, J=4.0 Hz)

Example 63 ent-15β-Hydroxy-17-propylsulfinyl-16α-atisane-19-oic acid

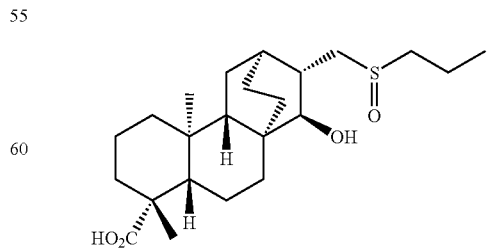

From ent-15β-hydroxy-17-propylthio-16α-atisane-19-oic acid (30.6 mg, 0.0777 mmol) obtained in Example 62, ent-15β-hydroxy-17-propylsulfinyl-16α-atisane-19-oic acid (21.8 mg) was obtained in the same manner as described in Example 6.

ESI-MS:m/z=433 (M+Na)+

$^1$H NMR (CD$_3$OD); δ (ppm) 0.75–0.87 (1H, m), 0.87–1.96 (22H, m), 0.95 (3H, s) 1.19 (3H, s), 1.96–2.07 (1H, m), 2.08–2.17 (1H, m), 2.72–3.00 (5H, m)

Example 64

Ethyl (ent-15β,17-bis{(methoxymethyl)oxy}-16α-atisane-19-ylidene) acetate

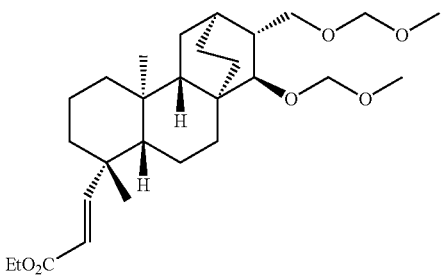

To a solution of triethylphosphonoacetate (82 μl, 0.413 mmol) in tetrahydrofuran (2 mL) was added sodium hydride (60% dispersion in mineral oil) (16.6 mg, 0.415 mmol) under stirring on ice, followed by stirring for 1 hour at room temperature. Under ice-cooling, ent-15β,17-bis{(methoxymethyl)oxy}-19-oxo-16α-atisane (33.9 mg, 0.0831 mmol) obtained in Example 43 in tetrahydrofuran (2 mL) was added, followed by stirring for 15 hours at room temperature. Saturated aqueous ammonium chloride was added, and the mixture was extracted twice with ethyl acetate. The resulting organic layer was washed with saturated brine, dried over magnesium sulfate and evaporated. The resulting residue was purified by silica gel column chromatography, to give ethyl (ent-15β,17-bis{(methoxymethyl)oxy)-16α-atisane-19-ylidene) acetate (21.0 mg).

$^1$H NMR (CDCl$_3$); δ (ppm) 0.66–0.78 (1H, m), 0.80–1.98 (19H, m), 0.85 (3H, s) 1.00 (3H, s), 1.30 (3H, t, J=7.2 Hz), 2.64 (1H, d, J=3.2 Hz), 3.36 (3H, s), 3.39 (3H, s) 3.63 (1H, dd, J=9.4 and 5.4 Hz), 4.19 (2H, q, J=7.2 Hz), 4.56 (1H, d, J=6.4 Hz) 4.61 (1H, d, J=6.4 Hz), 4.64 (1H, d, J=6.4 Hz), 4.81 (1H, d, J=6.4 Hz) 5.75 (1H, d. J=15.8 Hz), 7.16 (1H, d, J=15.8 Hz)

Example 65

Ethyl (ent-15β,17-bis{(methoxymethyl)oxy}-16α-atisane-19-yl)acetate

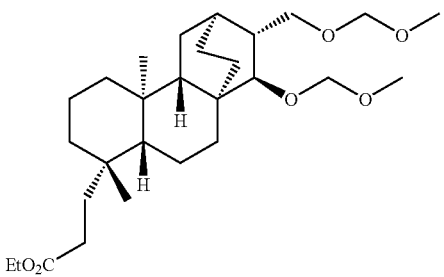

To a solution of ethyl (ent-15β,17-bis{(methoxymethyl)oxy}-16α-atisane-19-ylidene) acetate (21 mg, 0.044 mmol) obtained in Example 64 in ethanol (2 mL) was added 10% palladium carbon (containing 50% water) (21 mg), followed by conducting catalytic hydrogen reduction at normal temperature and normal pressure for 19 hours. The reaction solution was filtrated through Celite and the filtrate was evaporated, to give ethyl (ent-15β,17-bis{(methoxymethyl)oxy}-16α-atisane-19-yl)acetate (25 mg).

$^1$H NMR (CDCl$_3$); δ (ppm) 0.64–0.75 (1H, m), 0.84 (3H, s), 1.02 (3H, s) 1.26 (3H, t, J=7.2 Hz), 2.61 (1H, d, J=3.2 Hz), 3.36 (3H, s), 3.39 (3H, s) 3.60–3.66 (1H, m), 4.12 (1H, q, J=7.2 Hz), 4.45 (1H, d, J=6.8 Hz), 4.61 (1H, d, J=6.8 Hz) 4.64 (1H, d, J=6.8 Hz), 4.80 (1H, d, J=6.8 Hz)

Example 66

Methyl ent-17-mesyloxy-15-atisene-19-oate

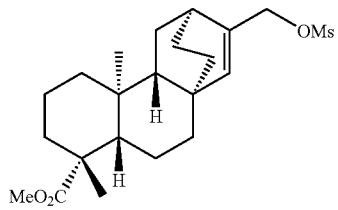

From methyl ent-17-hydroxy-15-atisene-19-oate (11 mg, 0.033 mmol) obtained in Example 1, methyl ent-17-mesyloxy-15-atisene-19-oate (13.2 mg) was obtained in the same manner as described in Example 14.

$^1$H NMR (CDCl$_3$); δ (ppm) 0.60–2.58 (19H, m), 0.80 (3H, s), 1.18 (3H, s) 3.10 (3H, s), 3.65 (3H, s), 4.69 (2H, s), 5.96 (1H, s)

Example 67

Methyl ent-17-methylthio-15-atisene-19-oate

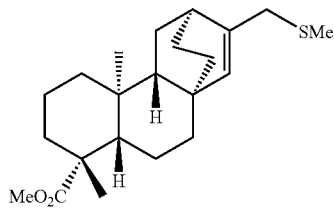

From methyl ent-17-mesyloxy-15-atisene-19-oate (13.2 mg, 0.032 mmol) obtained in Example 66, methyl ent-17-methylthio-15-atisene-19-oate (5.5 mg) was obtained in the same manner as described in Example 7.

$^1$H NMR (CDCl$_3$); δ (ppm) 0.76–2.03 (17H, m), 0.80 (3H, s), 1.19 (3H, s), 1.95 (3H, s), 2.15 (1H, d, J=16.8 Hz), 2.50 (1H, bs), 3.11 (2H, s), 3.65 (3H, s), 5.74 (1H, s)

Example 68 ent-17-Methylthio-15-atisene-19-oic acid

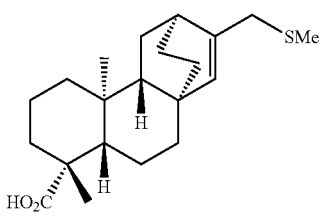

From methyl ent-17-methylthio-15-atisene-19-oate (5.5 mg, 0.015 mmol) obtained in Example 67, ent-17-methylthio-15-atisene-19-oic acid (2.1 mg) was obtained in the same manner as described in Example 5.

$^1$H NMR (CDCl$_3$) δ (ppm) 0.81–1.09 (16H, m), 0.92 (3H, s), 1.26 (3H, s), 1.95 (3H, s), 2.14 (1H, d, J=14.8 Hz), 2.51 (1H, bs), 3.11 (2H, s), 5.74 (1H, s)

Example 69 ent-17-Methylsulfinyl-15-atisene-19-oic acid

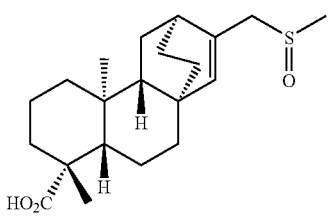

From ent-17-methylthio-15-atisene-19-oic acid (2.1 mg, 0.006 mmol) obtained in Example 68, ent-17-methylsulfinyl-15-atisene-19-oic acid (3.24 mg) was obtained in the same manner as described in Example 6.

ESI-MS:m/z=387 (M+Na)+

$^1$H NMR (CDCl$_3$); δ (ppm) 0.73–2.18 (18H, m), 0.92 (3H, s), 1.25 (3H, s), 2.53 (1H, s), 2.549, 2.553 (3H, s×2), 3.45–3.61 (2H, m), 6.01 (1H, s)

Example 70

Methyl ent-15β,17-dihydroxy-16β-atisane-19-oate

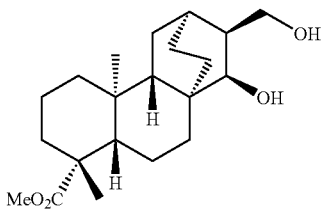

From methyl ent-15β-hydroxy-16-atisene-19-oate obtained by Example 1 (100 mg, 0.30 mmol), methyl ent-15β,17-dihydroxy-16β-atisane-19-oate (85 mg, white crystals) was obtained in the same manner as described in Example 2.

$^1$H NMR (CDCl$_3$); δ (ppm) 0.79 (3H, s), 0.85–2.11 (17H, m), 1.18 (3H, s), 2.14–2.19 (1H, m), 2.30–2.32 (1H, m), 2.50 (1H, d, J=4.2 Hz), 3.51–3.53 (1H, m), 3.60–3.65 (1H, m), 3.65 (3H, s), 3.97–4.04 (1H, m)

Example 71

Methyl ent-15β-hydroxy-17-tosyloxy-16β-atisane-19-oate

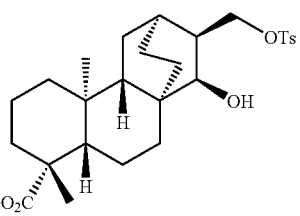

From methyl ent-15β,17-dihydroxy-16-atisane-19-oate (85 mg, 0.24 mmol) obtained in Example 70, methyl ent-15β-hydroxy-17-tosyloxy-16β-atisane-19-oate (85 mg, white crystals) was obtained in the same manner as described in Example 4.

$^1$H NMR (CDCl$_3$); δ (ppm) 0.76 (3H, s), 0.81–1.82 (17H, m), 1.16 (3H, s) 1.92 (1H, m), 2.16 (2H, m), 2.45 (3H, s), 3.42 (1H, dd, J=5.0, 9.2 Hz), 3.49 (1H, d, J=5.0 Hz), 3.64 (3H, s), 4.03 (1H, dd, J=8.0, 9.2 Hz), 4.40 (1H, dd, J=8.0, 10.0 Hz), 7.35 (2H, d, J=6.8 Hz), 7.80 (2H, d, J=6.8 Hz)

Example 72

Methyl ent-15β-hydroxy-17-methoxy-16α-atisane-19-oate

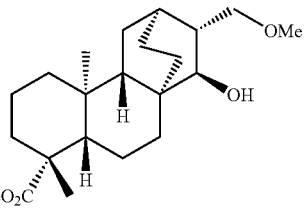

From methyl ent-15β,17-dihydroxy-16α-atisane-19-oate (29.3 mg, 0.084 mmol) obtained in Example 3, methyl ent-15β-hydroxy-17-methoxy-16α-atisane-19-oate (24.1 mg, white crystals) was obtained in the same manner as described in Example 39.

$^1$H NMR (CDCl$_3$); δ (ppm) 0.70–1.84 (18H, m), 0.80 (3H, s), 1.18 (3H, m), 1.93–2.00 (1H, m), 2.15 (1H, d, J=13.2 Hz), 2.93 (1H, d, J=4.0 Hz), 3.37 (2H, m), 3.37 (3H, s), 3.64 (3H, s)

Example 73 ent-15β-Hydroxy-17-methoxy-16α-atisane-19-oic acid

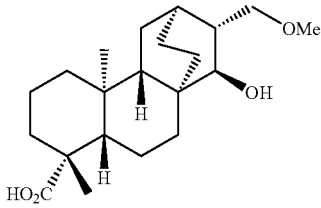

From methyl ent-15β-hydroxy-17-methoxy-16α-atisane-19-oate (9.1 mg, 0.025 mmol) obtained in Example 72, ent-15β-hydroxy-17-methoxy-16α-atisane-19-oic acid (8.4 mg, white crystals) was obtained in the same manner as described in Example 5.

ESI-MS:m/z=349 (M−H)+
$^1$H NMR (CDCl$_3$); δ (ppm) 0.70–2.02 (18H, m), 0.91 (3H, s), 1.24 (3H, s), 1.95–2.02 (1H, m), 2.16 (1H, d, J=4.0 Hz), 2.94 (1H, d, J=4.0 Hz), 3.37 (3H, s), 3.36–3.38 (2H, m)

Example 74 ent-15β-Hydroxy-17-methylthio-16α-atisane-19-oic acid

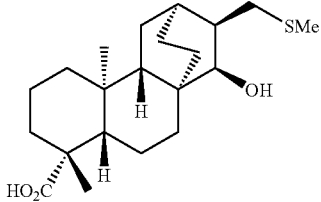

From methyl ent-15β-hydroxy-17-tosyloxy-16β-atisane-19-oate (85 mg, 0.17 mmol) obtained in Example 71, ent-15β-hydroxy-17-methylthio-16α-atisane-19-oic acid (49.1 mg, white crystals) was obtained in the same manner as described in Example 5.

ESI-MS:m/z=365 (M−H)+
$^1$H NMR (CDCl$_3$); δ (ppm) 0.85–2.17 (20H, m), 0.91 (3H, s), 1.24 (3H, s), 2.15 (3H, s), 2.52 (1H, dd, J=4.8, 12.0 Hz), 2.87 (1H, dd, J=11.6, 12.0 Hz), 3.46 (1H, d, J=8.4 Hz)

Example 75 ent-15β-Hydroxy-17-methylsulfinyl-16β-atisane-19-oic acid

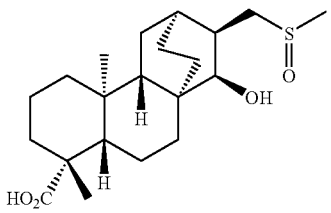

From ent-15β-hydroxy-17-methylthio-16α-atisane-19-oic acid (31.7 mg, 0.086 mmol) obtained in Example 74, ent-15β-hydroxy-17-methylsulfinyl-16β-atisane-19-oic acid was obtained in the same manner as described in Example 6. Furthermore, two isomers are separated according to the configuration of sulfoxides by means of silica gel column chromatography, to give isomer 1 (13.5 mg, white crystals) and isomer 2 (13.9 mg, white crystals).

(Isomer1)
ESI-MS:m/z=381 (M−H)+
$^1$H NMR (CDCl$_3$); δ (ppm) 0.88–2.41 (23H, m), 0.91 (3H, m), 1.24 (3H, s), 2.64 (3H, s), 3.44 (1H, d, J=8.4 Hz), 3.69 (1H, dd, J=12.2, 12.4 Hz)

(Isomer2)
ESI-MS:m/z=381 (M−H)+
$^1$H NMR (CDCl$_3$); δ (PPM) 0.89–2.17 (18H, m), 0.92 (3H, s), 1.24 (3H, s), 2.15 (1H, d, J=13.2 Hz), 2.29 (1H, dd, J=12.8, 13.6 Hz), 2.44–2.49 (1H, m), 2.59 (3H, s), 3.45 (1H, d, J=8.8 Hz), 3.65 (1H, dd, J=12.8, 12.8 Hz)

Example 76 ent-15β,17-Dihydroxy-16α-atisane-19-oic acid

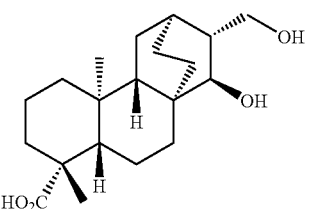

From methyl ent-15β,17-dihydroxy-16α-atisane-19-oate (29.6 mg, 0.084 mmol) obtained in Example 3, ent-15β,17-dihydroxy-16α-atisane-19-oic acid (22.1 mg, white crystals) was obtained in the same manner as described in Example 5.

ESI-MS:m/z=335 (M−H)+
$^1$H NMR (CDCl$_3$); δ (ppm) 0.65–0.73 (1H, m), 0.90–2.00 (18H, m), 0.94 (3H, s), 1.18 (3H, s), 2.12 (1H, d, J=13.6 Hz), 2.62 (1H, d, J=4.4 Hz), 3.39–3.45 (1H, m), 3.62–3.66 (1H, m)

Example 77 ent-15β-Hydroxy-17-tosyloxy-16α-atisane-19-oic acid

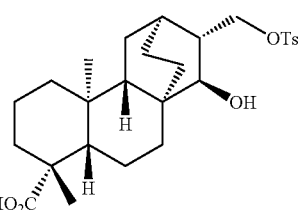

From ent-15β,17-dihydroxy-16α-atisane-19-oic acid (19.8 mg, 0.059 mmol) obtained in Example 76, ent-15β-hydroxy-17-tosyloxy-16α-atisane-19-oic acid (10.4 mg, white crystals) was obtained in the same manner as described in Example 4.

¹H NMR (CDCl₃); δ (ppm) 0.60–1.99 (19H, m), 0.88 (3H, s), 1.23 (3H, m), 2.15 (1H, d, J=12.4 Hz), 2.46 (3H, s), 2.81 (1H, d, J=4.4 Hz), 3.96 (1H, dd, J=9.2, 9.6 Hz), 4.05 (1H, dd, J=7.6, 9.6 Hz), 7.35 (2H, d, J=8.0 Hz), 7.80 (2H, d, J=8.0 (H,

Example 78 ent-17-Cyano-15β-hydroxy-16α-atisane-19-oic acid

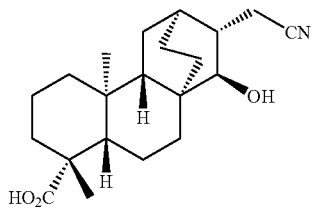

To a solution of ent-15β-hydroxy-17-tosyloxy-16α-atisane-19-oic acid (10.4 mg, 0.021 mmol) obtained in Example 77 in dimethylsulfoxide (2 mL) was added potassium cyanate (4.5 mg, 0.069 mmol), followed by stirring for 14 hours at 80° C. in nitrogen atmosphere. Then, the mixture was ice-cooled and water was added thereto. The mixture was extracted twice with ethyl acetate, and the resulting organic layer was washed with saturated brine, dried over magnesium sulfate and evaporated. The resulting residue was purified by silica gel column chromatography, to give ent-17-cyano-15β-hydroxy-16α-atisane-19-oic acid (1.3 mg).

ESI-MS:m/z=344 (M–H)⁺

¹H NMR (CDCl₃); δ (ppm) 0.71–0.79 (1H, m), 0.88–1.90 (17H, m), 0.92 (3H, s), 1.25 (3H, s), 2.00–2.07 (1H, m), 2.17 (1H, d, J=12.4 Hz), 2.34 (1H, dd, J=8.8, 16.6 Hz), 2.52 (1H, dd, J=7.6, 16.6 Hz), 2.90 (1H, d, J=4 Hz)

Example 79

Methyl ent-17-dimethylamino-15β-hydroxy-16α-atisane-19-oate

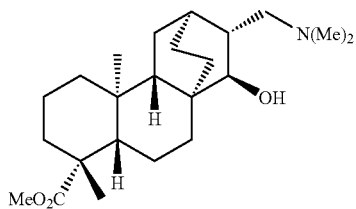

Methyl ent-15β-hydroxy-17-tosyloxy-16α-atisane-19-oate (10.67 mg, 0.021 mmol) obtained in Example 4 was dissolved in a solution of dimethylamine in a 2M tetrahydrofuran. After stirring for 34 hours at 140° C. in a sealed tube, methylene chloride was added thereto. The mixture was washed with a 1N aqueous sodium hydroxide and saturated brine, dried over magnesium sulfate and evaporated. The resulting residue was purified by silica gel column chromatography, to give methyl ent-17-dimethylamino-15β-hydroxy-16α-atisane-19-oate (5.1 mg).

ESI-MS:m/z=378 (M+H)⁺

¹H NMR (CDCl₃); δ (ppm) 0.79 (3H, s), 0.81–1.87 (18H, m), 1.18 (3H, s), 1.96–2.03 (1H, m), 2.47–2.52 (1H, m), 2.62 (6H, s), 2.76–2.82 (1H, m), 3.20 (1H, d, J=4.8 Hz), 3.64 (3H, s)

Example 80

Methyl ent-17-azido-15β-hydroxy-16α-atisane-19-oate

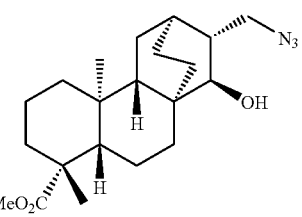

To a solution of methyl ent-15β-hydroxy-17-tosyloxy-16α-atisane-19-oate obtained in Example 4 (25.5 mg, 0.051 mmol) in dimethylformamide (1.5 mL) was added sodium azide (12.7 mg, 0.19 mmol) under stirring at room temperature, followed by stirring for 21 hours at 60° C. After recovering to room temperature, saturated aqueous ammonium chloride was added and the mixture was extracted twice with diethyl ether. The resulting organic layer was washed with saturated brine, dried over magnesium sulfate and evaporated. The resulting residue was purified by silica gel column chromatography, to give methyl ent-17-azido-15β-hydroxy-16α-atisane-19-oate (16.3 mg).

¹H NMR (CDCl₃); δ (ppm) 0.68–2.02 (19H, m), 0.80 (3H, s), 1.18 (3H, s), 2.16 (1H, d, J=14.4 Hz), 2.88 (1H, m), 3.28 (1H, dd, J=8.0, 12.0 Hz), 3.40 (1H, dd, J=8.0, 12.0 Hz), 3.65 (3H, S)

Example 81

Methyl ent-17-amino-15β-hydroxy-16α-atisane-19-oate

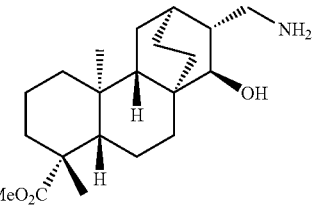

To a solution of methyl ent-17-azido-15β-hydroxy-16α-atisane-19-oate obtained by Example 80 (16.3 mg, 0.043 mmol) in ethanol (2 mL) was added Lindlar catalyst (6.52 mg), followed by stirring for 14 hours and 30 minutes in hydrogen atmosphere. After removing the Lindlar catalyst by filtration, the filtrate was evaporated, to give methyl ent-17-amino-15β-hydroxy-16α-atisane-19-oate (18.7 mg).

ESI-MS:m/z=350 (M+H)⁺

¹H NMR (CD₃OD); δ (ppm) 0.66–1.98 (19H, m), 0.82 (3H, s), 1.17 (3H, m), 2.14 (1H, d, J=13.6 Hz), 2.56–2.78 (3H, m), 3.63 (3H, s)

Example 82

Methyl ent-17-{(t-butoxycarbonyl)amino}-15β-hydroxy-16α-atisane-19-oate

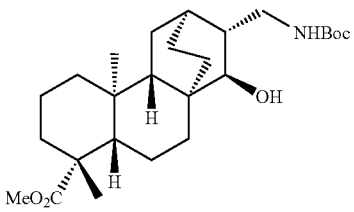

From methyl ent-17-amino-15β-hydroxy-16α-atisane-19-oate obtained by Example 81 (16.7 mg, 0.048 mmol), methyl ent-17-{(t-butoxycarbonyl)amino}-15β-hydroxy-16α-atisane-19-oate (21.6 mg) was obtained in the same manner as described in Example 30 (2).
$^1$H NMR (CDCl$_3$); δ (ppm) 0.70–1.87 (18H, m), 0.79 (3H, s), 1.18 (3H, s), 1.45 (9H, s), 1.93–2.00 (1H, m), 2.16 (1H, d, J=14.4 Hz), 2.89 (1H, d, J=3.2 Hz), 3.06–3.12 (1H, m), 3.17–3.23 (1H, m), 3.65 (3H, S), 4.75 (1H, bs)

Example 83 ent-17-{(t-Butoxycarbonyl)amino}-15β-hydroxy-16α-atisane-19-oic acid

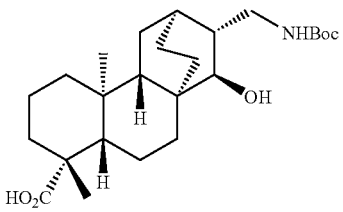

From methyl ent-17-{(t-butoxycarbonyl)amino}-15β-hydroxy-16α-atisane-19-oate (9.8 mg, 0.022 mmol) obtained in Example 82, ent-17-{(t-butoxycarbonyl)amino}-15β-hydroxy-16α-atisane-19-oic acid (3.06 mg) was obtained in the same manner as described in Example 5.
ESI-MS:m/z=434 (M−H)$^-$
$^1$H NMR (CDCl$_3$); δ (ppm) 0.71–0.79 (1H, m), 0.86–1.87 (17H, m), 0.91 (3H, s), 1.24 (3H, m), 1.45 (9H, s), 1.95–2.02 (1H, m), 2.16 (1H, d, J=13.6 Hz), 2.90 (1H, d, J=4 Hz), 3.05–3.12 (1H, m), 3.17–3.24 (1H, m), 4.76 (1H, bs)

Example 84 ent-17-Amino-15β-hydroxy-16α-atisane-19-oic acid-hydrochloric acid

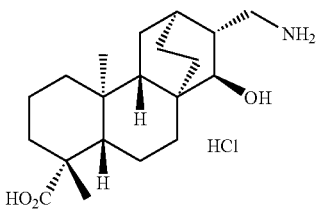

ent-17-{(t-Butoxycarbonyl)amino}-15β-hydroxy-16α-atisane-19-oic acid (1.92 mg, 0.0044 mmol) obtained in Example 83 was dissolved in a solution of 3N hydrogen chloride in ethyl acetate (1 mL), followed by stirring for 1 hour at room temperature. Then, the mixture was evaporated, to give ent-17-amino-15β-hydroxy-16α-atisane-19-oic acid-hydrochloric acid (1.98 mg).
ESI-MS:m/z=336 (M+H)$^+$
$^1$H NMR (CD$_3$OD); δ (ppm) 0.64–0.74 (1H, m), 0.79–1.82 (17H, m), 0.86 (3H, s), 1.10 (3H, m), 1.89–1.97 (1H, m), 2.04 (1H, d, J=12.4 Hz), 2.68 (1H, d, J=4.4 Hz), 2.79–2.84 (1H, m), 2.95 (1H, dd, J=6.4, 16.0 Hz)

Example 85

Methyl ent-17-acetylthio-15β-hydroxy-16α-atisane-19-oate

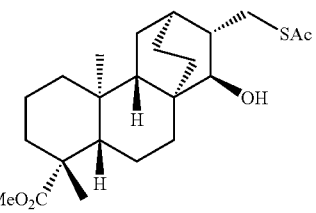

To a solution of methyl ent-15β-hydroxy-17-tosyloxy-16α-atisane-19-oate (13.2 mg, 0.026 mmol) obtained in Example 4 in dimethylformamide (1.5 mL) were added thioacetic acid (9.4 μl, 0.13 mmol) and sodium hydride (5.1 mg, 0.21 mmol), followed by stirring in nitrogen atmosphere at 80° C. for 4 hours. Then, water was added thereto under ice-cooling, and the mixture was extracted twice with diethyl ether. The resulting organic layer was washed with saturated brine, dried over magnesium sulfate and evaporated. The resulting residue was purified by silica gel column chromatography, to give methyl ent-17-acetylthio-15β-hydroxy-16α-atisane-19-oate (11.2 mg)
$^1$H NMR (CDCl$_3$); δ (ppm) 0.72–1.87 (18H, m), 0.79 (3H, s), 1.17 (3H, m), 1.93–2.00 (1H, m), 2.15 (1H, d, J=13.2 Hz), 2.35 (3H, s), 2.85–2.90 (2H, m), 3.04 (1H, dd, J=8.0, 13.2 Hz), 3.64 (3H, s)

Example 86

Di{2-[(1S,4S,5R,9S,10S,12S,13S,14R)-14-hydroxy-5-(methoxycarbonyl)-5,9-dimethyltetracyclo[10.2.2.0$^{1,10}$.0$^{4,9}$]hexadecy-13-yl]}disulfide

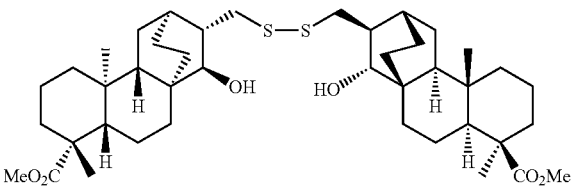

To a solution of methyl ent-17-acetylthio-15β-hydroxy-16α-atisane-19-oate (5.6 mg, 0.014 mmol) obtained in Example 85 in methanol (1.8 mL) was added a solution of sodium methoxide (10.8 mg, 0.2 mmol) in methanol (0.2 mL) at 0° C. in nitrogen atmosphere, followed by stirring for 2 hours and 30 minutes at 0° C. in nitrogen atmosphere. Then, saturated aqueous ammonium chloride was added thereto under ice-cooling and the mixture was extracted twice with diethyl ether. The resulting organic layer was washed with saturated brine, dried over magnesium sulfate and evaporated, to give di{2-[(1S,4S,5R,9S,10S,12S,13S,14R)-14-hydroxy-5-(methoxycarbonyl)-5,9-dimethyltetracyclo[10.2.2.0$^{1,10}$.0$^{4,9}$]hexadecy-13-yl]}disulfide (8.13 mg).

FAB-MS:m/z=753 (M+Na)$^+$ $^1$H NMR (CDCl$_3$); δ (ppm) 0.70–0.75 (2H, m), 0.86–1.83 (34H, m), 0.80 (6H, s), 1.18 (6H, m), 1.92–1.99 (2H, m), 2.16 (2H, d, J=12.8 Hz), 2.71 (2H, dd, J=7.2, 13.2 Hz), 2.85 (2H, dd, J=8.0, 13.2 Hz), 2.97 (2H, d, J=4 Hz), 3.65 (6H, s)

Example 87 ent-15β-Hydroxy-17-methyldisulfanyl-16α-atisane-19-oic acid

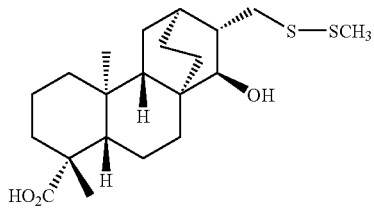

From di{2-[(1S,4S,5R,9S,10S,12S,13S,14R)-14-hydroxy-5-(methoxycarbonyl)-5,9-dimethyltetracyclo [10.2.2.0$^{1,10}$.0$^{4,9}$]hexadecy-13-yl]}disulfide (7.7 mg, 0.011 mmol) obtained in Example 86, ent-15β-hydroxy-17-methyldisulfanil-16α-atisane-19-oic acid (1.98 mg) was obtained in the same manner as described in Example 5.

ESI-MS:m/z=397 (M−H)$^-$ $^1$H NMR (CDCl$_3$); δ (PPM) 0.70–0.78 (11H, m), 0.87–1.90 (17H, m), 0.92 (3H, s), 1.25 (3H, m), 1.96–2.03 (1H, m), 2.12–2.18 (1H, m), 2.44 (3H, s), 2.75–2.79 (2H, m), 2.95 (1H, d, J=4 Hz)

Example 88 ent-15β-Hydroxy-17-phenylthio-16α-atisane-19-oic acid

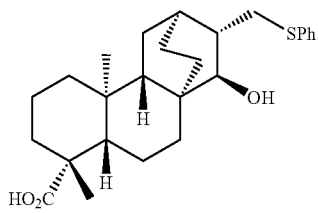

To a solution of methyl ent-15β-hydroxy-17-tosyloxy-16α-atisane-19-oate (14.1 mg, 0.028 mmol) obtained by Example 4 in hexamethylphosphoramide (1.5 mL) was added thiophenol (28.8 μl, 0.28 mmol) under stirring at room temperature, followed by stirring for 43 hours at 80° C. in nitrogen atmosphere. Then, the reaction was recovered to room temperature, saturated aqueous ammonium chloride was added, and extracted twice with diethyl ether. The resulting organic layer was washed with saturated brine, dried over magnesium sulfate and evaporated. The resulting residue was purified by silica gel column chromatography, to give ent-15β-hydroxy-17-phenylthio-16α-atisane-19-oic acid (11.4 mg, white crystals).

ESI-MS:m/z=427 (M−H)$^-$ $^1$H NMR (CDCl$_3$); δ (ppm) 0.72–0.81 (1H, m), 0.88–1.89 (17H, m), 0.91 (3H, s), 1.24 (3H, m), 1.96–2.04 (1H, m), 2.14 (1H, d, J=12.8 Hz), 2.96–2.98 (2H, m), 3.02 (1H, d, J=4 Hz), 7.16–7.20 (1H, m), 7.27–7.31 (2H, m), 7.35–7.38 (2H, m)

Example 89 ent-15β-Hydroxy-17-phenylsulfinyl-16α-atisane-19-oic acid

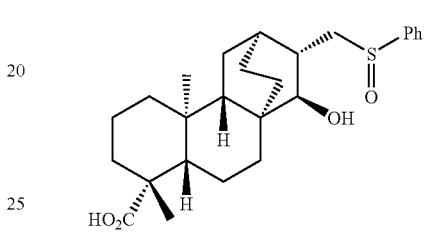

From ent-15β-hydroxy-17-phenylthio-16α-atisane-19-oic acid (5 mg, 0.0117 mmol) obtained in Example 88, ent-15β-hydrsoxy-17-phenylsulfinyl-16α-atisane-19-oic acid (7.2 mg) was obtained in the same manner as described in Example 6.

ESI-MS:m/z=443 (M−H)$^-$ $^1$H NMR (CD$_3$OD); δ (ppm) 0.78–0.86 (1H, m), 0.98–1.90 (17H, m), 0.94 (3H, s), 1.18 (3H, m), 1.98–2.04 (1H, m), 2.12 (1H, d, J=12.8 Hz), 2.87–3.00 (2H, m), 3.07–3.12 (1H, dd, J=6.6, 14.0 Hz), 7.51–7.61 (2H, m), 7.70–7.76 (1H, m), 7.89–7.91 (2H, m)

Example 90 ent-17-Dimethylamino-15β-hydroxy-16α-atisane-19-oic acid

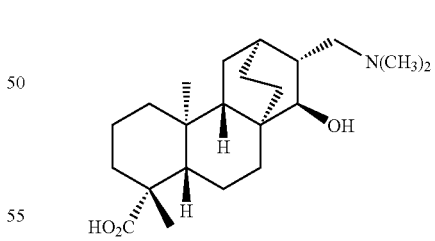

From ent-15β-hydroxy-17-tosyloxy-16α-atisane-19-oic acid obtained in Example 77, ent-17-dimethylamino-15β-hydroxy-16α-atisane-19-oic acid (3.1 mg) was obtained in the same manner as described in Example 79.

ESI-MS:m/z=364 (M+H)$^+$ $^1$H NMR (CD$_3$OD); δ (ppm) 0.69–0.77 (1H, m), 0.87–2.04 (18H, m), 0.97 (3H, s), 1.15 (3H, s), 2.13 (1H, d, J=13.6 Hz), 2.43 (6H, s), 2.53 (1H, dd, J=6.6, 12.4 Hz), 2.61 (1H, dd, J=8.8, 12.4 Hz), 2.74 (1H, d, J=4.0 Hz)

Example 91

Methyl ent-17-cyano-15β-hydroxy-16α-atisane-19-oate

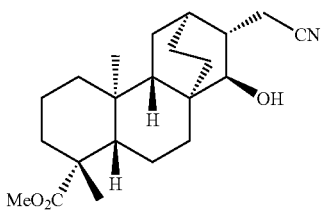

From methyl ent-15β-hydroxy-17-tosyloxy-16α-atisane-19-oate (124.7 mg, 0.247 mmol) obtained in Example 4, methyl ent-17-cyano-15β-hydroxy-16α-atisane-19-oate (89.7 mg, white crystals) was obtained in the same manner as described in Example 78.

$^1$H NMR (CDCl$_3$); δ (ppm) 0.70–1.86 (18H, m), 0.80 (3H, s), 1.18 (3H, s), 1.99–2.05 (1H, m), 2.17 (1H, d, J=13.2 Hz), 2.34 (1H, dd, J=8.8, 16.0 Hz), 2.52 (1H, dd, J=7.4, 16.0 Hz), 2.89 (1H, m), 3.65 (3H, s)

Example 92

Methyl ent-17-carboxyl-15β-hydroxy-16α-atisane-19-oate (S92-1)

Methyl ent-17-carbamoyl-15β-hydroxy-16α-atisane-19-oate (S92-2)

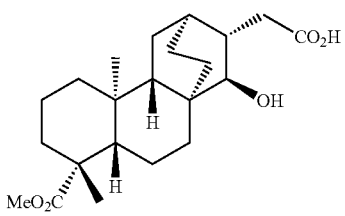
(S92-1)

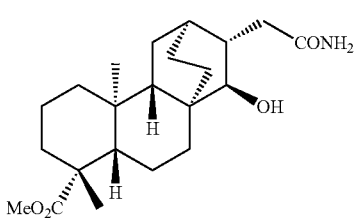
(S92-2)

To a solution of methyl ent-17-cyano-15β-hydroxy-16α-atisane-19-oate (36 mg, 0.1 mmol) obtained in Example 91 in ethanol (20 mL) was added potassium hydroxide (6 g, 0.107 mol), followed by stirring at 50° C. for 10 hours in nitrogen atmosphere. Then, the reaction mixture was neutralized with 5N hydrochloric acid under ice-cooling, and extracted twice with diethyl ether. The resulting organic layer was then washed with saturated brine, dried over magnesium sulfate and evaporated. The resulting residue was purified by silica gel column chromatography, to give methyl ent-17-carbamoyl-15β-hydroxy-16α-atisane-19-oate (10.1 mg, white crystals) and methyl ent-17-carboxyl-15β-hydroxy-16α-atisane-19-oate (22.2 mg, white crystals).

(S92-1) ESI-MS:m/z=377 (M−H)$^-$ $^1$H NMR (CDCl$_3$); δ (ppm) 0.71–1.85 (18H, m), 0.79 (3H, s), 1.18 (3H, s), 1.95–2.02 (1H, m), 2.15 (1H, d, J=12.8 Hz), 2.41–2.56 (2H, m), 2.93 (1H, d, J=4 Hz), 3.65 (3H, s)

(S92-2) ESI-MS:m/z=400 (M+Na)$^+$ $^1$H NMR (CDCl$_3$); δ (ppm) 0.71–1.87 (18H, m), 0.79 (3H, s), 1.18 (3H, m), 1.96–2.02 (1H, m), 2.15 (1H, d, J=12.0 Hz), 2.31–2.46 (2H, m), 2.94 (1H, d, J=4 Hz), 3.64 (3H, m), 5.49 (1H, bs), 5.84 (1H, bs)

Example 93 ent-17-Carboxyl-15β-hydroxy-16α-atisane-19-oic acid

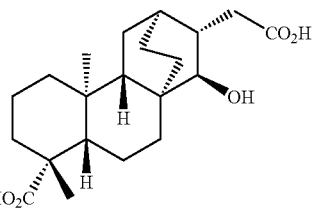

From methyl ent-17-carboxyl-15β-hydroxy-16α-atisane-19-oate (22.2 mg, 0.059 mmol) obtained in Example 92, ent-17-carboxyl-15β-hydroxy-16α-atisane-19-oic acid (16.0 mg, white crystals) was obtained in the same manner as described in Example 5.

ESI-MS:m/z=363 (M−H)$^-$ $^1$H NMR (CD$_3$OD); δ (ppm) 0.71–0.79 (1H, m), 0.87–2.01 (18H, m), 0.93 (3H, s), 1.18 (3H, s), 2.11 (1H, d, J=13.2 Hz), 2.30 (1H, dd, J=9.2, 15.0 Hz), 2.49 (1H, dd, J=6.6, 15.0 Hz), 2.78 (1H, d, J=4.0 Hz)

Example 94 ent-15β-Hydroxy-17-methoxycarbonyl-16α-atisane-19-oic acid

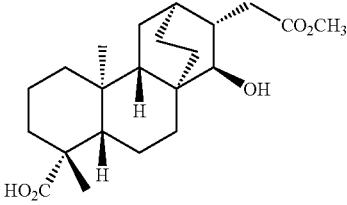

To a solution of ent-17-carboxyl-15β-hydroxy-16α-atisane-19-oic acid (3.0 mg, 0.0082 mmol) obtained in Example 93 in tetrahydrofuran (1 mL) were added ethyl chloroformate (2.0 μl, 0.021 mmol) and triethylamine (7.0 μl, 0.05 mmol) under stirring on ice in nitrogen atmosphere, followed by further stirring for 50 minutes under stirring on ice in nitrogen atmosphere. Then, methanol (0.4 mL) was introduced and stirred for 4 hours at room temperature. Then, 1N hydrochloric acid was added, and the mixture was extracted twice with ethyl acetate. The resulting organic layer was dried over magnesium sulfate and evaporated. The resulting residue was purified by silica gel column chromatography, to give ent-15β-hydroxy-17-methoxycarbonyl-16α-atisane-19-oic acid (0.82 mg).

ESI-MS:m/z=377 (M−H)⁻

¹H NMR (CDCl₃); δ (ppm) 0.71–2.21 (20H, m), 0.92 (3H, s), 1.25 (3H, s), 2.37–2.52 (2H, m), 2.88–2.91 (1H, m), 3.72 (3H, s)

Example 95 ent-17-Carbamoyl-15β-hydroxy-16α-atisane-19-oic acid

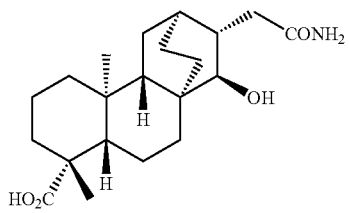

To a solution of ent-17-carboxyl-15β-hydroxy-16α-atisane-19-oic acid (3.0 mg, 0.0082 mmol) obtained in Example 93 in tetrahydrofuran (1 mL) were added ethyl chloroformate (2.0 μl, 0.021 mmol) and triethylamine (7.0 μl, 0.05 mmol) under stirring on ice in nitrogen atmosphere, followed by stirring for 25 minutes under stirring on ice in nitrogen atmosphere. Then, 28% aqueous ammonia (0.5 mL) was added, followed by stirring for another 4 hours. Thereafter, 1N hydrochloric acid was added, and extracted twice with a 1:1 mixture of ethyl acetate and tetrahydrofuran. The resulting organic layer was washed once with saturated brine, dried over magnesium sulfate and evaporated. The resulting residue was purified by silica gel column chromatography, to give ent-17-carbamoyl-15β-hydroxy-16α-atisane-19-oic acid (2.34 mg).

ESI-MS:m/z=362 (M−H)⁻

¹H NMR (CD₃OD); δ (ppm) 0.73–0.81 (1H, m), 0.89–1.90 (17H, m), 0.94 (3H, s), 1.19 (3H, s), 1.95–2.02 (1H, m), 2.12 (1H, d, J=13.2 Hz), 2.23 (1H, dd, J=8.4, 14.6 Hz), 2.41 (1H, dd, J=7.6, 14.6 Hz), 2.80 (1H, d, J=4.4 Hz)

Example 96 ent-17-Dimethylcarbamoyl-15β-hydroxy-16α-atisane-19-oic acid

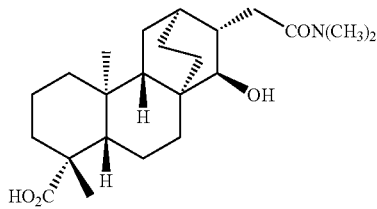

To a solution of ent-17-carboxyl-15β-hydroxy-16α-atisane-19-oic acid (3.0 mg, 0.0082 mmol) obtained in Example 93 in tetrahydrofuran (1 mL) were added ethyl chloroformate (2.0 μl, 0.021 mmol) and triethylamine (7.0 μl, 0.05 mmol) under stirring on ice in nitrogen atmosphere, followed by stirring for 25 minutes under ice-cooling in nitrogen atmosphere. Then, 2M dimethylamine solution in tetrahydrofuran (0.5 mL) was added, followed by stirring for another 4 hours. Then, 1N hydrochloric acid was added, and the reaction mixture was extracted twice with a 1:1 mixture of ethyl acetate and tetrahydrofuran. The resulting organic layer was washed once with saturated brine, dried over magnesium sulfate and evaporated. The resulting residue was purified by silica gel column chromatography, to give ent-17-dimethylcarbamoyl-15β-hydroxy-16α-atisane-19-oic acid (1.61 mg).

ESI-MS:m/z=390 (M−H)⁻

¹H NMR (CD₃OD); δ (ppm) 0.74–0.82 (1H, m), 0.88–2.03 (17H, m), 0.94 (3H, s), 1.18 (3H, s), 2.12 (1H, d, J=14.0), 2.46 (1H, dd, J=7.2, 15.2 Hz), 2.54 (1H, dd, J=8.2, 15.2 Hz), 2.82 (1H, d, J=4.4 Hz), 2.93 (3H, s), 3.08 (3H, s)

Example 97

Methyl ent-17-cyano-15β-(methoxymethyl)oxy-16α-atisane-19-oate

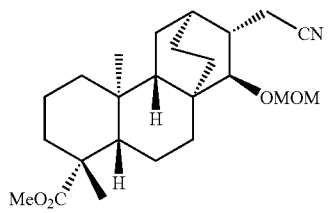

From methyl ent-17-cyano-15β-hydroxy-16α-atisane-19-oate (15.4 mg, 0.043 mmol) obtained in Example 91, methyl ent-17-cyano-15β-(methoxymethyl)oxy-16α-atisane-19-oate (16.8 mg, white crystals) was obtained in the same manner as described in Example 33.

¹H NMR (CDCl₃); δ (ppm) 0.68–0.76 (1H, m) 0.90–1.90 (17H, m), 0.79 (3H, s), 1.18 (3H, s), 1.97–2.04 (1H, m), 2.16 (1H, d, J=14.8 Hz), 2.26 (1H, dd, J=12.0, 16.8 Hz), 2.53 (1H, d, J=4.0 Hz), 2.76 (1H, dd, J=4.4, 16.8 Hz), 3.40 (3H, s), 3.65 (3H, s), 4.55 (1H, d, J=6.8 Hz), 4.71 (1H, d, J=6.8 Hz)

Example 98 ent-17-Cyano-15β-(methoxymethyl)oxy-16α-atisane-19-oic acid

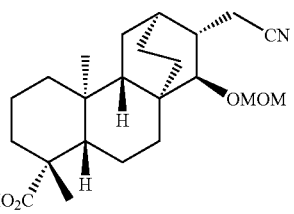

From methyl ent-17-cyano-15β-(methoxymethyl)oxy-16α-atisane-19-oate (7.0 mg, 0.0173 mmol) obtained in Example 97, ent-17-cyano-15β-(methoxymethyl)oxy-16α-atisane-19-oic acid (7 mg) was obtained in the manner as described in Example 5.

¹H NMR (CDCl₃); δ (ppm) 0.69–0.77 (1H, m), 0.91 (3H, s), 0.94–1.91 (17H, m), 1.25 (3H, s), 1.99–2.06 (1H, m), 2.16 (1H, d, J=13.6 Hz), 2.26 (1H, d, J=11.4, 17.0 Hz), 2.53 (1H, d, J=3.6 Hz), 2.77 (1H, dd, J=3.8, 17.0 Hz), 3.40 (3H, s), 4.56 (1H, d, J=7.0 Hz), 4.72 (1H, d, J=7.0 Hz)

Example 99 ent-17-Acetyl-15β-(methoxymethyl)oxy-16α-atisane-19-oic acid

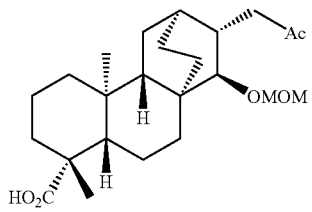

From ent-17-cyano-15β-(methoxymethyl)oxy-16α-atisane-19-oic acid (3.5 mg, 0.009 mmol) obtained in Example 98, ent-17-acetyl-15β-(methoxymethyl)oxy-16α-atisane-19-oic acid (1.35 mg) was obtained in the same manner as described in Example 60.

ESI-MS:m/z=405 (M−H)⁻

$^1$H NMR (CDCl$_3$); δ (ppm) 0.68–2.17 (20H, m), 0.89 (3H, s), 1.24 (3H, m), 2.14 (3H, s), 2.47 (1H, dd, J=11.2, 16.2 Hz), 2.61 (1H, d, J=3.6 Hz), 2.71 (1H, dd, J=3.6, 16.2 Hz), 3.37 (3H, s), 4.55 (1H, d, J=6.6 Hz), 4.72 (1H, d, J=6.6 Hz)

Example 100 ent-17-Acetyl-15β-hydroxy-16α-atisane-19-oic acid

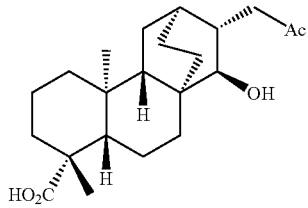

From ent-17-acetyl-15β-(methoxymethyl)oxy-16α-atisane-19-oic acid (1.35 mg, 0.00332 mmol) obtained in Example 99, ent-17-acetyl-15β-hydroxy-16α-atisane-19-oic acid (1.17 mg) was obtained in the same manner as described in Example 36.

ESI-MS:m/z=361 (M−H)⁻

$^1$H NMR (CD$_3$OD); δ (ppm) 0.70–0.78 (1H, m), 0.88–2.01 (18H, m), 0.94 (3H, s), 1.17 (3H, s), 2.12 (1H, d, J=13.2 Hz), 2.17 (3H, s), 2.56–2.59 (2H, m), 2.74 (1H, d, J=4.0 Hz)

Example 101

Methyl ent-17-fluoro-15β-hydroxy-16α-atisane-19-oate

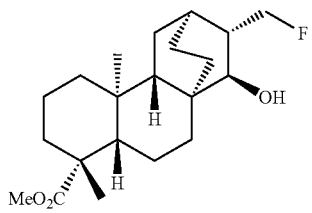

Methyl ent-15β-hydroxy-17-tosyloxy-16α-atisane-19-oate (7.52 mg, 0.0149 mmol) obtained in Example 4 was dissolved in 1M tetrabutyl ammonium fluoride in tetrahydrofuran (1 mL), followed by stirring for 17 hours at 50° C. Then, water was added, and extracted twice with diethyl ether. The resulting organic layer was washed once with saturated brine, dried over magnesium sulfate and evaporated. The resulting residue was purified by silica gel column chromatography, to give methyl ent-17-fluoro-15β-hydroxy-16α-atisane-19-oate (2.0 mg).

$^1$H NMR (CDCl$_3$); δ (ppm) 0.69–0.78 (1H, m), 0.80 (3H, s), 0.85–1.88 (17H, m), 1.18 (3H, s), 1.95–2.02 (1H, m), 2.14–2.19 (1H, m), 2.95 (1H, d, J=3.6 Hz), 3.65 (3H, s), 4.32–4.55 (2H, m)

Example 102 ent-17-Fluoro-15β-hydroxy-16α-atisane-19-oic acid

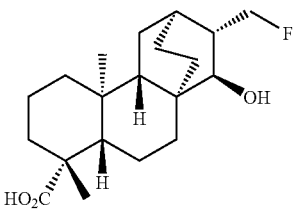

From methyl ent-17-fluoro-15β-hydroxy-16α-atisane-19-oate (2.0 mg, 0.0057 mmol) obtained by Example 101, ent-17-fluoro-15β-hydroxy-16α-atisane-19-oic acid (1.81 mg) was obtained in the same manner as described in Example 5.

ESI-MS:m/z=337 (M−H)⁻

$^1$H NMR (CD$_3$OD); δ (ppm) 0.68–0.76 (1H, m), 0.88–1.91 (17H, m), 0.94 (3H, m), 1.19 (3H, s), 1.94–2.02 (1H, m), 2.12 (1H, d, J=13.2 Hz), 2.75 (1H, d, J=4.4 Hz), 4.26–4.52 (2H, m)

Example 103

Methyl ent-15β-hydroxy-17-hydroxymethyl-16α-atisane-19-oate

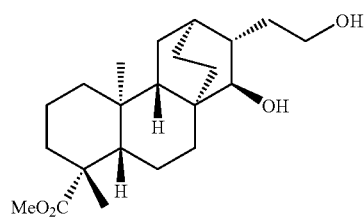

To a solution of methyl ent-17-carboxyl-15β-hydroxy-16α-atisane-19-oate (29.3 mg, 0.0774 mmol) obtained in Example 92 in tetrahydrofuran (5 mL) was added 1.0M boran tetrahydrofuran complex in tetrahydrofuran (0.387 mL, 0.387 mmol) under stirring on ice in nitrogen atmosphere, followed by stirring for 2 hours and 20 minutes at room temperature. Then, water was added under ice-cooling, followed by stirring for another 30 minutes. Then, 2N hydrochloric acid was added to make the reaction mixture acidic, followed by extracting twice with ethyl acetate. The resulting organic layer was washed with saturated brine, dried over magnesium sulfate and evaporated, to give methyl ent-15β-hydroxy-17-hydroxy-methyl-16α-atisane-19-oate (29.26 mg, white crystals).

¹H NMR (CD₃OD); δ (ppm) 0.71–1.98 (21H, m), 0.82 (3H, s), 1.17 (3H, s), 2.13 (1H, d, J=13.2 Hz), 2.76 (1H, d, J=4.0 Hz), 3.62–3.66 (5H, m)

Example 104

Methyl ent-15β-hydroxy-17-tosyloxymethyl-16α-atisane-19-oate

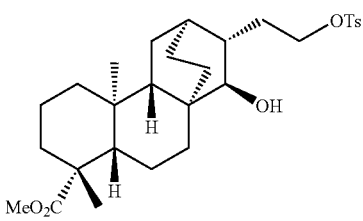

From methyl ent-15β-hydroxy-17-hydroxy-methyl-16α-atisane-19-oate (35.2 mg, 0.0965 mmol) obtained in Example 103, methyl ent-15β-hydroxy-17-tosyloxymethyl-16α-atisane-19-oate (20.02 mg, white crystals) was obtained in the same manner as described in Example 4.

¹H NMR (CDCl₃); δ (ppm) 0.63–1.82(20H, m), 0.77(3H, s), 1.17(3H, s), 1.90–1.96(1H, m), 2.16(1H, d, J=13.2 Hz), 2.45(3H, s), 2.77–2.79(1H, m), 3.64(3H, s), 4.10–4.22(2H, m), 7.35(2H, d, J=8.6 Hz), 7.80(2H, d, J=8.6 Hz)

Example 105 ent-15β-Hydroxy-17-(methylsulfinyl)methyl-16α-atisane-19-oic acid (S105-1)

ent-17-(Methylsulfinyl)methyl-15-oxo-16α-atisane-19-oic acid (S105-2)

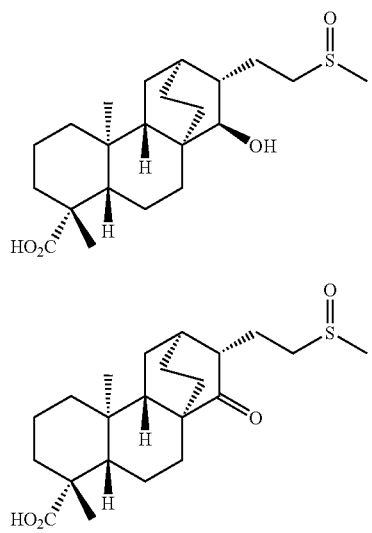

From methyl ent-15β-hydroxy-17-tosyloxymethyl-16α-atisane-19-oate (16.64 mg, 0.0321 mmol) obtained in Example 104, ent-15β-hydroxy-17-(methylsulfinyl)methyl-16α-atisane-19-oic acid (4.3 mg) was obtained in the same manner as described in Example 5 and by additional oxidation of sulfide under such a condition. Furthermore, oxidation of alcohol occurred, to give ent-17-(methylsulfinyl)methyl-15-oxo-16α-atisane-19-oic acid (4.2 mg).

(S105-1) ESI-MS:m/z=395 (M–H)⁻

¹H NMR (CD₃OD); δ (ppm) 0.74–0.82 (1H, m), 0.89–2.01 (20H, m), 0.94 (3H, m), 1.19 (3H, s), 2.12 (1H, d, J=13.2 Hz), 2.640 and 2.644 (3H, s×2), 2.78 (1H, d, J=4.0 Hz), 2.81–2.92 (2H, m)

(S105-2) ESI-MS:m/z=393 (M–H)⁻

¹H NMR (CD₃OD); δ (ppm) 0.88–0.95 (1H, m), 0.98–2.28 (21H, m), 1.04 (3H, s), 1.20 (3H, s), 2.648 and 2.649 (3H, s×2), 2.84–3.07 (2H, m)

Example 106

Methyl ent-15α-hydroxy-17-tosyloxy-16α-atisane-19-oate

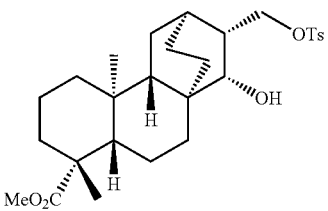

From methyl ent-15α,17-dihydroxy-16α-atisane-19-oate (200 mg, 0.57 mmol) obtained in Example 2, methyl ent-15α-hydroxy-17-tosyloxy-16α-atisane-19-oate (220.31 mg, white crystals) was obtained in the same manner as described in Example 4.

¹H NMR (CDCl₃) δ (ppm) 0.76–1.83 (18H, m), 0.79 (3H, s), 1.17 (3H, s), 2.15–2.20 (2H, m), 2.45 (3H, s), 3.39–3.42 (1H, m), 3.63 (3H, s), 4.04 (1H, dd, J=8.4, 9.8 Hz), 4.39 (1H, dd, J=7.0, 9.8 Hz), 7.34 (2H, d, J=8.2 Hz), 7.80 (2H, d, J=8.2 Hz)

Example 107 ent-15α-Hydroxy-17-methylthio-16α-atisane-19-oic acid

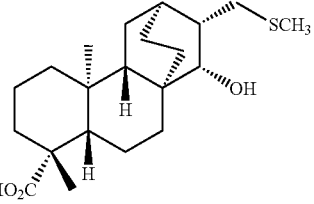

From methyl ent-15α-hydroxy-17-tosyloxy-16α-atisane-19-oate (220.3 mg, 0.437 mmol) obtained in Example 106, ent-15α-hydroxy-17-methylthio-16α-atisane-19-oic acid (133.9 mg, white crystals) was obtained in the same manner as described in Example 5.

ESI-MS:m/z=365 (M–H)⁻

¹H NMR (CDCl₃); δ (ppm) 0.84–2.20 (20H, m ), 0.94 (3H, s), 1.25 (3H, s), 2.15 (3H, s), 2.51 (1H, dd, J=5.4, 11.8 Hz), 2.89 (1H, dd, J=10.8, 11.8 Hz), 3.45 (1H, d, J=8.4 Hz)

Example 108 ent-15α-Hydroxy-17-methylsulfinyl-16α-atisane-19-oic acid

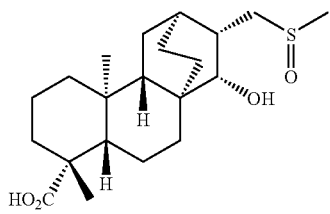

From ent-15α-hydroxy-17-methylthio-16α-atisane-19-oic acid (10.3 mg, 0.028 mmol) obtained in Example 107, ent-15α-hydroxy-17-methylsulfinyl-16α-atisane-19-oic acid was obtained in the same manner as described in Example 6. Furthermore, by means of silica gel column chromatography, two isomers are separated based on the configuration of sulfoxides, to give isomer 1 (5.86 mg) and isomer 2 (5.28 mg, white crystals).

(Isomer1)
ESI-MS:m/z=381 (M−H)+
$^1$H NMR (CD$_3$OD); δ (ppm) 0.89–1.95 (18H, m), 0.97 (3H, s), 1.19 (3H, s), 2.13 (1H, d, J=13.2 Hz), 2.29–2.35 (1H, m), 2.66 (3H, s), 2.78 (1H, dd, J=7.6, 13.2 Hz), 3.25–3.30 (1H, m), 3.35 (1H, d, J=8.8 Hz)

(Isomer2)
ESI-MS:m/z=381 (M−H)+
$^1$H NMR (CD$_3$OD); δ (ppm) 0.89–1.95 (18H, m), 0.97 (3H, s), 1.19 (3H, s), 2.13 (1H, d, J=14.0 Hz), 2.39–2.45 (1H, m), 2.54 (1H, dd, J=4.2, 13.2 Hz), 2.65 (3H, s), 3.36–3.42 (2H, m)

Example 109 ent-15α-Mesyloxy-17-methylthio-16α-atisane-19-oic acid

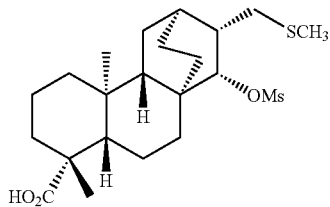

To a solution of ent-15α-hydroxy-17-methylthio-16α-atisane-19-oic acid (33.0 mg, 0.09 mmol) obtained in Example 107 in pyridine (3.0 mL) were added dimethylaminopyridine (1.1 mg, 0.009 mmol) and mesyl chloride (61.8 μl, 0.81 mmol) under stirring on ice. After stirring at room temperature for 69 hours, 1N hydrochloric acid was added under ice-cooling and extracted twice with ethyl acetate. The resulting organic layer was washed with 1N hydrochloric acid, dried over magnesium sulfate and evaporated. The resulting residue was purified by silica gel column chromatography, to give ent-15α-mesyloxy-17-methylthio-16α-atisane-19-oic acid (18.2 mg, white crystals).

$^1$H NMR (CD$_3$OD); δ (ppm) 0.90–2.23 (20H, m), 0.98 (3H, s), 1.19 (3H, s), 2.06 (3H, s), 2.58 (1H, dd, J=12.4, 12.8 Hz), 2.87 (1H, dd, J=4.4, 12.8 Hz), 3.10 (3H, s), 4.49 (1H, d, J=8.8 Hz)

Example 110 ent-15β-Azido-17-methylthio-16α-atisane-19-oic acid

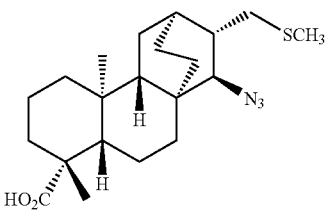

From ent-15α-mesyloxy-17-methylthio-16α-atisane-19-oic acid (9.3 mg, 0.021 mmol) obtained in Example 109, ent-15β-azido-17-methylthio-16α-atisane-19-oic acid (3.75 mg) was obtained in the same manner as described in Example 80.
ESI-MS:m/z=390 (M−H)+
$^1$H NMR (CDCl$_3$); δ (ppm) 0.79–2.18 (20H, m), 0.89 (3H, s), 1.26 (3H, s), 2.14 (3H, s), 2.50 (1H, dd, J=9.0, 13.2 Hz), 2.58 (1H, dd, J=7.2, 13.2 Hz), 2.80 (1H, d, J=4.0 Hz)

Example 111

Methyl ent-15β-(methoxymethyl)oxy-16-atisene-19-oate

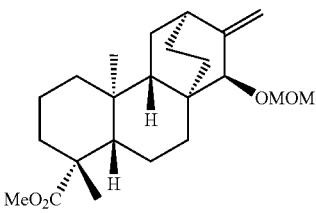

From methyl ent-15β-hydroxy-16-atisene-19-oate (91.9 mg, 0.276 mmol) obtained in Example 1, methyl ent-15β-(methoxymethyl)oxy-16-atisene-19-oate (101.1 mg, white crystals) was obtained in the same manner as described in Example 33.
$^1$H NMR (CDCl$_3$); δ (ppm) 0.83–2.03 (17H, m), 0.80 (3H, s), 1.19 (3H, s), 2.14–2.18 (1H, m), 2.29–2.32 (1H, m), 3.44 (3H, s), 3.53–3.54 (1H, m), 3.65 (3H, s), 4.70 (1H, d, J=6.8 Hz), 4.86 (1H, d, J=6.8 Hz), 4.98–4.99 (1H, m), 5.04–5.05 (1H, m)

Example 112

Methyl (1R,4S,5R,9S,10S,12S,14S)-14-(methoxymethoxy)-5,9-dimethyl-13-oxotetracyclo[10.2.2.0$^{1,10}$.0$^{4,9}$]hexadecane-5-carboxylate

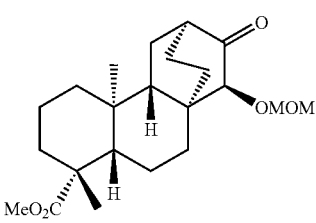

Methyl ent-15β-(methoxymethyl)oxy-16-atisene-19-oate (35.0 mg, 0.093 mmol) obtained in Example 111 was dissolved in a 1:1 tetrahydrofuran:water mixed solvent (6 mL) and a 2.5% solution of osmium tetraoxide in t-butanol (0.1 mL, 0.008 mmol) was added thereto, followed by stirring at room temperature for 30 minutes. Then, sodium periodate (69.9 mg, 0.327 mmol) was added and stirred at room temperature for 25 hours. Then saturated aqueous sodium thiosulfate was added, stirred for 30 minutes, and then the reaction mixture was extracted twice with diethyl ether. The resulting organic layer was washed with 1N hydrochloric acid, dried over magnesium sulfate and evaporated. The resulting residue was purified by silica gel column chromatography, to give methyl (1R,4S,5R,9S,10S,12S,14S)-14-(methoxymethoxy)-5,9-dimethyl-13-oxotetracyclo[10.2.2.0$^{1,10}$.0$^{4,9}$]hexadecane-5-carboxylate (19.6 mg, white crystals).

ESI-MS:m/z=402 (M+Na)$^+$ $^1$H NMR (CDCl$_3$); δ (ppm) 0.85–2.34 (19H, m), 0.86 (3H, s), 1.20 (3H, s), 3.26 (1H, s), 3.48 (3H, s), 3.67 (3H, s), 4.72 (1H, d, J=6.4 Hz), 5.10 (1H, d, J=6.4 Hz)

Example 113

Methyl (1R,4S,5R,9S,10S,12S,13R,14S)-13-hydroxy-14-(methoxymethoxy)-5,9-dimethyltetracyclo[10.2.2.0$^{1,10}$.0$^{4,9}$]hexadecane-5-carboxylate

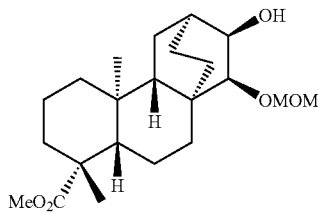

To a solution of methyl (1R,4S,5R,9S,10S,12S,14S)-14-(methoxymethoxy)-5,9-dimethyl-13-oxotetracyclo[10.2.2.0$^{1,10}$.0$^{4,9}$]hexadecane-5-carboxylate (13.0 mg, 0.0343 mmol) obtained in Example 112 in dichloromethane (1.5 mL) was added 1.5M diisobutyl aluminum hydride in toluene (34 μl, 0.0515 mmol) under stirring at −78° C., followed by stirring at −78° C. for 4 hours and 40 minutes. Under ice-cooling, water was added and the mixture was extracted twice with diethylether. The resulting organic layer was washed with saturated brine, dried over magnesium sulfate and evaporated. The resulting residue was purified by silica gel column chromatography, to give methyl (1R,4S,5R,9S,10S,12S,13R,14S)-13-hydroxy-14-(methoxymethoxy)-5,9-dimethyltetracyclo[10.2.2.0$^{1,10}$.0$^{4,9}$]hexadecane-5-carboxylate (7.5 mg).

$^1$H NMR (CDCl$_3$); δ (ppm) 0.77–1.88 (17H, m), 0.79 (3H, s), 1.18 (3H, s), 1.94–2.01 (1H, m), 2.16 (1H, d, J=14.0 Hz), 3.15 (11H, d, J=4.8 Hz), 3.19 (1H, d, J=8.4 Hz), 3.48 (3H, s), 3.65 (3H, s), 3.85–3.89 (1H, m), 4.64 (1H, d, J=6.4 Hz), 4.82 (1H, d, J=6.4 Hz)

Example 114

Methyl (1R,4S,5R,9S,10S,12S,13R,14S)-14-(methoxymethoxy)-5,9-dimethyl-13-[(methylsulfonyl)oxy]tetracyclo[10.2.2.0$^{1,10}$.0$^{4,9}$]hexadecane-5-carboxylate

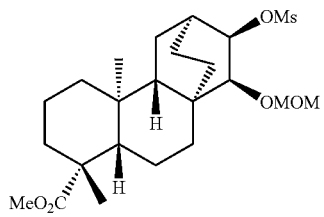

From methyl (1R,4S,5R,9S,10S,12S,13R,14S)-13-hydroxy-14-(methoxymethoxy)-5,9-dimethyltetracyclo[10.2.2.0$^{1,10}$.0$^{4,9}$]hexadecane-5-carboxylate (7.5 mg, 0.0196 mmol) obtained in Example 113, methyl (1R,4S,5R,9S,10S,12S,13R,14S)-14-(methoxymethoxy)-5,9-dimethyl-13-[(methylsulfonyl)oxy]tetracyclo[10.2.2.0$^{1,10}$.0$^{4,9}$]hexadecane-5-carboxylate (8.3 mg) was obtained in the same manner as described in Example 109.

$^1$H NMR (CDCl$_3$); δ (ppm) 0.77–2.10 (18H, m), 0.79 (3H, s), 1.18 (3H, s), 2.16 (1H, d, J=13.6 Hz), 3.05 (3H, s), 3.38 (1H, d, J=8.4 Hz), 3.45 (3H, s), 3.65 (3H, s), 4.67 (1H, d, J=6.6 Hz), 4.77 (1H, d, J=6.6 Hz), 4.90–4.93 (1H, m)

Example 115

(1R,4S,5R,9S,10S,12S,13S,14S)-14-(Methoxymethoxy)-5,9-dimethyl-13-(methylsulfinyl)tetracyclo[10.2.2.0$^{1,10}$.0$^{4,9}$]hexadecane-5-carboxylic acid

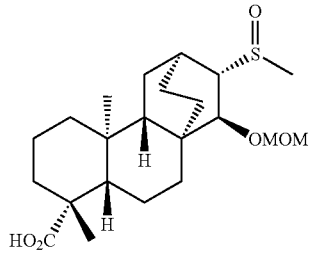

From methyl (1R,4S,5R,9S,10S,12S,13R,14S)-14-(methoxymethoxy)-5,9-dimethyl-13-[(methylsulfonyl)oxy]tetracyclo[10.2.2.0$^{1,10}$0.$^{4,9}$]hexadecane-5-carboxylate (8.3 mg, 0.018 mmol) obtained in Example 114, (1R,4S,5R,9S,10S,12S,13S,14S)-14-(methoxymethoxy)-5,9-dimethyl-13-(methylsulfinyl)tetracyclo[10.2.2.0$^{1,10}$.0$^{4,9}$]hexadecane-5-carboxylic acid (8.2 mg) was obtained in the same manner as described in Example 5 and by oxidation of sulfide occurring in such a condition.

ESI-MS:m/z=413 (M+H)$^+$ $^1$H NMR (CD$_3$OD); δ (ppm) 0.90–2.29 (19H, m), 0.94 and 0.96 (3H, S×2), 1.19 and 1.20 (3H, S×2), 2.70 and 2.82 (3H, S×2), 2.83–2.86 (1H, m), 2.99 (0.5H, d, J=2.4 Hz), 3.38 and 3.39 (3H, S×2), 3.55 (0.5H, d, J=0.2 Hz), 4.63 (0.5H, d, J=6.6 Hz), 4.67 (0.5H, d, J=7.2 Hz), 4.77 (0.5H, d, J=7.2 Hz), 4.92 (0.5H, d, J=6.6 Hz)

Example 116

(1R,4S,5R,9S,10S,12S,13S,14S)-14-Hydroxy-5,9-dimethyl-13-(methylsulfinyl)tetracyclo[10.2.2.0$^{1,10}$.0$^{4,9}$]hexadecane-5-carboxylic acid

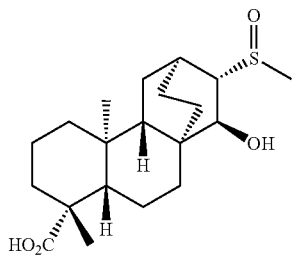

To a solution of (1R,4S,5R,9S,10S,12S,13S,14S)-14-(methoxymethoxy)-5,9-dimethyl-13-(methylsulfinyl)tetracyclo[10.2.2.0$^{1,10}$.0$^{4,9}$]hexadecane-5-carboxylic acid (4.1 mg, 0.0099 mmol) obtained in Example 115 in tetrahydrofuran (2 mL) was added trifluoroacetic acid (2 mL) under stirring on ice. After stirring at 50° C. for 29 hours, the reaction mixture was evaporated, to give (1R,4S,5R,9S,10S,12S,13S,14S)-14-hydroxy-5,9-dimethyl-13-(methylsulfinyl)tetracyclo[10.2.2.0$^{1,10}$.0$^{4,9}$]hexadecane-5-carboxylic acid. This product was further purified by silica gel column chromatography so as to separate two isomers based on the configuration of sulfoxide, to give isomer 1 (0.71 mg) and isomer 2 (1.01 mg).

(Isomer1)

ESI-MS:m/z=367 (M–H)$^+$ $^1$H NMR (CD$_3$OD); δ (ppm) 0.83–2.08 (18H, m), 0.94 (3H, m), 1.20 (3H, s), 2.14 (1H, d, J=13.2 Hz), 2.54–2.58 (1H, m), 2.65 (3H, s), 3.70 (1H, d, J=4.4 Hz)

(Isomer2)

ESI-MS:m/z=367 (M–H)$^+$ $^1$H NMR (CD$_3$OD); δ (ppm) 0.75–2.20 (19H, m), 0.96 (3H, s), 1.19 (3H, s), 2.64–2.73 (2H, m), 2.71 (3H, s),

Example 117 ent-15β-Azido-17-methylsulfinyl-16α-atisane-19-oic acid

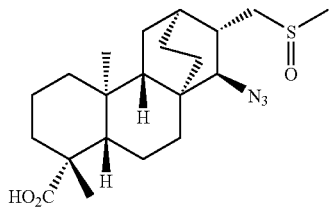

From ent-15β-azido-17-methylthio-16α-atisane-19-oic acid (3.8 mg, 0.0096 mmol) obtained in Example 110, ent-15β-azido-17-methylsulfinyl-16β-atisane-19-oic acid (3.84 mg) was obtained in the same manner as described in Example 6.

ESI-MS:m/z=406 (M–H)$^+$ $^1$H NMR (CD$_3$OD); δ (ppm) 0.86–2.15 (20H, m), 0.94 (3H, s), 1.21 (3H, s), 2.70 and 2.71 (3H, s×2), 2.79–3.03 (3H, m)

Example 118 ent-15β-{(t-Butoxycarbonyl)amino}-17-methylthio-16α-atisane-19-oic acid

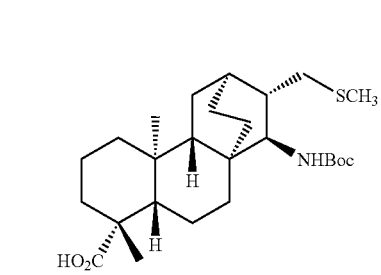

(118-1)

From ent-15β-azido-17-methylthio-16α-atisane-19-oic acid (7.3 mg, 0.019 mmol) obtained in Example 110, ent-15β-amino-17-methylthio-16α-atisane-19-oic acid (crude product) was obtained in the same manner as described in Example 21.

ESI-MS:m/z=366 (M+H)$^+$ (118-2)

From ent-15β-amino-17-methylthio-16α-atisane-19-oic acid, ent-15β-{(t-butoxycarbonyl)amino}-17-methylthio-16α-atisane-19-oic acid (1.1 mg) was obtained in the same manner as described in Example 30 (2).

ESI-MS:m/z=464 (M–H)$^+$ $^1$H NMR (CDCl$_3$); δ (ppm) 0.86–2.19 (20H, m), 0.96 (3H, s), 1.25 (3H, s), 1.47 (9H, s), 2.09 (3H, s), 2.55 (1H, t, J=10.4 Hz), 2.73 (1H, dd, J=5.2, 12.8 Hz), 2.88–2.95 (1H, m), 4.45 (1H, d, J=10.4 Hz)

Example 119 ent-15β-{(t-Butoxycarbonyl)amino}-17-methylsulfinyl-16α-atisane-19-oic acid

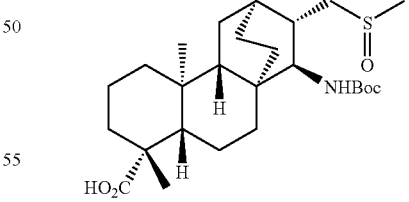

From ent-15β-{(t-butoxycarbonyl)amino}-17-methylthio-16α-atisane-19-oic acid (1.1 mg, 0.0024 mmol) obtained by Example 118, ent-15β-{(t-butoxycarbonyl)amino}-17-methylsulfinyl-16α-atisane-19-oic acid (1.6 mg) was obtained in the same manner as described in Example 6.

$^1$H NMR (CD$_3$OD); δ (ppm) 0.90–2.14 (20H, m), 0.93 and 0.94 (3H, s×2), 1.19 (3H, s), 1.46 (9H, s), 2.64 and 2.66 (3H, s×2), 2.76–3.01 (3H, m)

Example 120 ent-15β-Amino-17-methylsulfinyl-16α-atisane-19-oic acid-trifluoroacetic acid

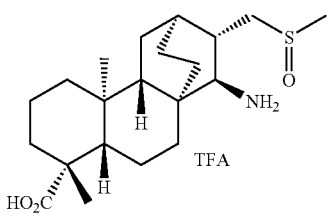

From ent-15β-{(t-butoxycarbonyl)amino}-17-methylsulfinyl-16α-atisane-19-oic acid (1.6 mg, 0.0033 mmol) obtained in Example 119, ent-15β-amino-17-methylsulfinyl-16α-atisane-19-oic acid-trifluoroacetic acid (2.31 mg) was obtained in the same manner as described in Example 32.

ESI-MS:m/z=382 (M+H)$^+$

Isolation of Serofendic Acids A and B (1) Serofendic acids A and B were prepared from 250 L of serum (FCS). First, each separating funnel was charged with 2 L of inactivated serum (heat-inactivated FCS), and then 2 L, an equivalent amount to the serum, of ethyl acetate was added, and thoroughly stirred. Then, the upper layer (ethyl acetate layer) was collected while taking care that the lower layer (aqueous layer) did not to get mixed into the upper layer. After adding to this lower layer 2 L of ethyl acetate and stirring, the ethyl acetate layer was collected. This series of operations was repeated a total of 125 times, and finally extracted with ethyl acetate (500 L) of twice the original amount of serum.

(2) From the ethyl acetate extract obtained in the above (1), ethyl acetate was evaporated using an evaporator on a water bath at 45° C. At this time, the ethyl acetate extract was divided into quarters, and each 125 L portions were evaporated. To each quarter of the evaporated ethyl acetate extract were added 2 L of n-hexane and 90% methanol water and poured into a separating funnel and stirred. Then, the lower layer (90% methanol aqueous layer) was collected. To the upper layer (n-hexane layer) was further added 90% methanol water (2 L) and stirred, and then 90% methanol aqueous layer was collected. This series of operations was repeated 4 times, and finally separated into two phases using 8 L of n-hexane and 16 L of 90% methanol water.

(3) From each quarter of the 90% methanol aqueous layer obtained in the above (2), 90% methanol water was evaporated by means of an evaporator on an water bath at 45° C. To the evaporated 90% methanol aqueous phase were added 2 L of ethyl acetate and 2 L of water, and poured into a separating funnel and stirred. Then, the upper layer (ethyl acetate layer) was collected. To the lower phase (aqueous layer) was further added ethyl acetate (2 L) and stirred, and then the ethyl acetate layer was collected. This series of operations was repeated 4 times to finally achieve diphase separation using 16 L of ethyl acetate and 8 L of water. (4) From the ethyl acetate layer obtained in the above (3), ethyl acetate was evaporated by means of an evaporator on a water bath at 45° C. In this manner, from 250 L of serum, a crude extract fraction containing Serofendic acids A and B were purified. (5) The crude extract fraction was fractionated using High-performance liquid chromatography (HPLC) in the following conditions:

(a) Column: YMC-pack ODS-AM (250 nm×20 mm i.d., YMC);

(b) Mobile phase: H$_2$O/CH$_3$CN/TFA (mobile phase A=990:10:1, mobile phase B=10:990:1); and (c) Gradient program (B conc. %): 0 min. (10%)→50 min. (80%)→60 min. (80%)→60.01 min. (10%)→70 min. (stop)

(6) Each eluted fraction sample thus obtained was subjected to LCMS to analyze contents of Serofendic acids A and B. In the LCMS analysis, the following conditions were employed.

(a) Column: Inertsil ODS-3 (150 mm×1.5 mm i.d., GL-Science);

(b) Mobile phase: H$_2$O/MeOH containing 2 mM ammonium acetate (mobile phase A=900:100, mobile phase B=10:990);

(c) Gradient program (B conc. %): 0 min. (60%)→10 min. (90%)→10.01 min. (60%)→15 min. (stop);

(d) Ionization method: ESI (+); and (e) Monitoring method: SIM mode (m/z 383)

(7) Fractions containing Serofendic acids A and B (retention time: about 12 to 25 min.) were taken together, and the mobile phase was evaporated by means of an evaporator. The obtained fraction was subjected to final purification by LCMS in the following conditions.

(a) Column: YMC-pack ODS-AM (250 nm×10 mm i.d., YMC);

(b) Mobile phase: H$_2$O/MeOH (moving phase A=900:100, moving phase B=100:900) containing 5 mM ammonium acetate;

(c) Gradient program (B conc. %): 0 min. (45%)→30 min. (60%)→35 min. (90%)→40 min. (90%)→40.01 min. (45%)→50 min. (stop);

(d) Ionization method: ESI (+); and (e) Monitoring method: SIM mode (m/z 383)

The obtained eluted fraction sample was dried by an evaporator (end of isolation process). Physicochemical data of the bioactive substances (the title compounds) obtained from that fraction sample are as follows.

serofendic acid A ESI-MS: m/z=383 (M+H)$^+$ serofendic acid B ESI-MS: m/z=383 (M+H)$^+$ Serofendic Acid A (Isomer (1), PR46)

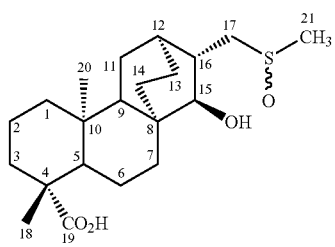

ESI-MS:m/z=383 (M+H)$^+$

Proton NMR data and carbon NMR data of Serofendic acid A (isomer 1, PR46) are shown in Table 1.

TABLE 1

| position | $\sigma_c$ | $\sigma_H$ |
|---|---|---|
| 1 | 41.2 | 1.66 (m), 1.00 (m) |
| 2 | 20.0 | 1.93 (m), 1.42 (m) |
| 3 | 39.3 | 2.17 (brd, 14.2), 1.07 (m) |
| 4 | 44.7 | |
| 5 | 57.8 | 1.07 (m) |
| 6 | 20.9 | 1.90 (m), 1.84 (m) |
| 7 | 34.3 | 1.74 (ddd, 13.2, 13.2, 4.5) 1.10 (ddd, 13.2, 2.9, 2.9) |
| 8 | 37.7 | |
| 9 | 42.8 | 1.62 (m) |
| 10 | 39.2 | |
| 11 | 30.0 | 1.64 (m), 1.45 (m) |
| 12 | 32.2 | 1.70 (m) |
| 13 | 22.2 | 1.68 (m), 1.42 (m) |
| 14 | 28.2 | 2.06 (ddd, 14.2, 11.7, 2.9), 0.87 (m) |
| 15 | 81.3 | 2.97 (d, 2.9) |
| 16 | 44.5 | 1.95 (m) |
| 17 | 60.9 | 2.99 (dd, 13.0, 9.3), 2.87 (dd, 13.0, 6.1) |
| 18 | 29.5 | 1.23 (s) |
| 19 | 181.7 | |
| 20 | 13.4 | 0.99 (s) |
| 21 | 38.8 | 2.72 (s) |

*Recorded in $CD_3OD$ at 30° C. Chemical shifts were referenced to internal peaks $\sigma_H$ 3.35 for $CD_2HOD$ and $\sigma_c$ 49.0 for $CD_3OD$. Serofendic acid B (isomer (2) PR47)*

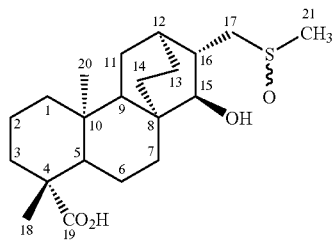

ESI-MS:m/z=383 (M+H)$^+$

Figure 2:
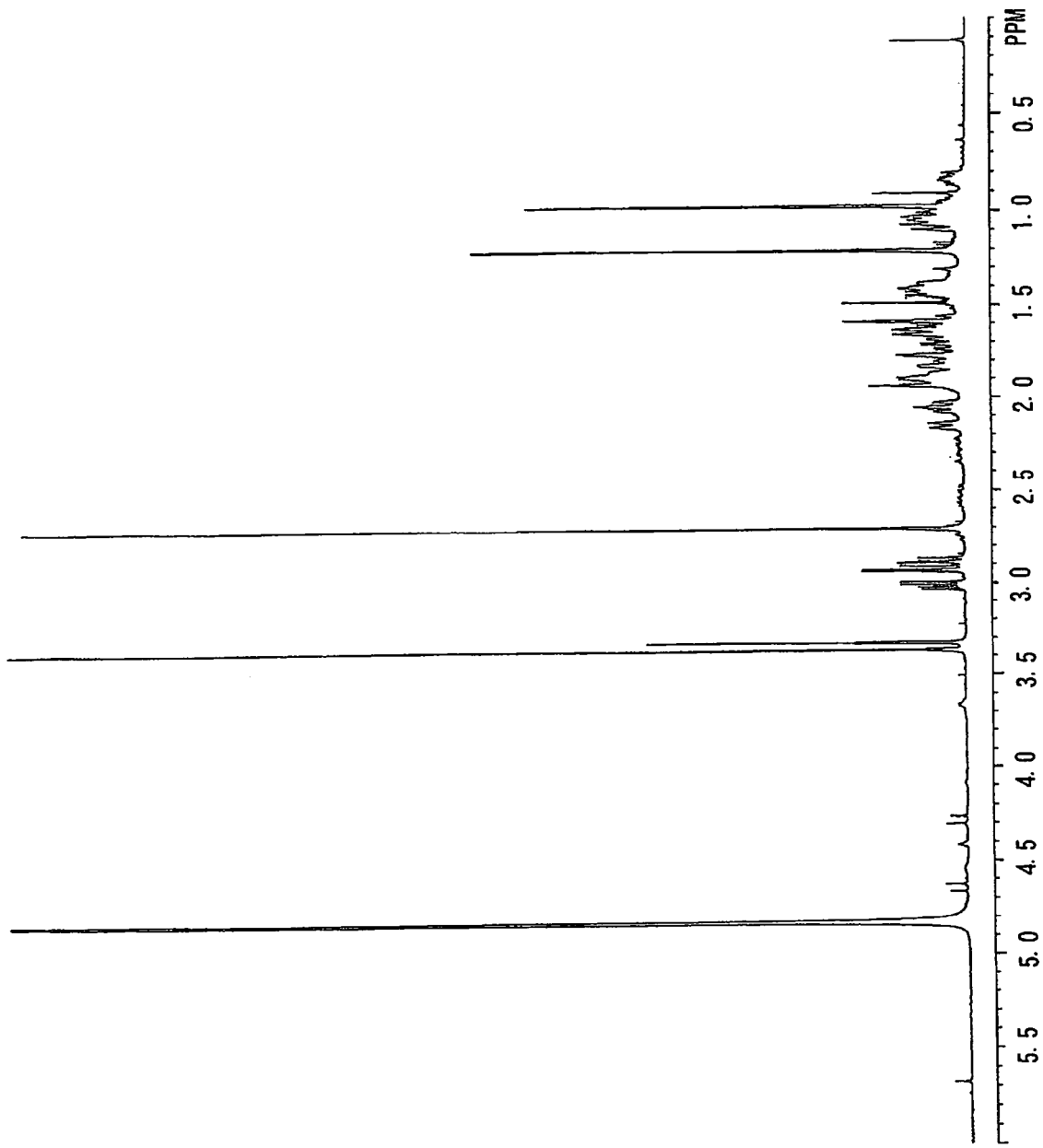
FIG. 2 is a view showing the proton NMR spectrum (500 MHz: δppm in $CD_3OD$) of the substance obtained in Example 6 (Serofendic acid B (isomer 2)).

Proton NMR data and carbon NMR data of Serofendic acid B (isomer 2, PR47)* are shown in Table 2, and proton NMR spectrum (measured in $CD_3OD$, 500 MHz: δ ppm in $CD_3OD$) is shown in FIG. 2.

TABLE 2

| position | $\sigma_c$ | $\sigma_H$ |
|---|---|---|
| 1 | 41.3 | 1.66 (m), 1.00 (m) |
| 2 | 20.1 | 1.96 (m), 1.42 (m) |
| 3 | 39.4 | 2.18 (brd, 13.2), 1.06 (m) |
| 4 | 44.8 | |
| 5 | 57.9 | 1.06 (m) |
| 6 | 21.0 | 1.90 (m), 1.83 (m) |
| 7 | 34.3 | 1.73 (ddd, 13.2, 13.2, 4.4) 1.10 (ddd, 13.2, 2.9, 2.9) |
| 8 | 37.7 | |
| 9 | 42.9 | 1.62 (m) |
| 10 | 39.2 | |
| 11 | 29.9 | 1.63 (m), 1.46 (m) |
| 12 | 30.8 | 1.79 (m) |
| 13 | 21.9 | 1.66 (m), 1.44 (m) |
| 14 | 28.4 | 2.08 (ddd, 14.0, 11.7, 3.0) 0.86 (ddd, 14.0, 12.2, 6.5) |
| 15 | 81.2 | 2.95 (d, 4.4) |
| 16 | 44.3 | 1.92 (m) |
| 17 | 59.8 | 3.04 (dd, 13.2, 6.8), 2.91 (dd, 13.2, 9.0) |
| 18 | 29.6 | 1.23 (s) |
| 19 | 181.0 | |
| 20 | 13.5 | 0.99 (s) |
| 21 | 38.3 | 2.73 (s) |

*Recorded in $CD_3OD$ at 30° C. Chemical shifts were referenced to internal peaks $\sigma_H$ 3.35 for $CD_2HOD$ and $\sigma_c$ 49.0 for $CD_3OD$.

"position" in the above Tables 1 and 2 refers to the nomenclatural position in the particular compound, and the footnote "Recorded in $CD_3OD$ at 30° C. Chemical shifts were referenced to internal peaks $\sigma_H$ 3.35 for $CD_2HOD$ and $\sigma_c$ 49.0 for $CD_3OD$ "means" measured in a solvent of $CD_3OD$ at 30° C. Chemical shifts were referenced to internal peaks $\sigma_H$ 3.35 ppm for $CD_2HOD$ and $\sigma_c$ 49.0 ppm for $CD_3OD$".

Test Example 1

Effect of Atisane Derivative on Glutamate-induced Neurotoxicity of Cultured Cerebral Cortex Cell Effects of the compounds according to the present invention on survival of cells were studied in the following manners.

(1) After dissolving the compound according to the present invention (test compound) in a small amount of methanol, 2.0 mL serum-free normal medium (Eagle's MEM medium raw powder 9.4 g; $NaHCO_3$ 2.0 g; L-glutamine 0.29 g; glucose 1.0 g; and HEPES 2.38 g are dissolved in purified water so that the final volume is 1000 mL) was added so as to make the concentration at 10 µM. After mixing well by vortex, the sample was used for the following bioassay.

(2) In Eagle liquid at 37° C., cultured cerebral cortex cells were incubated in the medium containing the test sample (1) for 1 hour, and glutamic acid was added to the medium. After incubating for another 1 hour, the culture was stained with 1.5% trypan blue solution for 10 minutes. After completion of the staining, cells were fixed in ice-cooled 10% neutral-buffered formalin solution, and rinsed with saline. In the trypan blue staining, living cells having an ability to reject trypan blue are not stained, whereas cells that are severely damaged lose the rejecting ability so that they are stained. Using this property, in the present test, the number of cells were counted while determining the cells not having stained by trypan blue as living cells and the cells not having stained as dead cells. The test was conducted using 5 cover slips for every drug treatment, and one group contained 5 cases. More than 200 cells were counted per one cover slip, and a percentage of number of living cells with respect to the total number of counted cells was calculated as survival.

Results

The compound of the present invention obtained in Example 1 significantly suppressed the neurotoxicity induced by 500 µM glutamic acid, at a concentration of 10 µM as shown in Table 3.

TABLE 3

| | Survival of cell | s.e.m |
|---|---|---|
| sham | 88.7928716 | 0.616460 |
| Glutamic acid 500 µM | 26.7155018 | 0.838002 |
| Glutamic acid 500 µM + Serofendic acid isomers (1), (2) (approx. 1:2) mixture 10 µM | 65.9232298 | 1.269272 |

In Table 3, "sham" means "cell survival in the case treated with neither glutamic acid nor Serofendic acid" and "s.e.m" is an abbreviation for "standard error of the mean" and means "standard error".

Test Example 2

Effect of Atisane Derivative on Nitrogen Monoxide (NO)-induced Neurotoxicity of Cultured Cerebral Cortex Cell (1) After dissolving the compound according to the present invention (test compound) in a small amount of methanol, 2.0 mL serum-free normal medium (Eagle's MEM medium raw powder 9.4 g; $NaHCO_3$ 2.0 g; S-nitrosocysteine 100–300 μM; glucose 1.0 g; and HEPES 2.38 g are dissolved in purified water so that the final volume is 1000 mL) was added to make the concentration at 10 μM. After mixing well by vortex, the sample was used for the following bioassay.

(2) In Eagle liquid at 37° C., cultured cerebral cortex cells were incubated in the medium containing S-nitrosocysteine for 1 hour. At this time, the test sample (1) was treated simultaneously with S-nitrosocysteine. After incubating for another 1 hour, the culture was stained with 1.5% trypan blue solution for 10 minutes. After completion of the staining, cells were fixed in ice-cooled 10% neutral-buffered formalin solution, rinsed with saline, and numbers of living cells and dead cells were counted. The test was conducted using 5 cover slips for every drug treatment, and one group contained 5 cases. More than 200 cells were counted per one cover slip, and a percentage of number of living cells with respect to the total number of counted cells was calculated as survival.

(3) Results

The compound of the present invention significantly suppressed the neurotoxicity induced by NO, at a concentration of 10 μM as shown in Table 4.

TABLE 4

|  | Survival of cell | s.e.m |
| --- | --- | --- |
| sham | 91.9230109 | 0.249936 |
| S-nitrosocysteine 100 μM | 17.3029439 | 0.745891 |
| S-nitrosocysteine 100 μM + Serofendic acid isomers (1), (2) (approx. 1:2) mixture 10 μM | 76.0222324 | 1.7224187 |

In Table 4, "sham" means "cell survival in the case treated with neither S-nitrosocysteine nor Serofendic acid" and "s.e.m" is an abbreviation for "standard error of the mean" and means "standard error".

What is claimed is:

1. A compound represented by the following formula, or a salt thereof or a hydrate thereof:

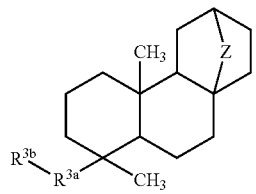

(I)

wherein Z is a group represented by the formula:

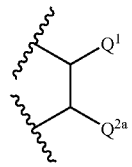

wherein $Q^1$ is

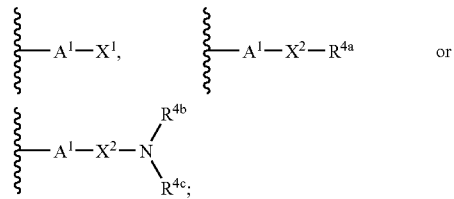

wherein $A^1$ represents an optionally substituted $C_{1-6}$ alkylene group or a single bond;

$X^1$ represents a halogen atom or a cyano group;

$X^2$ represents the formula $—S(O)_m—$, an oxygen atom, a carbonyl group or a single bond, wherein m of $—S(O)_m—$ is an integer of 0, 1 or 2;

$R^{4a}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{1-6}$ alkoxy group or a hydroxyl group; and $R^{4b}$ and $R^{4c}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group;

$Q^{2a}$ represents a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, a hydroxyl group or a group represented by the formula $—NR^{6a}R^{6b}$, wherein $R^{6a}$ and $R^{6b}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{2-7}$ acyl group or an optionally substituted $C_{1-6}$ alkylsulfonyl group:

$R^{3a}$ represents a carbonyl group, a methylene group or a single bond; and $R^{3b}$ represents a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, a hydroxyl group, a cyano group or a group represented by the formula $—NR^{5a}R^{5b}$, wherein $R^{5a}$ and $R^{5b}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group, provided that the following cases (1) to (3) are excluded:

(1) Z represents a 1,2-dicarboxyethane-1,2-yl group or a 1,2-dimethoxycarbonylethane-1,2-yl group, and the formula —$R^{3a}$–$R^{3b}$ represents a hydroxymethyl group or an acetoxymethyl group;

(2) Z represents a 1-i-propylethane-1,2-yl group and the formula —$R^{3a}$–$R^{3b}$ represents a hydrogen atom; and (3) the formula —$R^{3a}$–$R^{3b}$ represents a methyl group, and Z represents the formula:

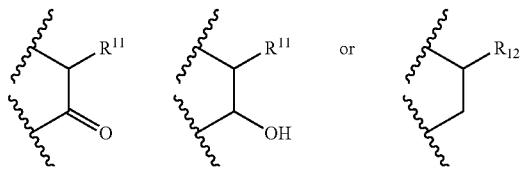

wherein $R^{11}$ represents a hydrogen atom or a methyl group, and $R^{12}$ represents a hydroxyl group, a methyl group or a tetrahydropyran-2H-pyran-2-yl-oxy group.

2. The compound, according to claim 1, a salt thereof or a hydrate thereof, wherein said compound of formula (I) is a compound of formula (Ia):

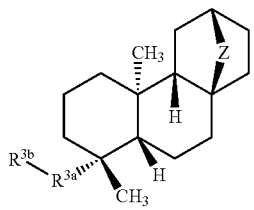
(Ia)

wherein Z, $R^{3a}$ and $R^{3b}$ respectively represent those defined for the above Z, $R^{3a}$ and $R^{3b}$ in claim 1, provided that the following cases (1) to (3) are excluded:

(1) Z represents a 1,2-dicarboxyethane-1,2-yl group or a 1,2-dimethoxycarbonylethane-1,2-yl group, and the formula —$R^{3a}$–$R^{3b}$ represents a hydroxymethyl group or an acetoxymethyl group;

(2) Z represents a 1-i-propylethane-1,2-yl group and the formula —$R^{3a}$–$R^{3b}$ represents a hydrogen atom; and (3) the formula —$R^{3a}$–$R^{3b}$ represents a methyl group, and Z represents the formula:

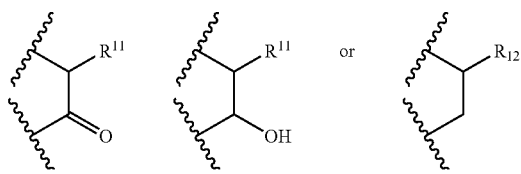

wherein $R^{11}$ represents a hydrogen atom or a methyl group, and $R^{12}$ represents a hydroxyl group, a methyl group or a tetrahydropyran-2H-pyran-2-yl-oxy group.

3. The compound according to claim 1, a salt thereof or a hydrate thereof,
wherein $Q^1$ is

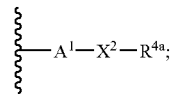

wherein $A^1$, $X^2$ and $R^{4a}$ respectively represent those defined for $A^1$, $X^1$ and $R^{4a}$ in claim 1.

4. The compound according to claim 1, a salt thereof or a hydrate thereof, wherein Z is a group represented by the formula:

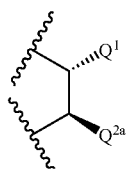

wherein $Q^1$ and $Q^{2a}$ respectively represent those defined for $Q^1$ and $Q^{2a}$ in claim 1.

5. The compound according to claim 1, a salt thereof or a hydrate thereof,
wherein $Q^1$ is

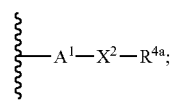

wherein $A^1$, $X^2$, $R^{4b}$ and $R^{4c}$ respectively represent those defined for $A^1$, $X^2$, $R^{4b}$ and $R^{4c}$ in claim 1.

6. The compound according to claim 1, a salt thereof or a hydrate thereof, wherein $R^{3a}$ is a carbonyl group.

7. A compound represented by the following formula, or a salt thereof or a hydrate thereof:

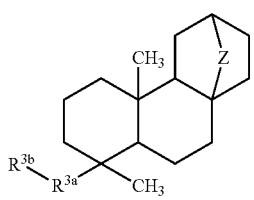
(I)

wherein Z represents a bivalent organic group of from 2 to 3 carbon atoms, provided that Z may have one or two group(s) selected from the group consisting of those represented by the following formula:

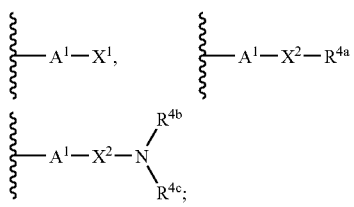 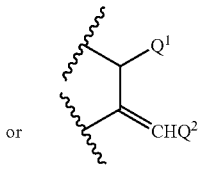

wherein $A^1$ represents an optionally substituted $C_{1-6}$ alkylene group or a single bond;

$X^1$ represents a halogen atom or a cyano group;

$X^2$ represents the formula $—S(O)_m—$, an oxygen atom, a carbonyl group or a single bond, wherein m of $—S(O)_m—$ is an integer of 0, 1 or 2;

$R^{4a}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{1-6}$ alkoxy group or a hydroxyl group; and $R^{4b}$ and $R^{4c}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group;

wherein in the case where Z is a 1,2-ethylene group not having a substituent or a 1,2-vinylene group not having a substituent is excluded;

$R^{3a}$ represents a carbonyl group, a methylene group or a single bond; and wherein $R^{3b}$ is a hydroxyl group.

8. The compound according to claim 1, a salt thereof or a hydrate thereof, wherein $Q^{2a}$ is a hydroxyl group.

9. A compound represented by the following formula, or a salt thereof or a hydrate thereof:

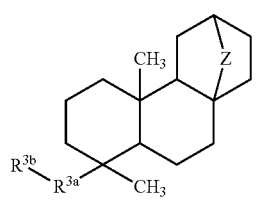

(I)

wherein Z is a group represented by the formula:

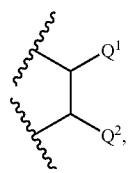 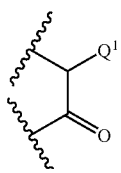

-continued

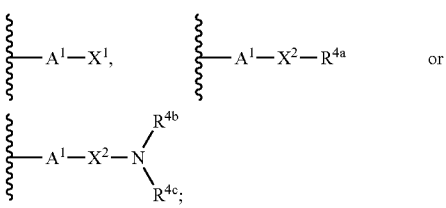

wherein $Q^1$ is a group represented by the formula $-A^1-S(O)_m—R^{4a}$, wherein $A^1$ represents an optionally substituted $C_{1-6}$ alkylene group or a single bond, m is an integer of 0, 1 or 2, and $R^{4a}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{1-6}$ alkoxy group or a hydroxyl group;

wherein $Q^2$ represents a group represented by the formula:

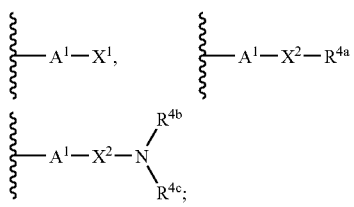

wherein $A^1$ represents an optionally substituted $C_{1-6}$ alkylene group or a single bond;

$X^1$ represents a halogen atom or a cyano group;

$X^2$ represents the formula $—S(O)_m—$, an oxygen atom, a carbonyl group or a single bond, wherein m of $—S(O)_m—$ is an integer of 0, 1 or 2;

$R^{4a}$ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{1-6}$ alkoxy group or a hydroxyl group; and $R^{4b}$ and $R^{4c}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group;

wherein in the case where Z is a 1,2-ethylene group not having a substituent or a 1,2-vinylene group not having a substituent is excluded;

$R^{3a}$ represents a carbonyl group, a methylene group or a single bond; and $R^{3b}$ represents a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, a hydroxyl group, a cyano group or a group represented by the formula $—NR^{5a}R^{5b}$, wherein $R^{5a}$ and $R^{5b}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group, provided that the following cases (1) to (3) are excluded:
(1) Z represents a 1,2-dicarboxyethane-1,2-yl group or a 1,2-dimethoxycarbonylethane-1,2-yl group, and the formula —$R^{3a}$–$R^{3b}$ represents a hydroxymethyl group or an acetoxymethyl group;
(2) Z represents a 1-i-propylethane-1,2-yl group and the formula —$R^{3a}$–$R^{3b}$ represents a hydrogen atom; and
(3) the formula —$R^{3a}$–$R^{3b}$ represents a methyl group, and Z represents the formula:

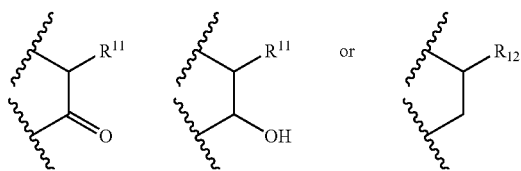

wherein $R^{11}$ represents a hydrogen atom or a methyl group, and $R^{12}$ represents a hydroxyl group, a methyl group or a tetrahydropyran-2H-pyran-2-yl-oxy group.

10. The compound according to claim 1, a salt thereof or a hydrate thereof, wherein $R^{4a}$ is an optionally substituted methyl group, an optionally substituted ethyl group, an optionally substituted n-propyl group or an optionally substituted i-propyl group.

11. The compound according to claim 1, a salt thereof or a hydrate thereof, wherein $A^1$ is a methylene group.

12. A compound represented by the following formula, or a salt thereof or a hydrate thereof:

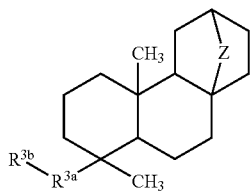

(I)

wherein Z represents a bivalent organic group of from 2 to 3 carbon atoms, provided that Z may have one or two group(s) selected from the group consisting of those represented by the following formula:

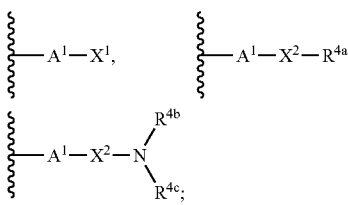

wherein $A^1$ represents an optionally substituted $C_{1-6}$ alkylene group or a single bond;
$X^1$ represents a halogen atom or a cyano group;
$X^2$ represents the formula —$S(O)_m$—, wherein m is 1;
$R^{4a}$ represents a hydrogen atom, an optionally substituted $C_{1-6}$ alkyl group, an optionally substituted $C_{1-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{1-6}$ alkoxy group or a hydroxyl group; and
$R^{4b}$ and $R^{4c}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group;
wherein in the case where Z is a 1,2-ethylene group not having a substituent or a 1,2-vinylene group not having a substituent is excluded;
$R^{3a}$ represents a carbonyl group, a methylene group or a single bond; and
$R^{3b}$ represents a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, a hydroxyl group, a cyano group or a group represented by the formula —$NR^{5a}R^{5b}$,
wherein $R^{5a}$ and $R^{5b}$ are independent of each other and each represents a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{6-14}$ aromatic hydrocarbon cyclic group, an optionally substituted from 5- to 14-membered aromatic heterocyclic group, an optionally substituted $C_{2-7}$ acyl group or an optionally substituted $C_{1-6}$ alkylsulfonyl group, provided that the following cases (1) to (3) are excluded:
(1) Z represents a 1,2-dicarboxyethane-1,2-yl group or a 1,2-dimethoxycarbonylethane-1,2-yl group, and the formula —$R^{3a}$–$R^{3b}$ represents a hydroxymethyl group or an acetoxymethyl group;
(2) Z represents a 1-i-propylethane-1,2-yl group and the formula —$R^{3a}$–$R^{3b}$ represents a hydrogen atom; and
(3) the formula —$R^{3a}$–$R^{3b}$ represents a methyl group, and Z represents the formula:

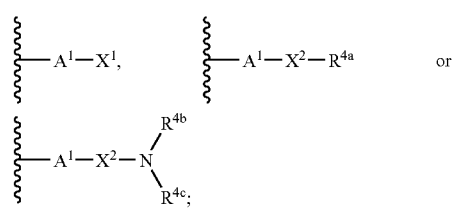

wherein $R^{11}$ represents a hydrogen atom or a methyl group, and $R^{12}$ represents a hydroxyl group, a methyl group or a tetrahydropyran-2H-pyran-2-yl-oxy group.

13. The compound according to claim 1, a salt thereof or a hydrate thereof, wherein $A^1$ represents a $C_{1-6}$ alkylene group or a single bond; $R^{4a}$ represents a hydrogen atom, a $C_{1-6}$ alkyl group, a $C_{2-6}$ alkenyl group, a $C_{2-6}$ alkynyl group, a $C_{6-14}$ aromatic hydrocarbon cyclic group, a 5- to 14-membered aromatic heterocyclic group, a $C_{1-6}$ alkoxy group or a hydroxyl group; $R^{4b}$ and $R^{4c}$ are independent of each other and each represents a hydrogen atom, a $C_{1-6}$ alkyl group, a $C_{2-6}$ alkenyl group, a $C_{2-6}$ alkynyl group, a $C_{6-14}$ aromatic hydrocarbon cyclic group, a 5- to 14-membered aromatic heterocyclic group, a $C_{2-7}$ acyl group or a $C_{1-6}$ alkylsulfonyl group; and $R^{5b}$ represents a hydrogen atom, a halogen atom, a $C_{1-6}$ alkyl group, a $C_{2-6}$ alkenyl group, a $C_{2-6}$ alkynyl group, a $C_{1-6}$ alkoxy group, a hydroxyl group, a cyano group or a group represented by the formula —$NR^{5a}R^{5b}$ wherein $R^{5a}$ and $R^{5b}$ are independent of each other and each represents a hydrogen atom, a $C_{1-6}$ alkyl group, a $C_{2-6}$ alkenyl group, a $C_{2-6}$ alkynyl group, a $C_{6-14}$ aromatic hydrocarbon cyclic group, a 5- to 14-membered aromatic heterocyclic group, a $C_{2-7}$ acyl group or a $C_{1-6}$ alkylsulfonyl group.

14. The compound according to claim 1, a salt thereof or a hydrate thereof, wherein $Q^{2a}$ represents a hydrogen atom, a halogen atom, a $C_{1-6}$ alkyl group, a $C_{2-6}$ alkenyl group, a $C_{2-6}$ alkynyl group, a $C_{1-6}$ alkoxy group, a hydroxyl group or a group represented by the formula —$NR^{6a}R^{6b}$, wherein $R^{6a}$ and $R^{6b}$ are independent of each other and each represents a hydrogen atom, a $C_{1-6}$ alkyl group, a $C_{2-6}$ alkenyl group, a $C_{2-6}$ alkynyl group, a $C_{2-7}$ acyl group or a $C_{1-6}$ alkylsulfonyl group.

15. A pharmaceutical composition comprising the compound according to claim 1, a salt thereof or a hydrate thereof; and a pharmaceutically acceptable carrier.

16. A pharmaceutical composition comprising the compound according to claim 7, a salt thereof or a hydrate thereof; and a pharmaceutically acceptable carrier.

17. A pharmaceutical composition comprising the compound according to claim 9, a salt thereof or a hydrate thereof; and a pharmaceutically acceptable carrier.

18. A pharmaceutical composition comprising the compound according to claim 12, a salt thereof or a hydrate thereof; and a pharmaceutically acceptable carrier.

19. A method for treating a disease or condition selected from the group consisting of glaucoma, retinopathy of prematurity, diabetic retinopathy, macular degeneration, hearing disorder, atopic dermatitis, contact dermatitis or hyperesthesia, said method comprising:

administering a pharmacologically effective amount of the compound according to claim 1, a salt thereof or a hydrate thereof to a patient with said disease or condition.

20. A method for treating a disease or condition selected from the group consisting of glaucoma, retinopathy of prematurity, diabetic retinopathy, macular degeneration, hearing disorder, atopic dermatitis, contact dermatitis or hyperesthesia, said method comprising:

administering a pharmacologically effective amount of the compound according to claim 7, a salt thereof or a hydrate thereof to a patient with said disease or condition.

21. A method for treating a disease or condition selected from the group consisting of glaucoma, retinopathy of prematurity, diabetic retinopathy, macular degeneration, hearing disorder, atopic dermatitis, contact dermatitis or hyperesthesia, said method comprising:

administering a pharmacologically effective amount of the compound according to claim 9, a salt thereof or a hydrate of them to a patient with said disease or condition.

22. A method for treating a disease or condition selected from the group consisting of glaucoma, retinopathy of prematurity, diabetic retinopathy, macular degeneration, hearing disorder, atopic dermatitis, contact dermatitis or hyperesthesia, said method comprising:

administering a pharmacologically effective amount of the compound according to claim 12, a salt thereof or a hydrate thereof to a patient with said disease or condition.

* * * * *